US 11,512,114 B2

(12) United States Patent
Enke et al.

(10) Patent No.: US 11,512,114 B2
(45) Date of Patent: Nov. 29, 2022

(54) MODIFIED MICROCYSTINS AND NODULARINS

(71) Applicant: Cyano Biotech GmbH, Berlin (DE)

(72) Inventors: Heike Enke, Berlin (DE); Wolfram Lorenzen, Berlin (DE); Stefan Jahns, Berlin (DE); Dan Enke, Berlin (DE); Timo Niedermeyer, Halle Saale (DE); Julia Moschny, Sulzbach-Rosenberg (DE)

(73) Assignee: Cyano Biotech GmbH, Berlin (DE)

( * ) Notice: Subject to any disclaimer, the term of this patent is extended or adjusted under 35 U.S.C. 154(b) by 0 days.

(21) Appl. No.: 16/605,264

(22) PCT Filed: May 9, 2018

(86) PCT No.: PCT/EP2018/062129
§ 371 (c)(1),
(2) Date: Oct. 15, 2019

(87) PCT Pub. No.: WO2018/206715
PCT Pub. Date: Nov. 15, 2018

(65) Prior Publication Data
US 2020/0087348 A1    Mar. 19, 2020

(30) Foreign Application Priority Data
May 9, 2017    (EP) .................................... 17170283

(51) Int. Cl.
C07K 7/64          (2006.01)
A61K 47/68         (2017.01)
A61K 38/00         (2006.01)

(52) U.S. Cl.
CPC ............ C07K 7/64 (2013.01); A61K 47/6829 (2017.08); A61K 47/6851 (2017.08); A61K 38/00 (2013.01)

(58) Field of Classification Search
CPC .. C07K 7/64; C07K 2319/30; A61K 47/6851; A61K 47/6829; A61K 38/00; A61K 47/6855; A61P 35/00
See application file for complete search history.

(56) References Cited

U.S. PATENT DOCUMENTS

| | | |
|---|---|---|
| 2004/0101899 A1 | 5/2004 | Dillon et al. |
| 2005/0276812 A1 | 12/2005 | Ebens, Jr. et al. |
| 2007/0092940 A1 | 4/2007 | Eigenbrot et al. |
| 2007/0275885 A1 | 11/2007 | Monk et al. |
| 2019/0263868 A1 | 8/2019 | Neilan et al. |

FOREIGN PATENT DOCUMENTS

| | | |
|---|---|---|
| CN | 101125889 | 2/2008 |
| EP | 1 698 638 | 9/2006 |
| JP | 2006520194 | 9/2006 |
| JP | 2013545438 | 12/2013 |
| JP | 2010059208 | 3/2018 |
| WO | 2002/24909 | 3/2002 |
| WO | 2002/38766 | 5/2002 |
| WO | 2002/094852 | 11/2002 |
| WO | 2003/014294 | 2/2003 |
| WO | 2003/035846 | 5/2003 |
| WO | 2003/045422 | 6/2003 |
| WO | 2004/011611 | 2/2004 |
| WO | 2004/058309 | 6/2004 |
| WO | 2004/066933 | 8/2004 |
| WO | 2012/032181 | 3/2012 |

OTHER PUBLICATIONS

Namikoshi et al, J.Org.Chem., 1992, 57, 866-872 (Year: 1992).*
Mikhailov et al, Toxicon, 2001, 39, 477-483 (Year: 2001).*
Nolting, Antibody-Drug Conjugates, Methods in Molecular Biology 2013, 1045, ch.5, Linker Technologies of Drug-Antibody conjugates, 71-100 (Year: 2013).*
Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
Sadik et al, Chem.Commun., 2004, 1136-1137 (Year: 2004).*
U.S. Appl. No. 16/605,248, filed Oct. 15, 2019, Enke et al.
International Search Report dated Jan. 3, 2019 in PCT/EP2018/062129.
Written Opinion dated Jan. 3, 2019 in PCT/EP2018/062129.
International Preliminary Report on Patentability dated Jul. 1, 2019 in PCT/EP2018/062129.
Barnett et al., Genomics 3, 59-66 (1988).
Coussens et al., Science 230, 1132-1139 (1985).
Niedermeyer et al., PLoS ONE 9(3): e91476 (2014) (7 pages).
Thompson et al., Science 293 (5537), 2108-2111 (2001).
Tillich et al., BMC Microbiology 2014, 14:239 (13 pages).
Zemskov et al., J. Org. Chem. 2017, 82, 3680-3691.
Bouaïcha, et al., "Structural Diversity, Characterization and Toxicology of Microcystins," Toxins, 2019, 11, 714, 40 pages.
"Antibody-Drug Conjugates", Methods in Molecular Biology 1045, ed. Laurent Ducry, Humana Press; 2013, complete book, 315 pages.
"Bioconjugation", Methods in Molecular Biology 2033, ed. Sam Massa and Nick Devoogdt, Humana Press; 2019, complete book, 317 pages.
H. Chen, "Environmental Factors Regulating Cyanobacterial Dynamics and the Occurrence of Microcystin, with an Emphasis on Nitrogen", PhD Dissertation, University of Alberta, Spring 2009. (Year: 2000).

(Continued)

Primary Examiner — Sudhakar Katakam
(74) Attorney, Agent, or Firm — Grüneberg and Myers PLLC

(57) ABSTRACT

A compound includes cytotoxic agents such as microcystin and nodularin. More specifically, a modified microcystin and/or nodularin compound contains one or more modified substrates, wherein one or more modified substrates include an anchor group directly accessible or transformable for use in conjugation chemistry (incl. click chemistry), for the attachment of a targeting moiety. This compound is useful for cancer treatment.

15 Claims, 45 Drawing Sheets

Specification includes a Sequence Listing.

(56) References Cited

OTHER PUBLICATIONS

Drago, et al., "*Unlocking the potential of antibody-drug conjugates for cancer therapy*", Nature Reviews Clinical Oncology, 2021, vol. 18, pp. 327-344.
Kries et al. Angew. Chem. Int. Ed. 2014, 53, 10105-10108.
Moschny et al., GA 2017, 65th International Congress and Annual Meeting of the Society for Medicinal Plant and Natural Product Research, Sep. 3-9, 2017, Basel, Switzerland, Poster.
Nejadmoghaddam et al., "*Antibody-Drug Conjugates: Possibilities and Challenges*", Avicenna Journal of Medical Biotechnology, March 2019; vol. 11, No. 1, 21 pages.
"*Next Generation Antibody Drug Conjugates (ADCs) and Immunotoxins*", Milestones in Drug Therapy; 2017, ed. Ulf Grawunder and Stefan Barth, entire book, 191 pages.
Niedermeyer et al., Nat. Prod. Bioprospect. (2014) 4:37-45.
Spicer et al., Nat. Commun. 5:4740 (2014) (14 pages).
Tonk et al., "*Amino acid availability determines the ratio of microcystin variants in the cyanobacterium Planktothris agardhii*", FEMS Microbiology Ecology, 2008, vol. 65, pp. 383-390.
Welker et al., "*Diversity of coexisting Planktothrix (Cyanobacteria) chemotypes deduced by mass spectral analysis of microcystins and other oligopeptides*", Archives of Microbiology; 2004, vol. 182, pp. 288-298.
Yan et al., "*Comparative effects of inorganic and organic nitrogen on the growth and microcystin production of Microcystis Aeruginosa*", World Journal of Microbiology and Biotechnology; 2015, vol. 31, pp. 763-772.
Acchione et al., "Impact of linker and conjugation chemistry on antigen binding, Fc receptor binding and thermal stability of model antibody-drug conjugates", mAbs, vol. 4, Issue 3, May/Jun. 2012, pp. 362-372.
Bernardes, et al., "Site-specific chemical modification of antibody fragments using traceless cleavable linkers", Nature Protocols, vol. 8, No. 11, 2013, pp. 2079-2089.
Casi et al., "Antibody-drug conjugates: Basic concepts, examples and future perspectives", Journal of Controlled Release, vol. 161, 2012, pp. 422-428.
Goldberg et al., "Three-dimensional structure of the catalytic subunit of protein serine/threonine phosphatase-1", Nature, vol. 376, Aug. 31, 1995, pp. 745-753.
Jain et al., "Current ADC Linker Chemistry", Pharm. Res., vol. 32, 2015, pp. 3526-3540.
Krivec et al., "Development of microcystin derivates as novel agents against OATP1B3-expressing tumors", Planta Med., vol. 82, (S01):S1-S381, 2016, 1 page.
McCombs et al., "Antibody Drug Conjugates: Design and Selection of Linker, Payload and Conjugation Chemistry", The AAPS Journal, vol. 17, No. 2, Mar. 2015, pp. 339-351.
VanBrunt et al., "Genetically Encoded Azide Containing Amino Acid in Mammalian Cells Enables Site-Specific Antibody-Drug Conjugates Using Click Cycloaddition Chemistry", BC Bioconjugate Chemistry, 2015, 12 pp.
Wang et al., "Antibody Drug Conjugates", The 21$^{st}$ Century magic Bullets for Cancer, AAPS Advances in the Pharmaceutical Sciences Series, vol. 17, 2015, pp. 1-252.

* cited by examiner

NODULARINS

ANABAENOPEPTINS/ OSCILLAMIDES

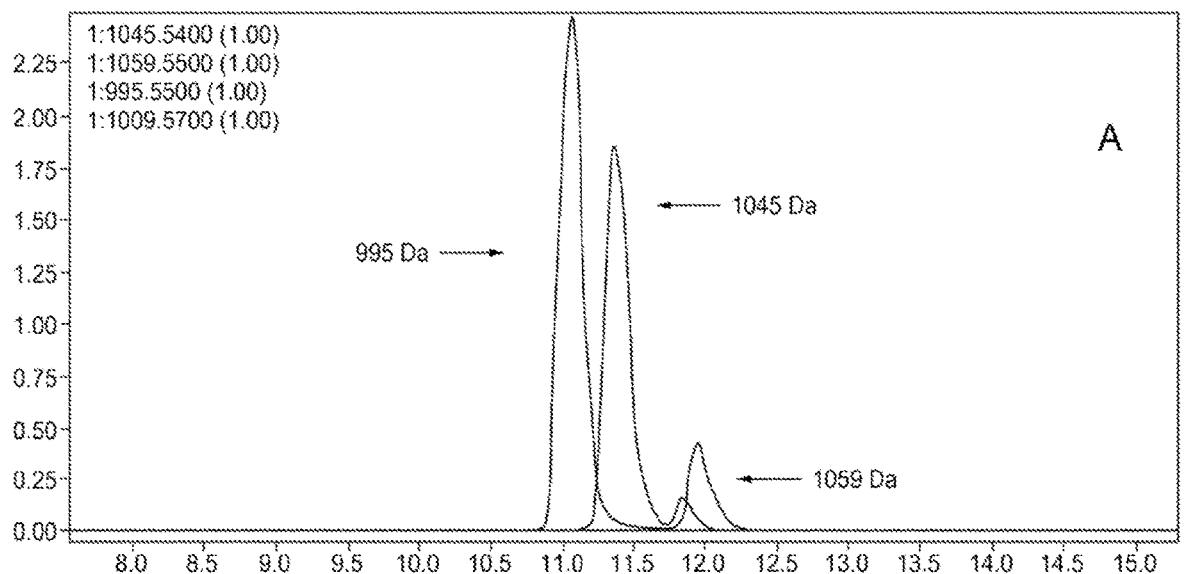
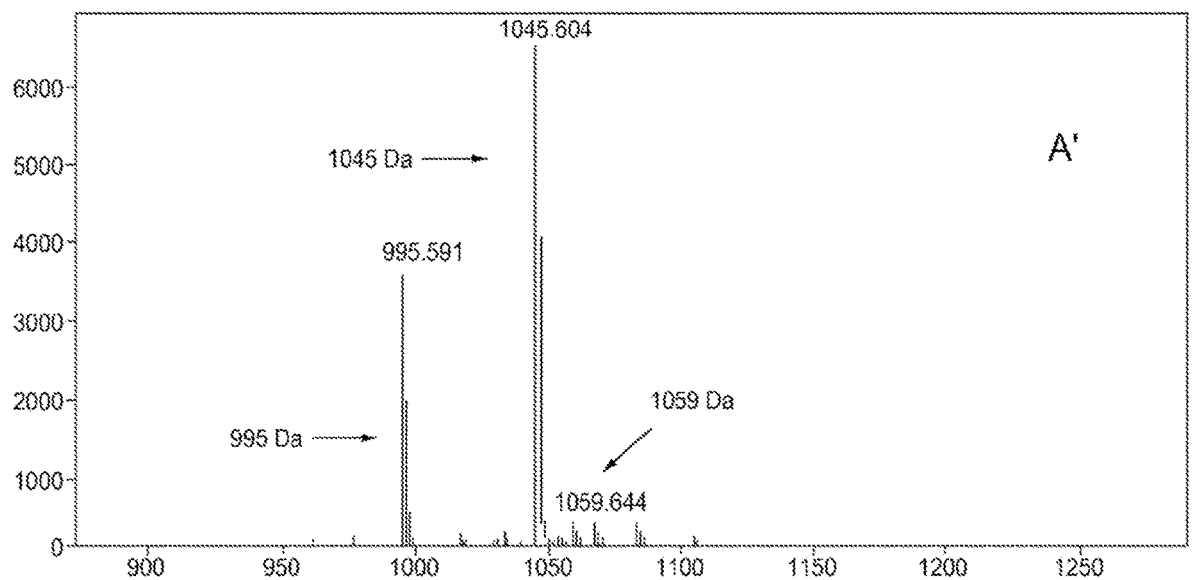
FIG. 4A

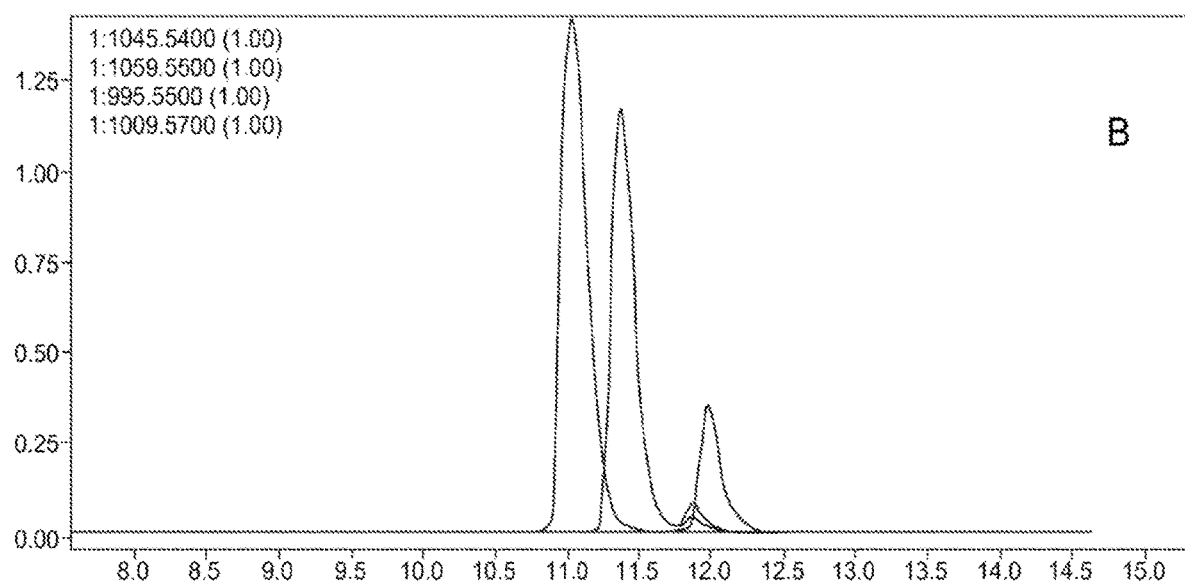
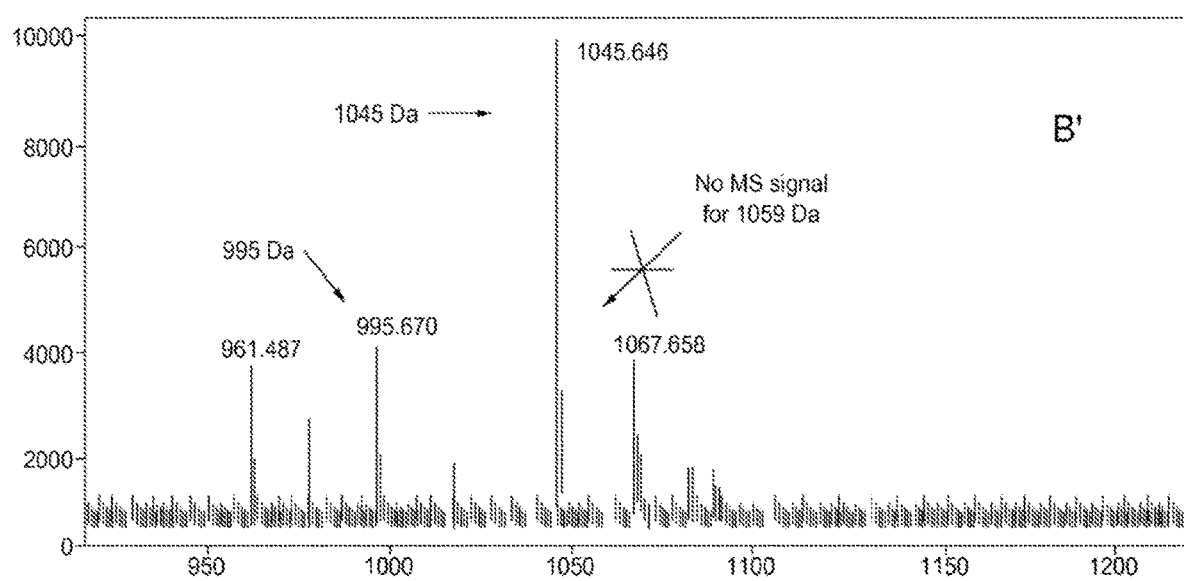
FIG. 4B

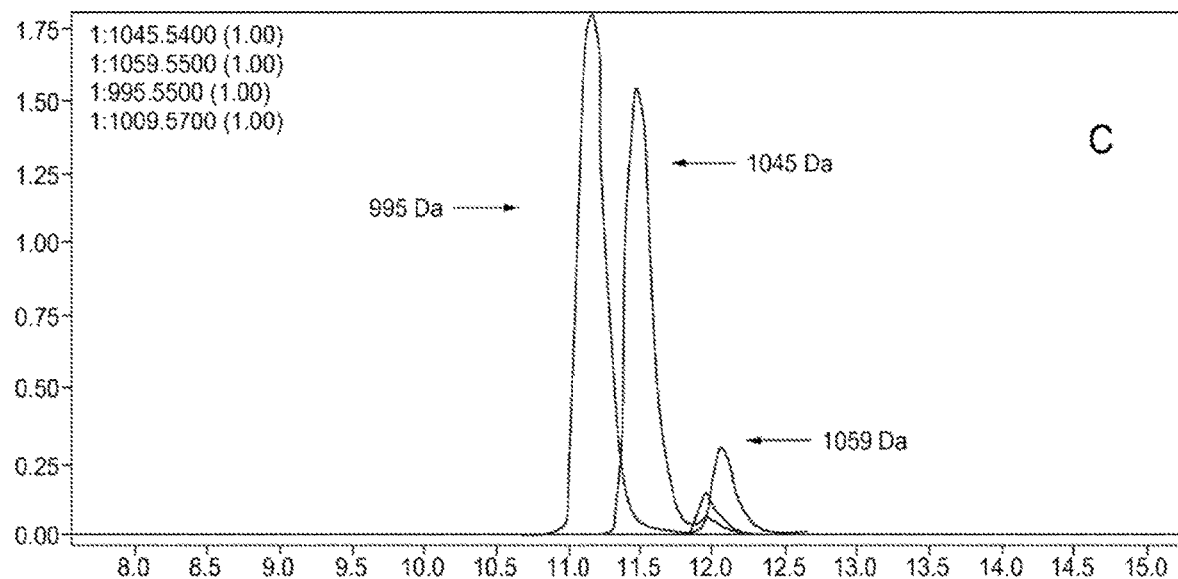
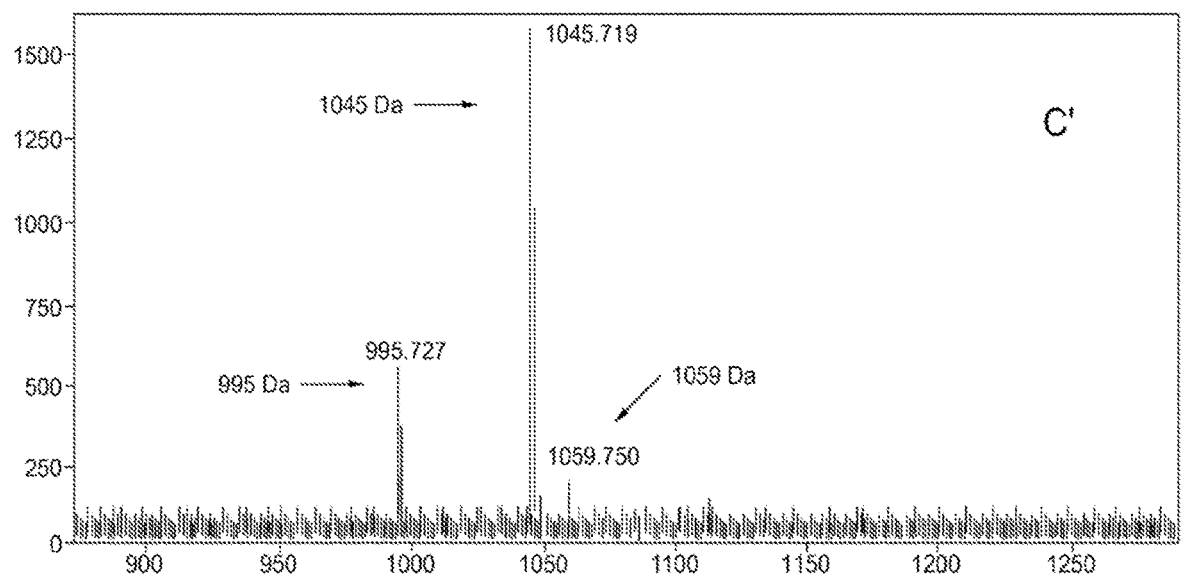
FIG. 4C

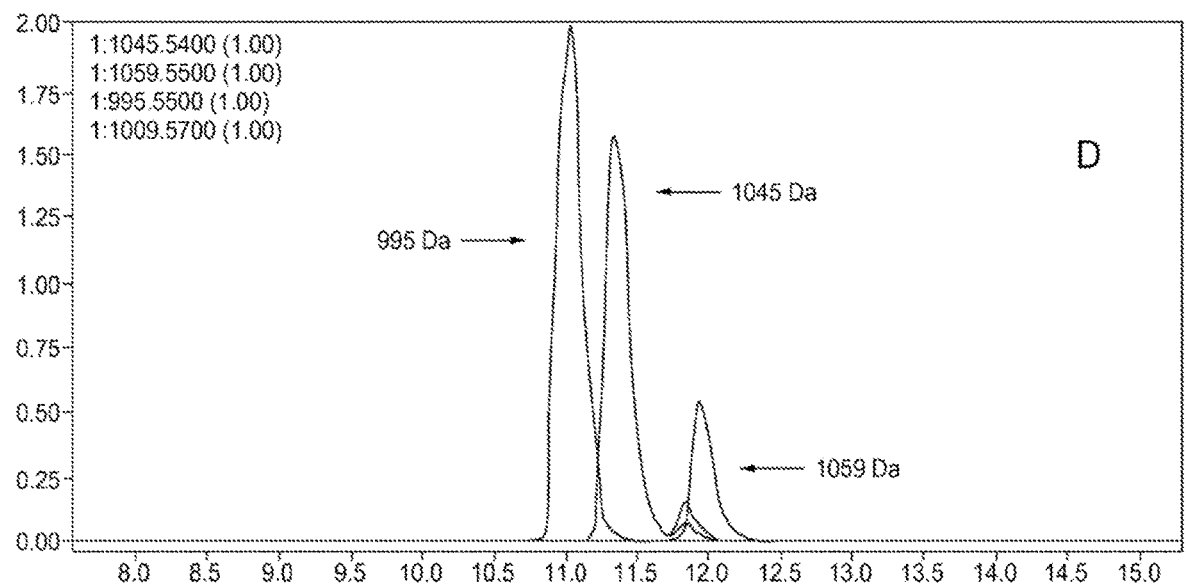
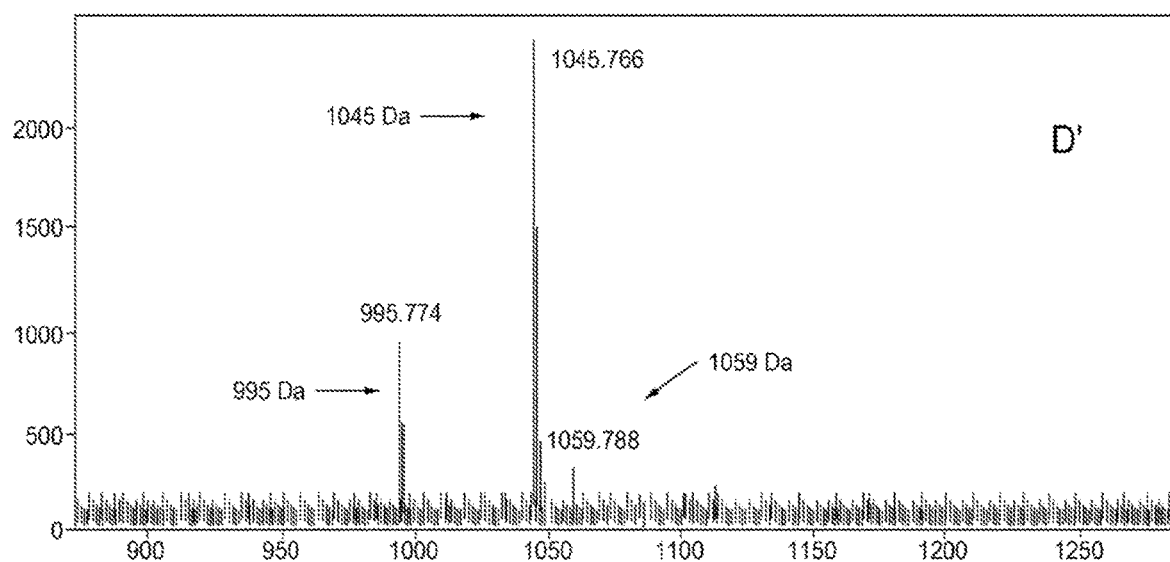
FIG. 4D

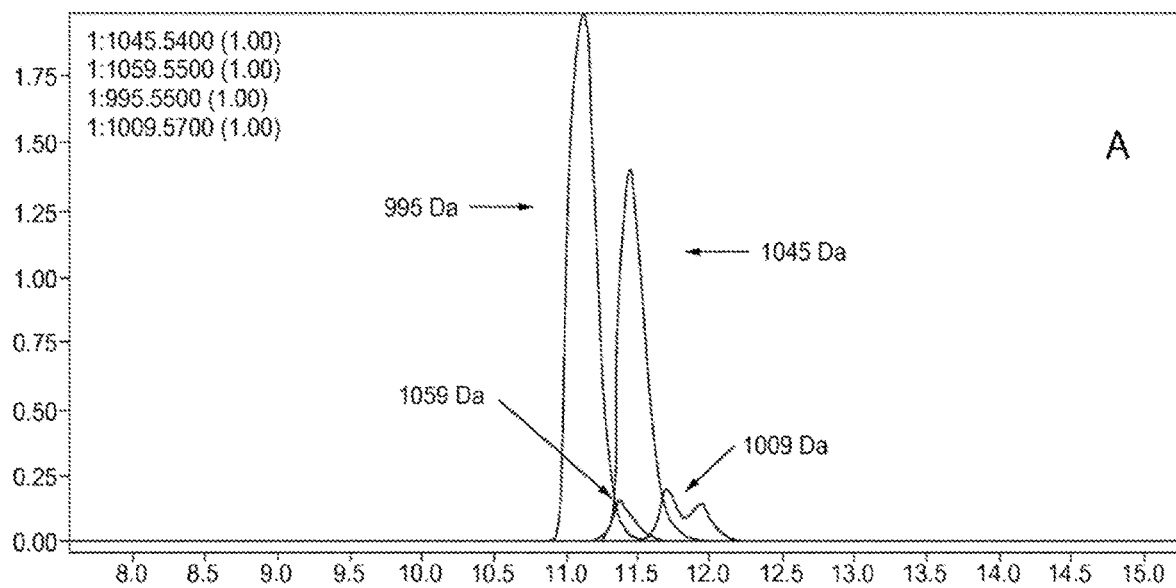
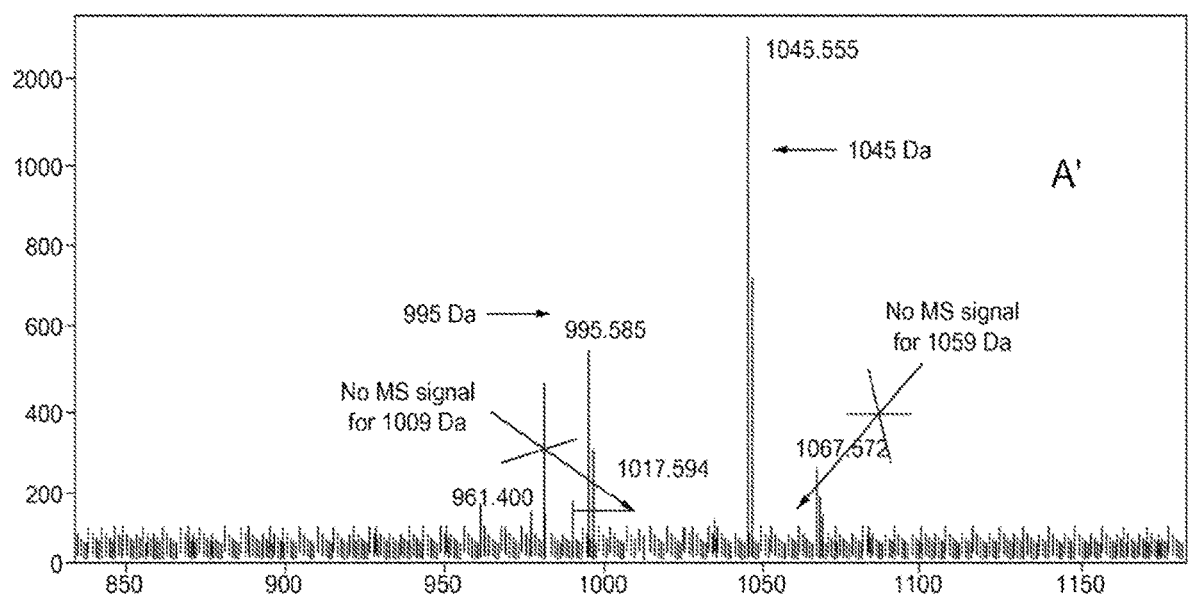
FIG. 5A

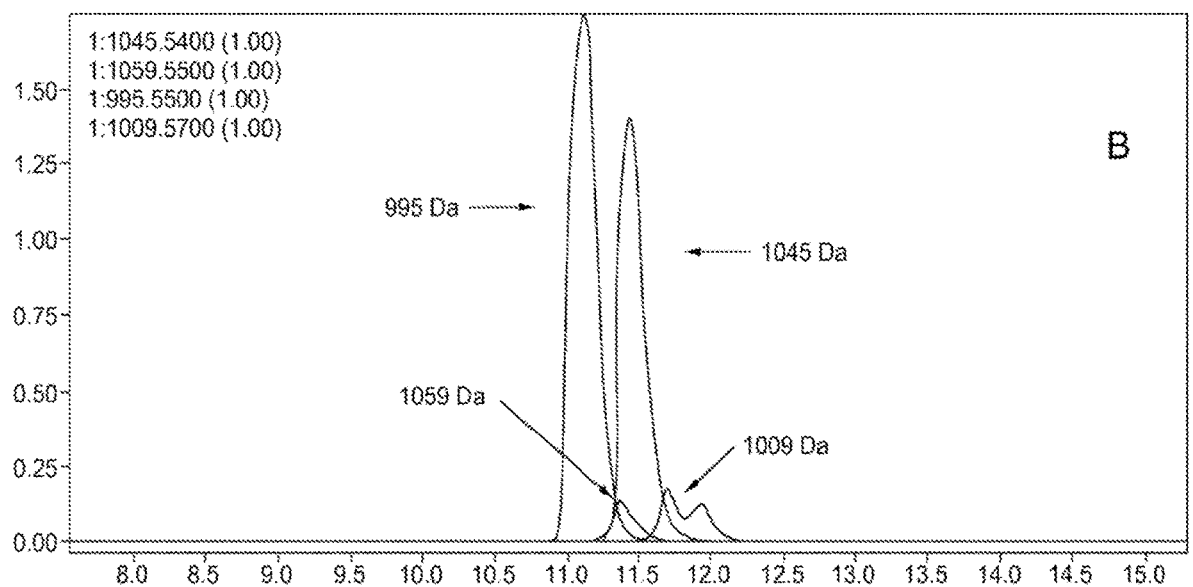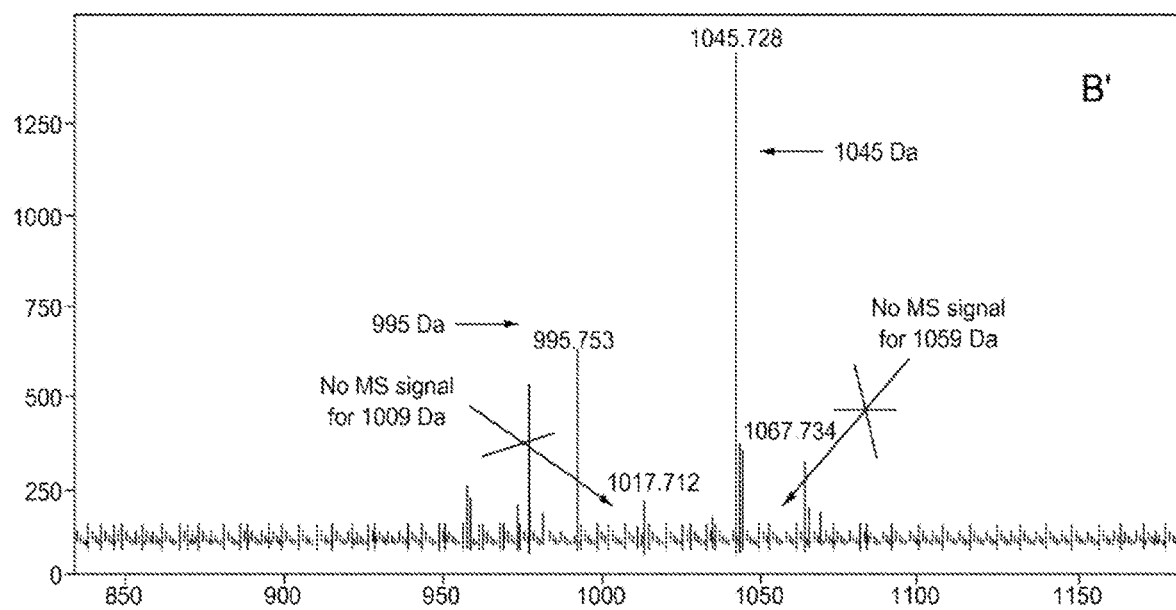
FIG. 5B

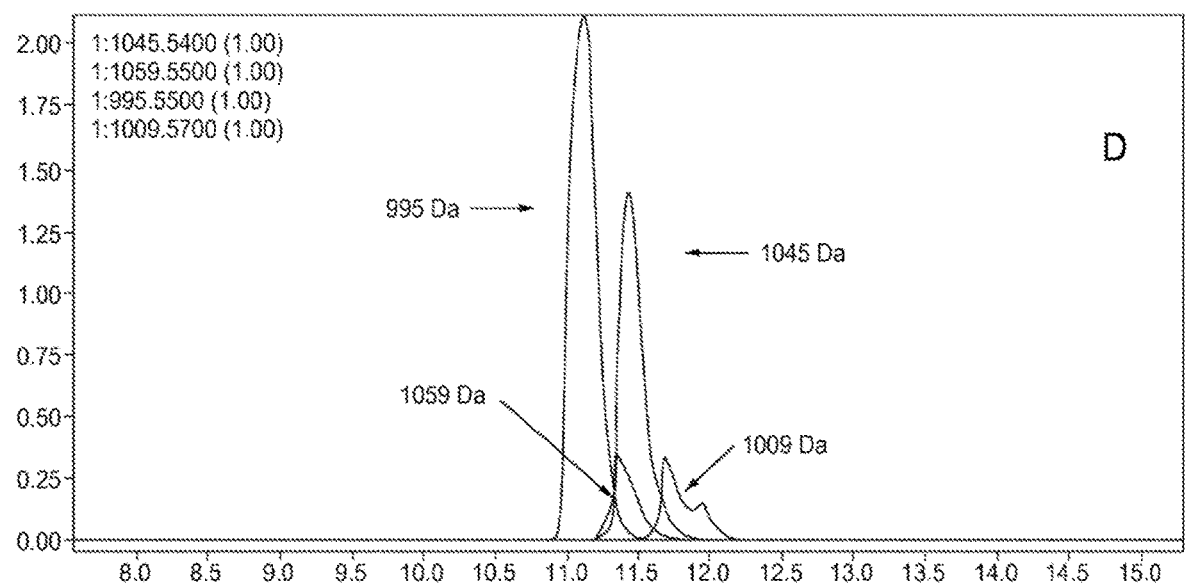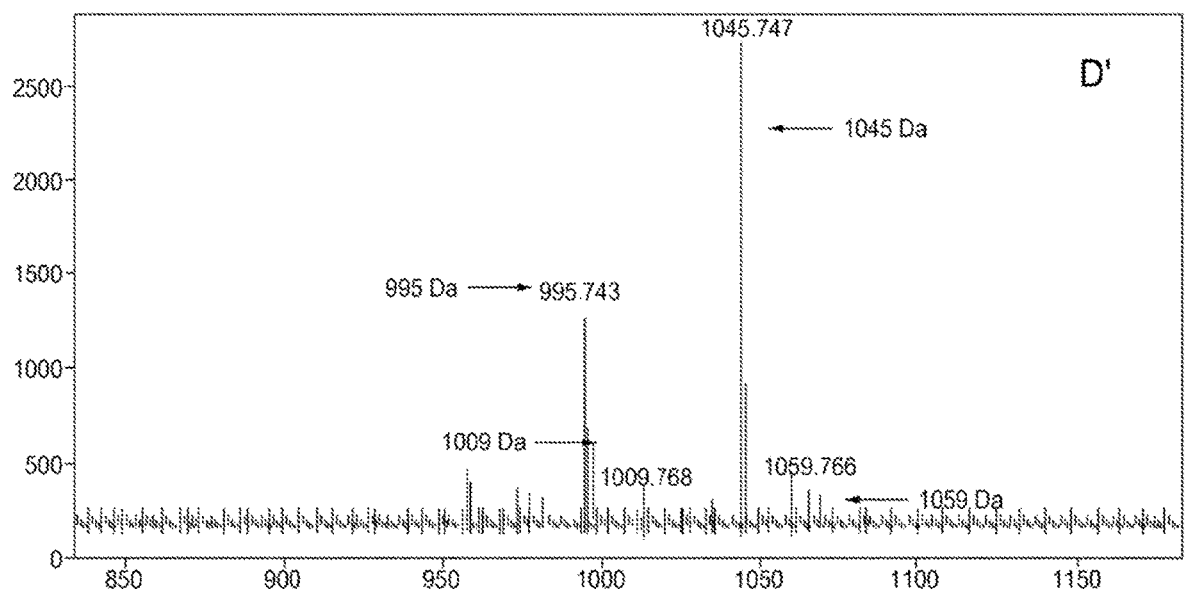
FIG. 5D

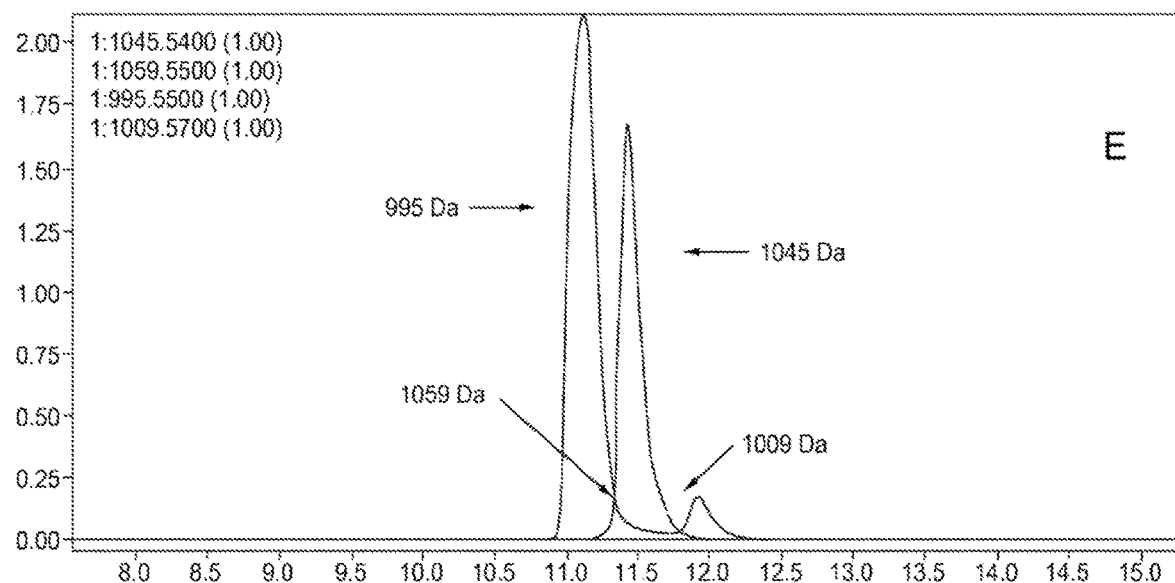
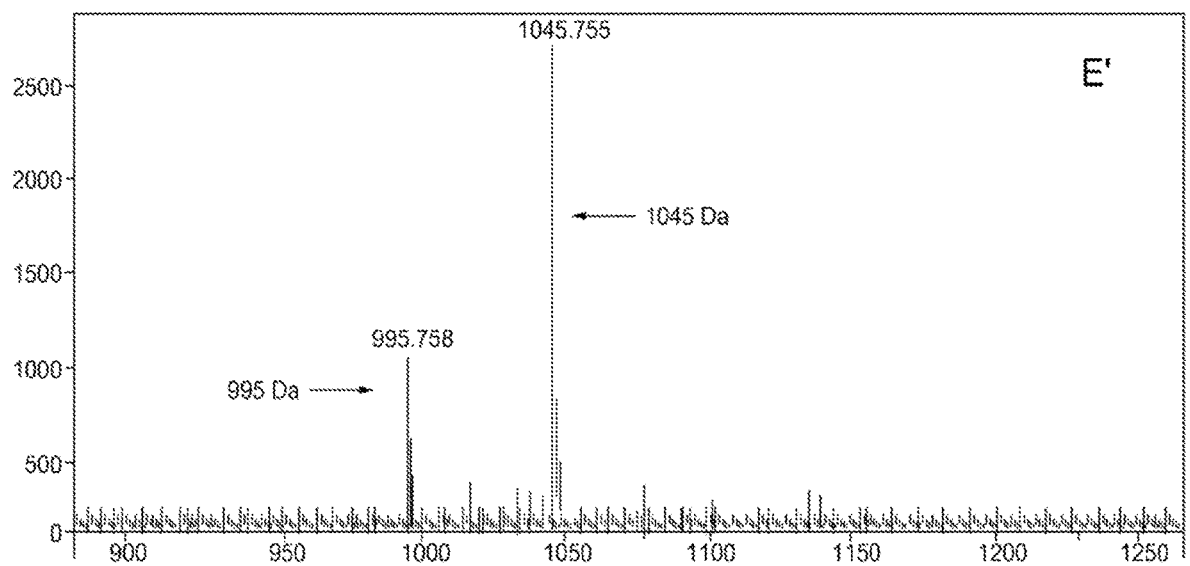
FIG. 5E

```
Query  541  GILKAGGAYVPLDPDYPTERLGDILSDSGVSLVLTQESLGDFLPQTGAESLCLDRDWEKI  600
            GILKAGGAYVPLDPDYPTERLGDILSDSGVSLVLTQESLGDFLPQTGAESLCLDRDWEKI
Sbjct  541  GILKAGGAYVPLDPDYPTERLGDILSDSGVSLVLTQESLGDFLPQTGAESLCLDRDWEKI  600

Query  601  ATYSPENPFNLTTPENLAYVIYTSGSTGKPKGVLISHRGLMNSICWYQDAFEITPLDKTT  660
            ATYSPEN FNLTTPENLAYVIYTSGSTGKPKGVLISHRGLMN ICW+QDAFEITPLDK T
Sbjct  601  ATYSPENHFNLTTPENLAYVIYTSGSTGKPKGVLISHRGLMNLICWHQDAFEITPLDKIT  660

Query  661  QLARIAFDAAVLELWPCLTAGASLVLVKPEIMQSPPDLRDWLIAQEITVSFLPTPLVEKI  720
            QLARIAFDAAV ELWPCLTAGASLVLVKPEIMQSPPDLRDWLIAQEITVSFLPTPLVEKI
Sbjct  661  QLARIAFDAAVWELWPCLTAGASLVLVKPEIMQSPPDLRDWLIAQEITVSFLPTPLVEKI  720

Query  721  LSLEWDENIALRIILTGGDKLHHYPSGLMPFKLINNYGPTENSVVTTSGLVPDYEEGNPP  780
            LSLEWDENIALRIILTGGDKLHHYPSGLMPFKLINNYGPTENSVVTTSGLV DYEEGNPP
Sbjct  721  LSLEWDENIALRIILTGGDKLHHYPSGLMPFKLINNYGPTENSVVTTSGLVRDYEEGNPP  780

Query  781  SPSIGKPVYNTKIYILDQNLQPLPIGVPGELHISSVGLARGYLNRLELTQEKFISNPFNS  840
            SPSIGKPVYNTKIYILDQNLQPLPIGVPGELHISSVGLARGYLNRLELTQEKFISNPFNS
Sbjct  781  SPSIGKPVYNTKIYILDQNLQPLPIGVPGELHISSVGLARGYLNRLELTQEKFISNPFNS  840
```

FIG. 6

|  | EC 50 |
|---|---|
| Microcystin-ADC-1 | ~7.008e-010 |
| Microcystin-ADC-2 | 2.216e-010 |

FIG. 32

MODIFIED MICROCYSTINS AND NODULARINS

CROSS-REFERENCE TO RELATED APPLICATIONS

This application is a National Stage entry under § 371 of International Application No. PCT/EP2018/062129, filed on May 9, 2018, and which claims the benefit of European Application No. 17170283.0, filed on May 9, 2017.

REFERENCE TO SEQUENCE LISTINGS

The present application is accompanied by an ASCII text file as a computer readable form containing the sequence listing, titled "000870US_SL_ST25", created on Aug. 19, 2022, with the file size of 12,967 bytes, which is incorporated by reference in its entirety.

FIELD OF INVENTION

This invention is in the field of cancer treatment. It is in the field of toxins for use in cancer treatment. It is in the field of microcystins and nodularins and their use in the treatment of diseases such as cancer, metabolic diseases but also for other applications. The invention relates to the field of molecular biology, pharmacy and biotechnology in general and more specifically to the synthesis of modified microcystins and nodularins that are able to target, e.g. a tumor.

BACKGROUND

Microcystins are toxins produced naturally by cyanobacteria, also known as blue-green algae. When excess cyanobacteria grow in a lake or pond, they form an algal bloom, which often appears as a layer of green scum. However, not all green scum on a lake is an algal bloom, and not all algal blooms contain the kinds of cyanobacteria that produce microcystins. There are many microcystin congeners; microcystin-LR is one of the more toxic and well-studied congener. Microcystins are a group of cyclic heptapeptide hepatotoxins produced by a number of cyanobacterial genera. The most notable of which, and namesake, is the widespread genus *Microcystis*. Structurally, most microcystins consist of the generalized structure cyclo(-D-Ala1-X2-D-MeAsp3-Y4-Adda5-D-Glu6-Mdha7-). X and Y are variable L-amino acids, D-MeAsp is D-erythro-β-methylaspartic acid and Mdha is N-methyldehydroalanine. However, while X and Y are the most variable amino acids, variations can be found at all positions of the microcystin core structure (see FIG. 1A). Adda is the cyanobacteria unique C20-β-amino acid 3-amino-9-methoxy-2,6,8-trimethyl-10-phenyl-deca-4,6-dienoic acid. Substitutions of the variable L-amino acids at positions 2 and 4 and less frequently found alterations in the other constituent amino acids result in more than 100 reported natural microcystins to date.

Microcystins are potent inhibitors of type 1 and type 2A protein phosphatases. The IC50 of microcystin-LR for example are 0.03 nM and 0.04 nM for type 1 and type 2A protein phosphatases, respectively.

Protein phosphatases 1 and 2A are two of the major phosphatases in eukaryotic cells that dephosphorylate serine and threonine residues.

Protein phosphatase 2B is inhibited 1000-fold less potently, while six other tested phosphatases and eight tested protein kinases are unaffected.

Nodularins are compounds structurally related to the microcystins, as they are evolutionary derived from microcystin and also contain the amino acid Adda found in the microcystins. They are produced especially by *Nodularia* species, and in contrast to microcystins they are cyclic pentapeptides with the most commonly found congener cyclo[-D-erythro-_-methylAsp-L-Arg-Adda-D-Glu-Mdhb], where Mdhb is N-methyldehydrobutyrate (see FIG. 1B).

Microcystins and nodularins could serve as cancer drugs. It was hypothesized that natural microcystin variants could be isolated that are transported preferentially by the active transporter type OATP1B3 relative to OATP1B1 to advance as anticancer agents with clinically tolerable hepatic toxicity (OATP1B3 transporters are primarily found in cancer tissues, e.g. in liver cancers). Microcystin variants have been isolated and tested for cytotoxicity in cancer cells stably transfected with OATP1B1 and OATP1B3 transporters. Microcystin variants with cytotoxic OATP1B1/OATP1B3 IC50 ratios that ranged between 0.2 and 32 were found, representing a 150-fold range in transporter selectivity. As the microcystin structure has a significant impact on transporter selectivity, it is potentially possible to develop analogs with even more pronounced OATP1B3 selectivity and thus enable their development as anticancer drugs. However, a more specific method of delivery would be preferred. One such method involves the novel concept disclosed herein, of adding a targeting moiety. Ideally for a targeted and highly specific cancer therapy that avoids off-target toxicities, the structural variant of a microcystin and nodularin would carry a targeting moiety (e.g. a cancer-specific monoclonal antibody) and is either not or badly transported by all OATP transporter subtypes or it is exclusively or primarily transported by the cancer-specific OATP subtype 1B3.

Microcystins are difficult to synthesize chemically. One more convenient way of obtaining microcystins involves the in vivo production of microcystins by cyanobacteria.

Previous experiments of academic groups intended to increase product yields of naturally produced non-ribosomal peptides (here microcystins) by feeding of amino acids, which are incorporated in at least one structural variant of the respective microcystin synthesized by the fed strain. More specific, feeding of the amino acids leucine (L, Leu) or arginine (R, Arg) to a cyanobacterial strain that produces the microcystin (MC) variants MC-LR and MC-RR (L for leucine; R for arginine) influences the yield of both variants in dependence of the fed amino acid. Furthermore, feeding of amino acids which are incorporated in at least one structural variant of the respective microcystin synthesized by the fed strain might also influence biomass production.

In addition, it also has been shown that feeding of amino acids that represent slightly modified versions of the amino acids which are naturally incorporated into the respective non-ribosomal peptide produced by the fed strain might be also incorporated into the respective non-ribosomal peptide. This approach is generally known as mutasynthesis. For cyanobacterial non-ribosomal peptides, however, this approach has to date been restricted to simple analogs of natural amino acids such as homo-tyrosine instead of tyrosine (differing by only one methylene group) or halogenated amino acids (differing by only one halogen atom) such as chloro-tyrosine instead of tyrosine. Feeding of more extensively modified amino acids or of amino acids and their analogs that are different from the amino acids that are naturally incorporated into the non-ribosomal peptide have not been reported to date. Moreover, it has been described in the literature that feeding of modified amino acids to be incorporated into microcystins is not possible.

There is a need for modified microcystins and nodularins. There is a need for methods of producing modified microcystins and nodularins as well as for coupling microcystins and nodularins to targeting units (e.g. in connection with the construction of antibody-drug conjugates for targeted therapy of cancers).

SUMMARY OF INVENTION

The problem was solved by producing modified microcystins and nodularins, by means of incorporating one or more modified substrates into microcystins and/or nodularins.

The invention relates to a modified microcystin and/or nodularin compound comprising one or more modified substrates, wherein the at least one modified substrate comprises an anchor group directly accessible or transformable for use in click chemistry, for the attachment of a targeting moiety and/or label and/or for additional structural modifications.

Definitions

Herein, a microcystin according to the invention has the general structure of D-Ala$_1$-X$_2$-D-MeAsp$_3$-Z$_4$-Adda5-D-Glu6-Mdha7, where structural variations may in principle occur at all positions but most frequently at X and Z (see FIG. 1A). These are the variable L-amino acids. D-MeAsp is D-erythro-b-methyl aspartic acid, Mdha is N-methyldehydroalanine, and Adda is 3-amino-9-methoxy-2,6,8-trimethyl-10-phenyldeca-4,6-dienoic acid. Demethylation at position 3 and/or 7 and methylation at position 6 is also within the scope of the invention as well as further modifications at the position 1, 5 and 7 as indicated in FIG. 1A.

Herein we demonstrate multiple combinations of the variable L-amino acids (X and Z) in positions 2 and 4 and modifications in the other D-amino acids.

Herein, nodularin is a compound of monocyclic pentapeptide consisting of cyclo[-D-erythro-methylAsp (iso-linkage)-L-Arg-Adda-D-Glu(iso-linkage)-Mdhb], where Mdhb stands for N-methyldehydrobutyrate and Adda is the particular C20-amino acid: 3-amino-9-methoxy-2,6,8-trimethyl-10-phenyldeca-4,6-dienoic acid whereas all positions can naturally be slightly modified as indicated in FIG. 1B. Nodularin closely resembles microcystins with respect to structure and biological activity.

Modifications of microcystins and nodularins shall not occur at the position for Adda and D-Glu as these two positions are essential for the inhibiting activity against PP1 and PP2A.

Herein, microcystin and nodularin in all their modified variations are referred to as cytotoxic agents, or CA.

Herein, a CA producing cyanobacterial strain is referred to as a CA-STRAIN.

Herein targeting moieties are proteins (mainly antibodies and their fragments), peptides, nucleic acids (aptamers), small molecules, or others (vitamins or carbohydrates) as well as nano particles. Monoclonal antibodies (mAbs) are preferred as escort molecules for the targeted delivery of the altered and modified microcystins or nodularins. However, small molecules can also act as targeting moieties as they might influence the physicochemical properties of said peptides. One example for this is the coupling with hydrophilic moieties such as sugars, e.g. to increase the solubility of said peptide in water. Furthermore, the attached small molecule can have the purpose of altering the peptides in vivo pharmacokinetic properties, e.g. attachment of a functional group prone to in vivo metabolism can increase hepatic clearance and reduce hepatic toxicity, or can influence transporter selectivity and therefore the (active) uptake of the modified non-ribosomal peptide by cells.

Herein an ADC (ADC for antibody-drug conjugate) is a CA linked to a targeting moiety (TM) directly or via a linker (L) whereas by definition of an ADC the targeting moiety is an antibody.

The term antibody (AB) herein is used in the broadest sense and specifically covers monoclonal antibodies, polyclonal antibodies, dimers, multimers, multispecic antibodies (e.g., bispecific antibodies), and antibody fragments, so long as they exhibit the desired biological activity. Antibodies may be murine, human, humanized, chimeric, or derived from other species. An antibody is a protein generated by the immune system that is capable of recognizing and binding to a specific antigen. A target antigen generally has numerous binding sites, also called epitopes, recognized by complementarity-determining regions (CDRs) on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immuno-specifically binds an antigen of a target of interest or part thereof, such targets including but not limited to, cancer cells, microbial cells or cells that produce autoimmune antibodies associated with an autoimmune disease. The immuno globulin can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species, including human, murine, or rabbit origin.

Antibody fragments (AB fragments) comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), and epitope-binding fragments of any of the above which immuno-specifically bind to cancer cell antigens, viral antigens or microbial antigens, single-chain antibody molecules; multispecific antibodies formed from antibody fragments.

The linker, attaches the antibody or AB fragment or targeting moiety or label to the CA through covalent bond(s). The linker is a bifunctional or multifunctional moiety which can be used to link one or more drug moiety (D whereas D=CA) and an antibody unit (Ab) to form antibody-drug conjugates (ADC). The linker (L) may be stable outside a cell, i.e. extracellular, or it may be cleavable by enzymatic activity, hydrolysis, or other metabolic conditions. Antibody-drug conjugates (ADC) can be conveniently prepared using a linker having reactive functionality for binding to the drug moiety (here the CA) and to the antibody. Herein, the ADC is a CA linked to a targeting moiety. A linker can also include a spacer that might be of advantage to obtain favorable spacial distances between the linker, drug and targeting moieties.

A cysteine thiol, an amine, e.g. N-terminus or amino acid side chain such as lysine, or any other modification of the antibody (AB), as described below, can form a bond with a functional group of a linker reagent, drug moiety (D) or drug-linker reagent (D-L). The linkers are preferably stable extracellularly. Before transport or delivery into a cell, the antibody-drug conjugate (ADC) is preferably stable and remains intact, i.e. the antibody remains linked to the drug moiety. The linkers are stable outside the target cell and may be cleaved at some rate inside the cell. An effective linker will: (i) maintain the specific binding properties of the antibody; (ii) allow intracellular delivery of the conjugate or drug moiety; (iii) remain stable and intact, i.e. not cleaved, until the conjugate has been delivered or transported to its targeted site; and (iv) maintain a cytotoxic, cell-killing effect or a cytostatic effect of the CA. Stability of the ADC may be measured by standard analytical techniques such as mass spectroscopy, HPLC, and the separation/analysis technique LC/MS. Covalent attachment of the antibody and the CA requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known.

In another embodiment, the linker may be substituted with a sulfonate substituent or other substituents which may increase water solubility of the reagent and facilitate the coupling reaction of the linker reagent with the antibody or the CA, or facilitate the coupling reaction of AB-L with D, or D-L with AB, depending on the synthetic route employed to prepare the ADC. Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties, linker reagents and CA (=D) including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). US 2007/0092940 engineering antibodies by introduction of reactive cysteine amino acids.

Modified substrate means any amino acid and any related compound carrying at least one amino group and one carboxyl group that enable peptide bound formation of the modified substrate in a respective non-ribosomal peptide and which is naturally not incorporated into the non-ribosomal peptides synthesized by a specific cyanobacterial strain.

A modified amino acid or modified substrate may comprise an amino acid linker component including those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease. Amino acid side chains include those occurring naturally, as well as minor amino acids and non-naturally occurring amino acid analogs, such as citrulline.

BRIEF DESCRIPTION OF DRAWINGS

FIG. 7E shows the averaged mass spectrum of the peak visible in chromatogram (FIG 7D). The growth of strain CBT 959 could not be followed by measurement of optical density at 750 nm (OD750 nm) as the cell form aggregates making it impossible to measure reliable OD750 nm values.

FIG. 8E shows the averaged mass spectrum of the peak visible in chromatogram (FIG. 8D).

FIG. 10Eshows the averaged mass spectrum of the peak visible in chromatogram (FIG. 10D).

FIG. 12Eshows the averaged mass spectrum of the peak visible in chromatogram (FIG. 12D).

FIG. 14E shows the averaged mass spectrum of the peak visible in chromatogram (FIG. 14D).

FIG. 16E shows the averaged mass spectrum of the peak visible in chromatogram (FIG. 16D). The PDA-Signal of the novel Furyl-Ala variant of Microcystin LR is not visible due to the low concentration.

FIG. 18E shows the averaged mass spectrum of the peak visible in chromatogram (FIG. 18D).

FIG. 20E shows the averaged mass spectrum of the peak visible in chromatogram (FIG. 20D).

FIG. 22E 19e: Exemplary embodiment No. 9: Incorporation of the modified substrate Azido-Lys (Lys=Lysine) into Microcystin YR in position 4 produced by strain CBT 1. FIG. 22E shows the averaged mass spectrum of the peak visible in chromatogram (FIG. 22D). The PDA-Signal of the novel Azido-Lys (Lys=Lysine) variant of Microcystin YR is not visible due to overlapping peaks in the sample.

FIG. 24E shows the averaged mass spectrum of the peak visible in chromatogram (FIG. 24D).

FIG. 26E shows the averaged mass spectrum of the peak visible in chromatogram (FIG. 26D).

Detector signal intensities (y-Axis) are measured in milli-absorption units (mAU) and counts (dimensionless quantity) for PDA and mass spectrometry data respectively.

Figure 27A:
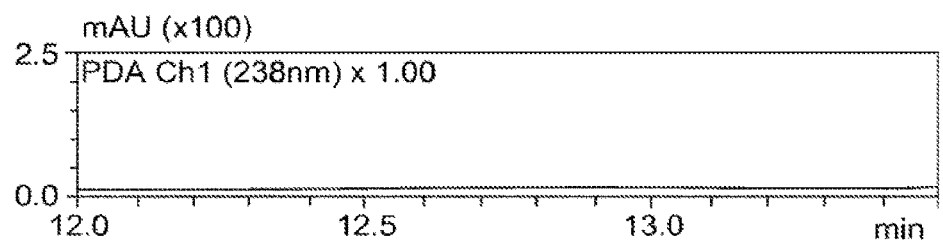
FIG. 27A: Exemplary embodiment No. 12: Incorporation of the modified substrate Azido-L-Phe (Phe=phenylalanine) into Microcystin YR in position 2 produced by strain CBT 480 in a large scale (2 l) cultivation system. HPLC-PDA Chromatogram at 238 nm for sample of control cultivation.
Figure 27B:
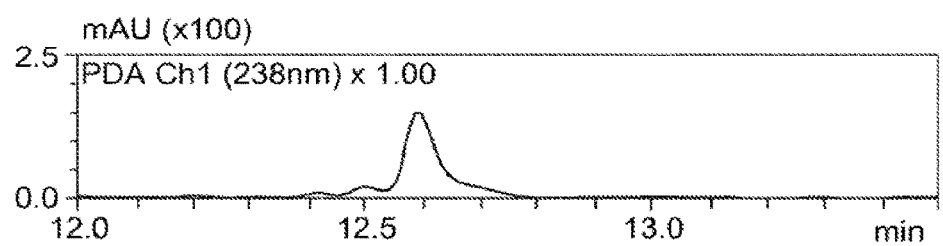

FIG. 27B: Exemplary embodiment No. 12: Incorporation of the modified substrate Azido-L-Phe (Phe=phenylalanine) into Microcystin YR in position 2 produced by strain CBT 480 in a large scale (2 l) cultivation system. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.

Figure 27C:
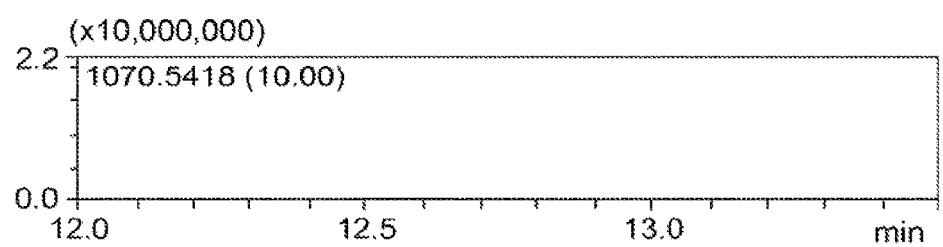

FIG. 27C: Exemplary embodiment No. 12: Incorporation of the modified substrate Azido-L-Phe (Phe=phenylalanine) into Microcystin YR in position 2 produced by strain CBT 480 in a large scale (2 l) cultivation system. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.

Figure 27D:
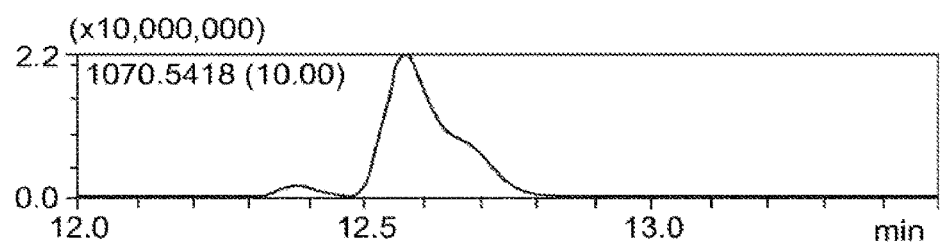

FIG. 27D: Exemplary embodiment No. 12: Incorporation of the modified substrate Azido-L-Phe (Phe=phenylalanine) into Microcystin YR in position 2 produced by strain CBT 480 in a large scale (2 l) cultivation system. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.

Figure 27E:
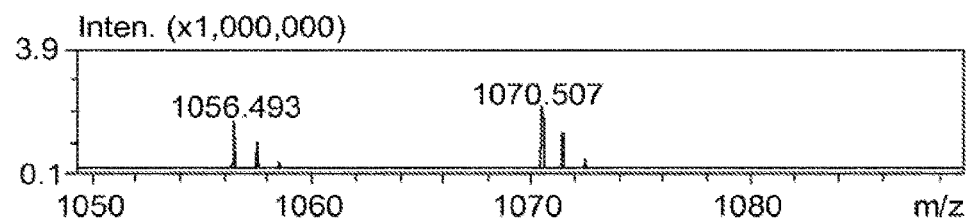

FIG. 27E: Exemplary embodiment No. 12: Incorporation of the modified substrate Azido-L-Phe (Phe=phenylalanine) into Microcystin YR in position 2 produced by strain CBT 480 in a large scale (2 l) cultivation system. FIG. 27E shows the averaged mass spectrum of the peak visible in chromatogram (FIG. 27D).

Figure 28:
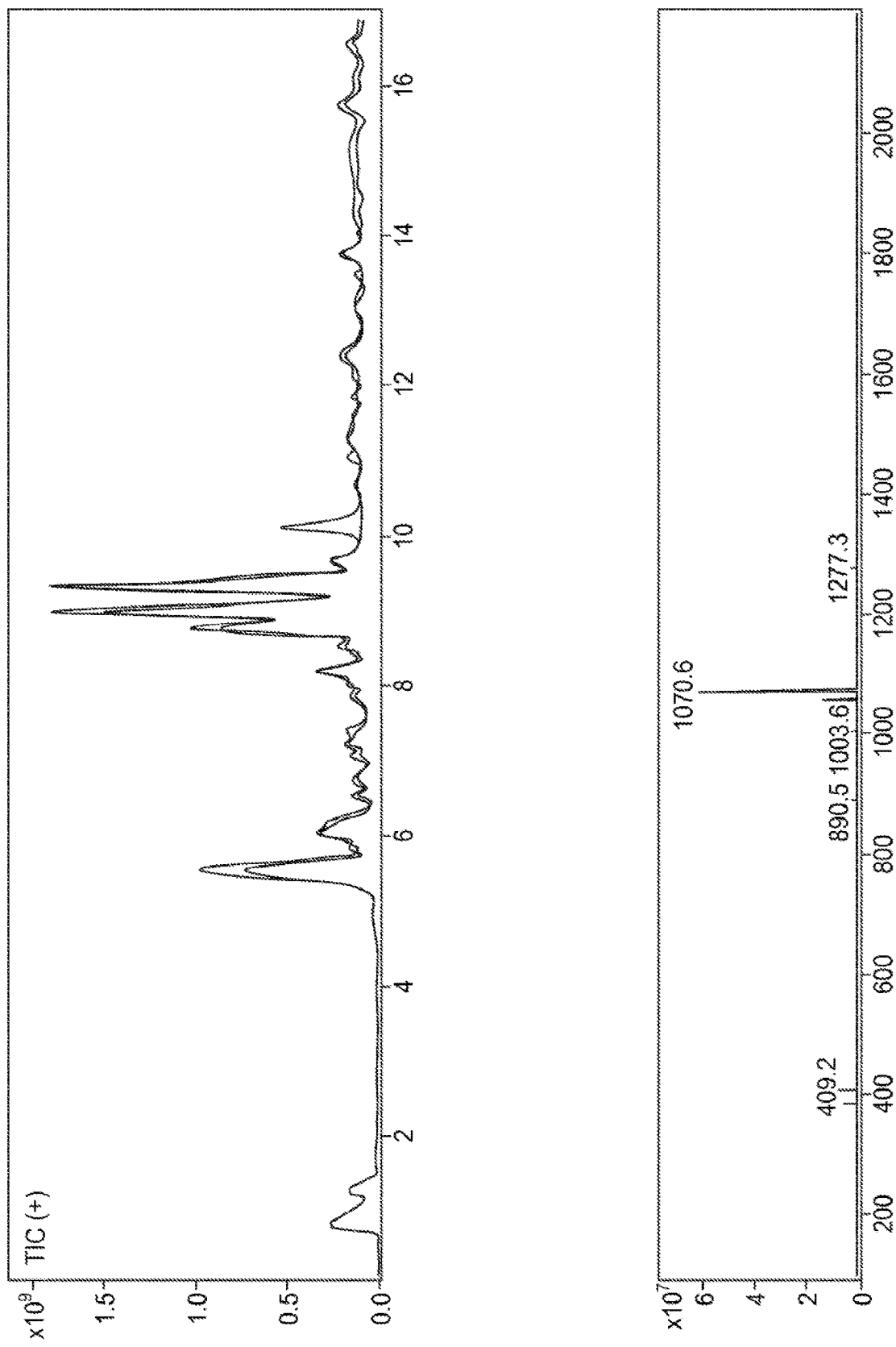

FIG. 28: Exemplary embodiment No. 13: Feeding of *Microcystis aeruginosa* strain CBT 480 with different amounts of modified substrate 4-azido-L-phenylalanine (0 µM, 10 µM, 30 µM) results an increasing amount of produced modified microcystin with increasing amount of fed modified substrate 4-azido-L-phenylalanine. This result allows for optimization of feeding protocols for respective productions of modified non-ribosomal peptides (here modified microcystins). The upper part of the figure shows overlaid HPLC-PDA Chromatograms at 238 nm for sample of control cultivation, sample of cultivation with added substrate 4-azido-L-phenylalanine of 10 µM in culture medium and sample of cultivation with added substrate 4-azido-L-phenylalanine of 30 µM in culture medium. The lower part of the figure shows the averaged mass spectrum of the newly formed peak visible at about 10 min in the HPLC chromatogram. Detector signal intensities (y-Axis) are measured in milli-absorption units (mAU) and counts (dimensionless quantity) for PDA and mass spectrometry data, respectively.

Figure 29A:
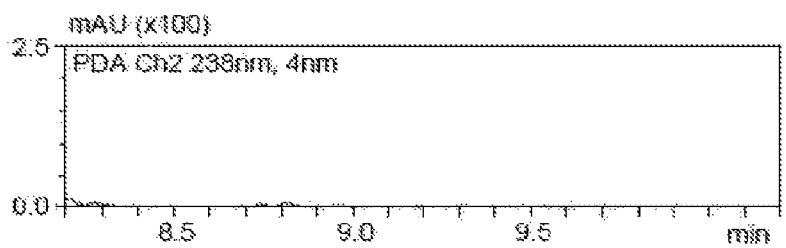

FIG. 29A: Exemplary embodiment No. 14: Incorporation of the modified substrate Prg-Tyr (Tyr=Tyrosine) into (D-Asp3, E-Dhb7) Microcystin-RR in position 2 produced by strain CBT 280. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.

Figure 29B:
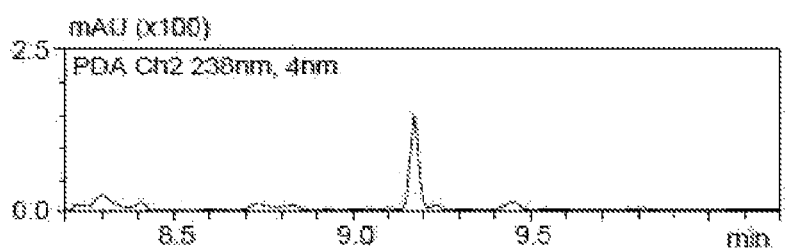

FIG. 29B: Exemplary embodiment No. 14: Incorporation of the modified substrate Prg-Tyr (Tyr=Tyrosine) into (D-Asp3, E-Dhb7) Microcystin-RR in position 2 produced by strain CBT 280. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.

Figure 29C:
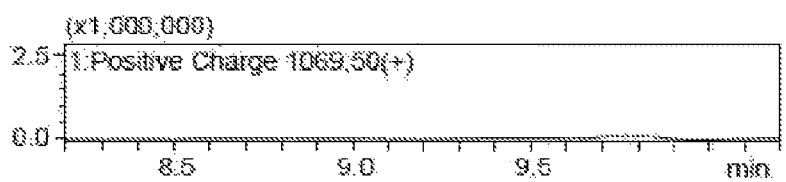

FIG. 29C: Exemplary embodiment No. 14: Incorporation of the modified substrate Prg-Tyr (Tyr=Tyrosine) into (D-Asp3, E-Dhb7) Microcystin-RR in position 2 produced by strain CBT 280. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.

Figure 29D:
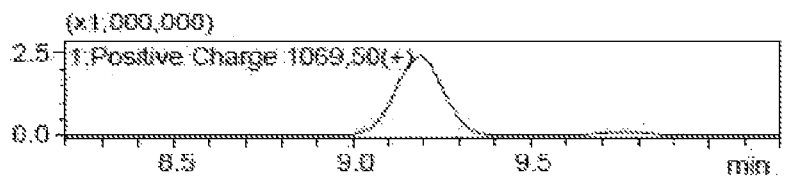

FIG. 29D: Exemplary embodiment No. 14: Incorporation of the modified substrate Prg-Tyr (Tyr=Tyrosine) into (D-Asp3, E-Dhb7) Microcystin-RR in position 2 produced by strain CBT 280. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.

Figure 29E:
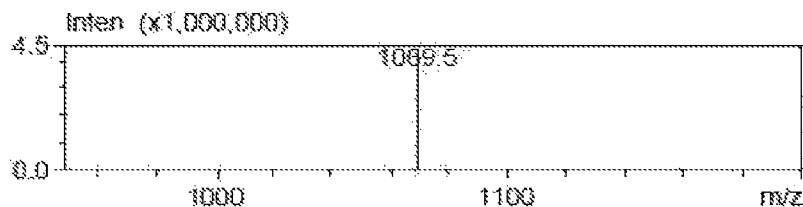

FIG. 29E: Exemplary embodiment No. 14: Incorporation of the modified substrate Prg-Tyr (Tyr=Tyrosine) into (D-Asp3, E-Dhb7) Microcystin-RR in position 2 produced by strain CBT 280. FIG. 29E shows the averaged mass spectrum of the peak visible in chromatogram (FIG. 29D).

Figure 30:
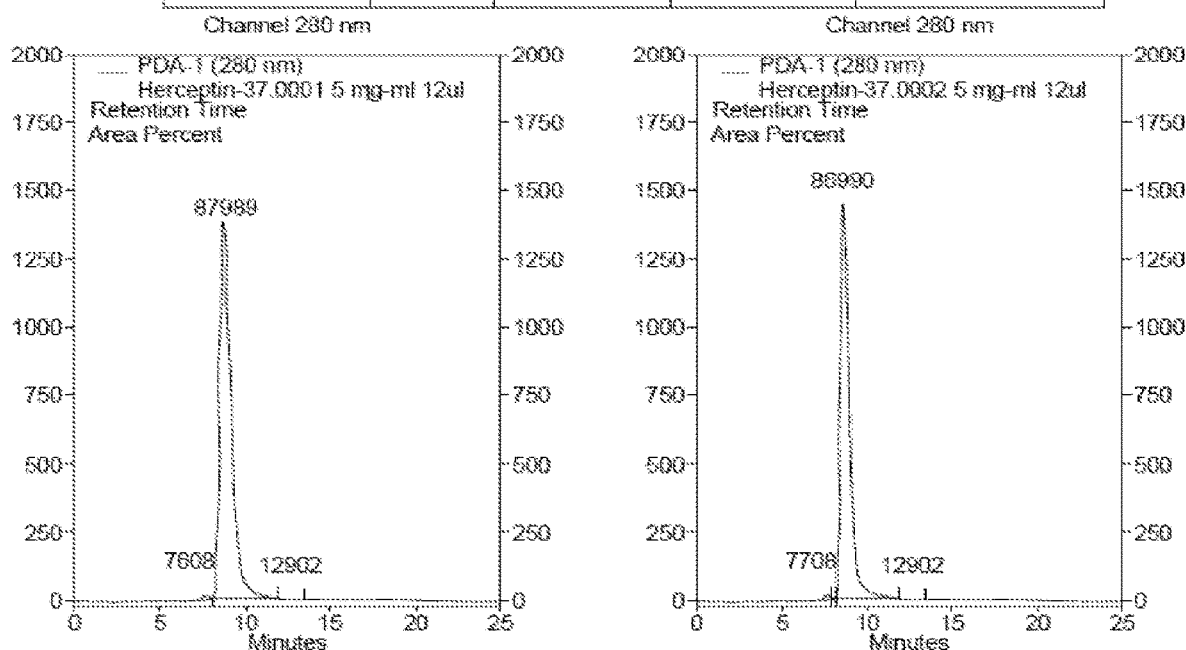

FIG. 30: Exemplary embodiment No. 20: Produced ADCs and results of analytical SEC-HPLC. In analytical SEC-HPLC the conjugates Microcystin-ADC1 and Microcystin-ADC2 showed a high level of purity with 98.9% and 99.0% monomers. In both cases, aggregates and small fragments were detected with rates of 0.8% and 0.2%.

Figure 31:
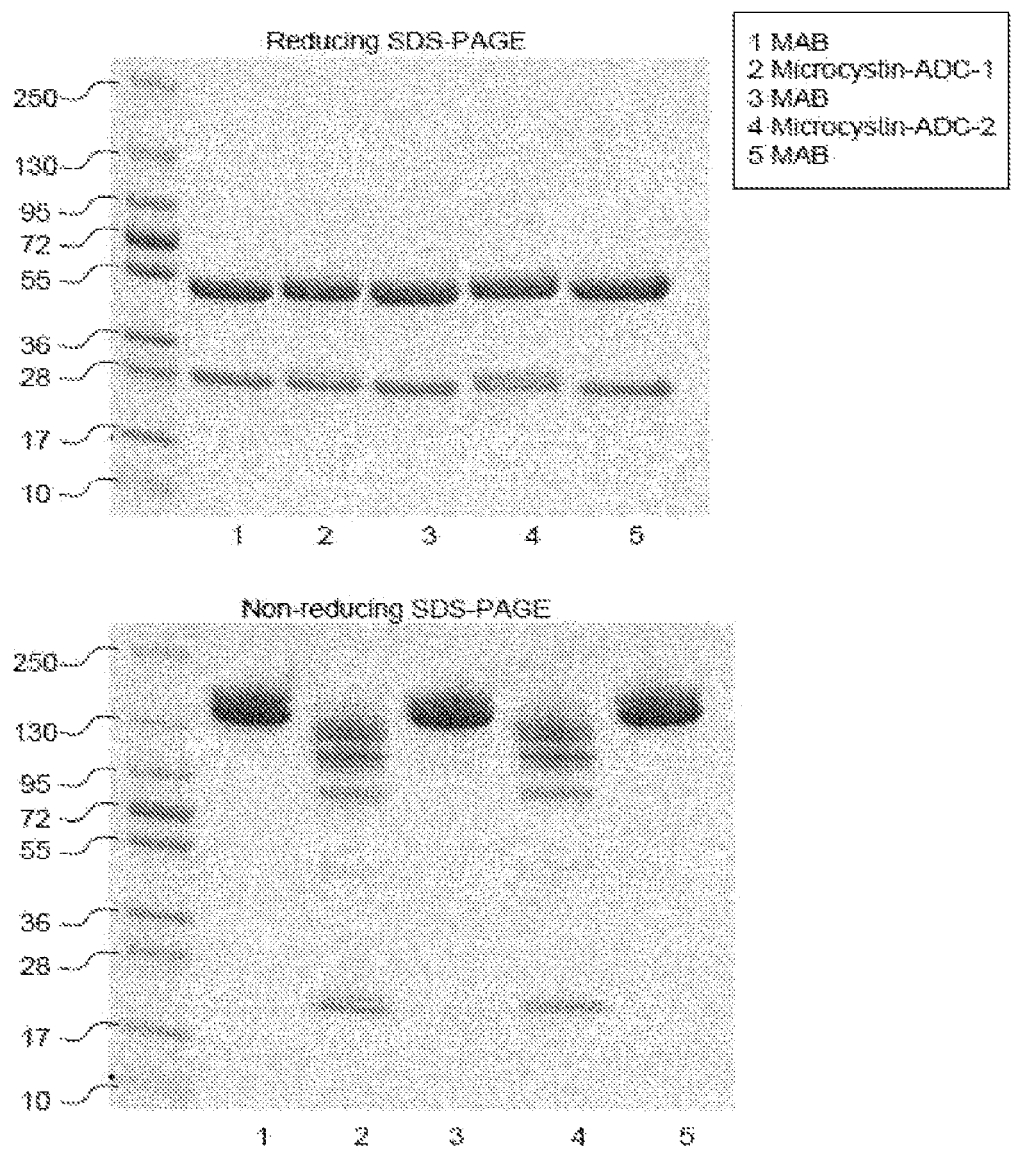

FIG. 31: Exemplary embodiment No. 21: Coomassie stained Gel electrophoresis gels demonstrating the binding of Microcystin variants 1 and 2 as payloads on monoclonal antibodies. In Coomassie staining under reducing conditions all samples showed a signal for the heavy chain at app. 50 kDa and the light chain at app. 25 kDa. All conjugates showed an up-shift of the protein signal of the heavy and the light chain compared to the naked MAB indicating toxin conjugation to both antibody chains. For all ADCs a double-signal was detected for the light chain indicating both, conjugated and unconjugated species. In Coomassie staining under non-reducing conditions the naked antibody showed a double signal at app. 150 kDa for the intact antibody. The ADCs showed a variety of signals between 25 kDa and 150 kDa, since in both cases the toxin was conjugated to reduced interchain disulfides leading to instability of the antibody during incubation at 37° C.

FIG. 32: Exemplary embodiment No. 22: Successful in vitro proof of concept of Microcystin-based ADCs. The cell viability is monitored in an in-vitro-assay with a cancer cell line for the different concentrations of the Microcystin ADC for two Microcystin variants as payloads. The ADC carries a non-cleavable linker. For Microcystin-ADC-2 an $EC_{50}$ values of 220 µM was determined. Differences between structural payload variants underline huge potential of further structural optimizations.

DETAILED DESCRIPTION OF THE INVENTION

The inventors for the first time have incorporated modified amino acids into microcystins which carry so called clickable anchor groups which allow the fast and easy binding of the entire molecule to e.g. peptide linker or other functional units like e.g. antibodies (see FIGS. 7A-13, and 18A-18E/19 or whereas the fed substrates carry functional groups that are easily accessible to additional modification towards clickable anchor groups (see FIGS. 14A-21).

It is shown that feeding of any combination of a clickable substrate with e.g. amino acids naturally occurring in microcystins and/or nodularins, modified versions of these amino acids or any other substrate might potentially lead to an incorporation of the fed substrate combinations into the non-ribosomal peptide (see FIGS. 18A-21).

The inventors show for the first time that a successfully fed substrate (e.g. the modified amino acid) is structurally not necessarily directly related to the substrate that is naturally incorporated into the microcystin or nodularin (e.g. the respective non-modified amino acid) (see FIGS. 10A-10E/11, 16A-16E/17, and 22A-25).

That means in the past successful feedings were only regarded to structural variants directly derived from the naturally (native) incorporated amino acid (e.g. o-methyl-tyrosine or chloro-tyrosine instead of tyrosine or homo-arginine instead of arginine). Considering the new results of the inventors it is obvious that the structural and functional diversity of non-ribosomal peptides generated by feeding significantly increases if also substrates can be used that are structurally not directly derived from the substrate which is naturally incorporated into the respective non-ribosomal peptide and which is also not a substitution of the naturally incorporated substrate with functional groups which are not directly accessible or transformable for use in conjugation chemistry incl. click chemistry, for the attachment of a targeting moiety or a label.

The invention relates to a modified microcystin and/or nodularin compound comprising at least one modified substrate, wherein the at least one modified substrate comprises an anchor group directly accessible or transformable for use in click chemistry, for the attachment of a targeting moiety and/or label or for additional structural modifications. This will allow for example connecting antibodies to the microcystins and nodularins and the creation of great compound libraries of microcystins and nodularins with novel structures.

In one embodiment of the invention, the one or more modified substrates are incorporated at a defined position of the microcystin and/or nodularin.

The CAs can carry an amino acid in the CA at a position where, in nature such an amino acid does not exist. The amino acid may be modified.

The inventors can astonishingly modify multiple positions other than the so-called variable positions 2 and 4 of microcystins or the respective Arg2 position in nodularins.

The invention further relates to a compound, wherein the one or more modified substrates are incorporated at any position of the microcystin other than Adda5 and DGlu6, which has the following general structure:

D-Alar-$X_2$-D-MeAsp$_3$-$Z_4$-Adda$_5$-DGlu$_6$-Mdha$_7$, SEQ ID NO: 1 and wherein $X_2$ and/or $Z_4$ are positions of preferred incorporation of said modified substrate.

In nodularin, the one or more modified substrates are incorporated at any position other than Adda$_3$ and DGlu$_4$, which has the following general structure:

D-MeAsp$_1$-Arg$_2$-Adda$_3$-DGlu$_4$-Mdhb$_5$, SEQ ID NO: 2.

and wherein Arg$_2$ is the position of preferred incorporation of said modified substrate.

Preferably, if the CA is microcystin, the modified position is $X_2$ or $Z_4$ and the modified substrate is a modified amino acid (see FIGS. 7A-17).

Also, preferably if the CA is microcystin, the modified position is $X_2$ and $Z_4$ and the modified substrate is a modified amino acid (see FIGS. 18A-21).

In nodularin, preferably, the modified position is Arg$_2$ and the modified substrate is a modified amino acid.

The modified substrate, preferably modified amino acid, preferably contains an anchor group directly accessible or transformable for use in conjugation chemistry (incl. click chemistry), for the attachment of a targeting moiety or a label or for additional structural modifications (see FIGS. 7A-25).

In the method according to the invention, the conjugation chemistry reaction (incl. click chemistry reaction) of the clickable substrate is selected from reactions comprising copper(I)-catalyzed azide-alkyne cycloaddition, strain promoted azide-alkyne cycloaddition, alkyne-azide cycloaddition, or alkyne-tetrazine inverse-demand Diels-Alder reaction. Additional conjugation chemistry can be selected from reactions exploiting the specific reactivities of primary amines, thiols, aldehydes, carboxyls, and oximes. Therefore, the anchor group of at least one modified substrate which is directly accessible for use in conjugation chemistry (incl. click chemistry), for the attachment of a targeting moiety can be selected from the group of:

- Azido groups that can subsequently be modified e.g. by reaction with alkynes, activated alkenes, or phosphines, whereas the azido group of the cytotoxin reacts with the respective functional group of a linker, antibody, or other functional molecule such as a fluorescent dye or polymer matrix.
- Alkyne (e.g. propargyl or diaryl-strained cyclooctyne) groups that can subsequently be modified e.g. by reaction with azides, whereas the alkyne group of the cytotoxin reacts with the respective functional group of a linker, antibody, or other functional molecule such as a fluorescent dye or polymer matrix.
- Tetrazines that can subsequently be modified e.g. by reaction with alkynes or alkenes, whereas the tetrazine group of the cytotoxin reacts with the respective functional group of a linker, antibody, or other functional molecule such as a fluorescent dye or polymer matrix.
- Primary amines that can subsequently be modified e.g. by reaction with isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, phosphines, or fluorophenyl esters, whereas the amino group of the cytotoxin reacts with the respective functional group of a linker, antibody, or other functional molecule such as a fluorescent dye or polymer matrix.
- Thiols that can subsequently be modified e.g. by reaction with maleimides, haloacetyls, pyridyldisulfides, thiosulfonares or vinylsulfones, whereas the thiol group of the cytotoxin reacts with the respective functional group of a linker, antibody, or other functional molecule such as a fluorescent dye or polymer matrix.

Aldehydes that can subsequently be modified e.g. by reaction with amines, aminothiols, Ellman's Reagent, alkoxyamines, hydrazides or thiols, whereas the aldehyde group of the cytotoxin reacts with the respective functional group of a linker, antibody, or other functional molecule such as a fluorescent dye or polymer matrix.

Carboxyls that can subsequently be modified e.g. by reaction with carbodiimides, whereas the cyrboxy group of the cytotoxin reacts with the respective functional group of a linker, antibody, or other functional molecule such as a fluorescent dye or polymer matrix.

Oximes that can subsequently be modified e.g. by reaction with acetophenones such as p-acetylphenylalanine, whereas the oxime group of the cytotoxin reacts with the respective functional group of a linker, antibody, or other functional molecule such as a fluorescent dye or polymer matrix.

Also claimed is the introduction of at least one modified substrate with a functional group that is directly transformable for use in conjugation chemistry (incl. click chemistry) for the attachment of a targeting moiety. One examples for this is the introduction of a substrate containing a nitro group that can be reduced to yield a primary amino group, which, as described above, can be used for conjugation chemistry (incl. click chemistry). Another example is the introduction of a substrate containing a furanyl that can subsequently be modified e.g. by photoreaction with nucleophiles such as hydrazines, whereas the furanyl group reacts after activation to an unsaturated dicarbonyl residue with the respective nucleophilic functional group of a targeting moiety like a linker, antibody, or other functional molecule such as a fluorescent dye or a polymer matrix (see FIGS. 14A-21).

Tyrosine containing microcystins can also be functionalized using 4-phenyl-3H-1,2,4-triazoline-3,5(4H)-diones (PTADs) to introduce additional conjugation chemistry (inc. click chemistry) amenable functional groups as described above.

Ideally, modified amino acids which are directly accessible or transformable for use in conjugation chemistry (inc. click chemistry), is selected from the group of the following table (see FIGS. 7A-25 and tables 1 to 4 for respective execution examples):

| Systematic name | CAS Number | Short name | Supplier | Order number |
| --- | --- | --- | --- | --- |
| (2S)-2-amino-3-azidopropanoic acid hydrochloride | 105661-40-3 | Azido-L-Ala | Iris Biotech GmbH | HAA1880 |
| (2S)-2-amino-6-azidohexanoic acid hydrochloride | 159610-92-1 | Azido-Lys | Iris Biotech GmbH | HAA1625 |
| (S)-2-Amino-5-azidopentanoic acid hydrochloride | 156463-09-1 | Azido-Norval | Iris Biotech GmbH | HAA1620 |
| (2S)-2-amino-3-(4-prop-2-ynoxyphenyl)propanoic acid hydrochloride | 610794-20-2 | Prg-Tyr | Iris Biotech GmbH | HAA1971 |
| (2S)-2-amino-5-(N'-nitrocarbamimidamido)pentanoic acid | 2149-70-4 | Nitro-Arg | Sigma-Aldrich Chemie GmbH | 2149-70-4 |
| (2S)-2-amino-3-(furan-2-yl)propanoic acid | 127682-08-0 | Furyl-Ala | Iris Biotech GmbH | HAA2930 |
| (S)-Amino-6-((prop-2-ynyloxy)carbonylamino)hexanoic acid hydrochloride | 1428330-91-9 | Lys(Poc) | Iris Biotech GmbH | HAA2090 |
| (2S)-2-Amino-3-(4-azidophenyl)propanoic acid | 33173-53-4 | Azido-L-Phe | Iris Biotech GmbH | HAA1850 |
| L-α-Amino-ε-guanidinohexanoic acid | 156-86-5 | H-homo-Arg-OH | Bachem | 4016423 |

The invention relates to a compound, wherein the microcystin has one of the following formula:

D-Ala-$X_2$-D-MeAsp$_3$-$Z_4$-Adda$_5$-DGlu$_6$-Mdha$_7$,

| Position | 1 | 2 | 3 | 4 | 5 | 6 | 7 |
| --- | --- | --- | --- | --- | --- | --- | --- |
| Possible amino acids | Ala$_1$ D-Ala D-Ser D-Leu | $X_2$ variable | D-MeASp$_3$ D-MeAsp A-Asp | $Z_4$ variable | Adda$_5$ Adda DM-Adda (6Z)Adda ADM-Adda | DGlu$_6$ D-Glu D-Glu(OCH$_3$) | Mdha$_7$ Mdha Dha L-Ser L-MeSer Dhb MeLan | wherein

| Ala$_1$ | X$_2$ | D-MeAsp$_3$ | Z$_4$ | Mdha$_7$ |
|---|---|---|---|---| comprise the position of the incorporation of one or more modified substrates, wherein preferably the modified substrate which are directly accessible or transformable for use in conjugation (click) chemistry is an amino acid selected from the group of:

| Systematic name | CAS Number | Short name | Supplier | Order number |
|---|---|---|---|---|
| (2S)-2-amino-3-azidopropanoic acid hydrochloride | 105661-40-3 | Azido-L-Ala | Iris Biotech GmbH | HAA1880 |
| (2S)-2-amino-6-azidohexanoic acid hydrochloride | 159610-92-1 | Azido-Lys | Iris Biotech GmbH | HAA1625 |
| (S)-2-Amino-5-azidopentanoic acid hydrochloride | 156463-09-1 | Azido-Norval | Iris Biotech GmbH | HAA1620 |
| (2S)-2-amino-3-(4-prop-2-ynyloxyphenyl)propanoic acid hydrochloride | 610794-20-2 | Prg-Tyr | Iris Biotech GmbH | HAA1971 |
| (2S)-2-amino-5-(N'-nitrocarbamimidamido)pentanoic acid | 2149-70-4 | Nitro-Arg | Sigma-Aldrich Chemie GmbH | 2149-70-4 |
| (2S)-2-amino-3-(furan-2-yl)propanoic acid | 127682-08-0 | Furyl-Ala | Iris Biotech GmbH | HAA2930 |
| (S)-Amino-6-((prop-2-ynyloxy)carbonylamino)hexanoic acid hydrochloride | 1428330-91-9 | Lys(Poc) | Iris Biotech GmbH | HAA2090 |
| (2S)-2-Amino-3-(4-azidophenyl)propanoic acid | 33173-53-4 | Azido-L-Phe | Iris Biotech GmbH | HAA1850 |
| L-α-Amino-ε-guanidinohexanoic acid | 156-86-5 | H-homo-Arg-OH | Bachem | 4016423 |

The invention also relates to a compound, wherein the nodularin has one of the following formula:

| | Position | | | | |
|---|---|---|---|---|---|
| | 1 | 2 | 3 | 4 | 5 |
| Possible amino acid | MeAsp$_1$ D-MeAsp D-Asp | Arg$_2$ Homo-Arg | Adda$_3$ Adda DM-Adda (6Z)Adda Me-Adda | DGlu$_4$ D-Glu D-Glu(OCH$_3$) | Mdhb$_5$ Mdhb Dhb | wherein

Ideally, the nodularin is modified at the $Arg_2$ position.

In the method according to the invention, the conjugation chemistry reaction (incl. click chemistry reaction) of the clickable substrate is selected from the group comprising copper(I)-catalyzed azide-alkyne cycloaddition, strain-promoted azide-alkyne cycloaddition, alkyne-azide cycloaddition, or alkyne-tetrazine inverse-demand Diels-Alder reaction. Additional conjugation chemistry can be selected from reactions exploiting the specific reactivities of primary amines, thiols, aldehydes, carboxyls, and oximes.

In the method according to the invention, the at least one modified amino acid comprises an anchor group directly accessible or transformable for use in conjugation chemistry (incl. click chemistry), for the attachment of a targeting moiety and/or a label via a linker or w/o a linker between the modified amino acid and the targeting moiety and/or a label.

However, regarding the modification of the CA of microcystins and nodularins by the introduction of modified substrates most preferred are the genera *Microcystis, Planktothrix, Oscillatoria, Nostoc, Anabaena, Aphanizomenon, Hapalosiphon, Nodularia*.

In one embodiment of the invention the targeting moiety (TM) is selected form the group of antibody, antibody fragment, fab fragment, modified antibody, fluorophores, and chromatographic columns. Concerning the targeting moiety, in one embodiment, the ADC specifically binds to a receptor encoded by an ErbB gene. The TM may bind specifically to an ErbB receptor selected from EGFR, HER2, HER3 and HER4. The ADC may specifically bind to the extracellular domain (ECD) of the HER2 receptor and inhibit the growth of tumor cells which overexpress HER2 receptor (see FIG. 32). The antibody of the ADC may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (trastuzumab). The antibody may be an antibody fragment, e.g. a Fab fragment.

According to the invention, the compound can be used as a medicament. Furthermore, it can be used as a medicament for the diagnosis or treatment of cancer and/or other diseases and disorders.

The ADC of the invention may be useful in the treatment of cancer including, but are not limited to, antibodies against cell surface receptors and tumor-associated antigens (TAA). Such tumor-associated antigens are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via targeted antibody-based therapies.

Examples of TAA include, but are not limited to, Tumor-Associated Antigens listed below. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 3A:
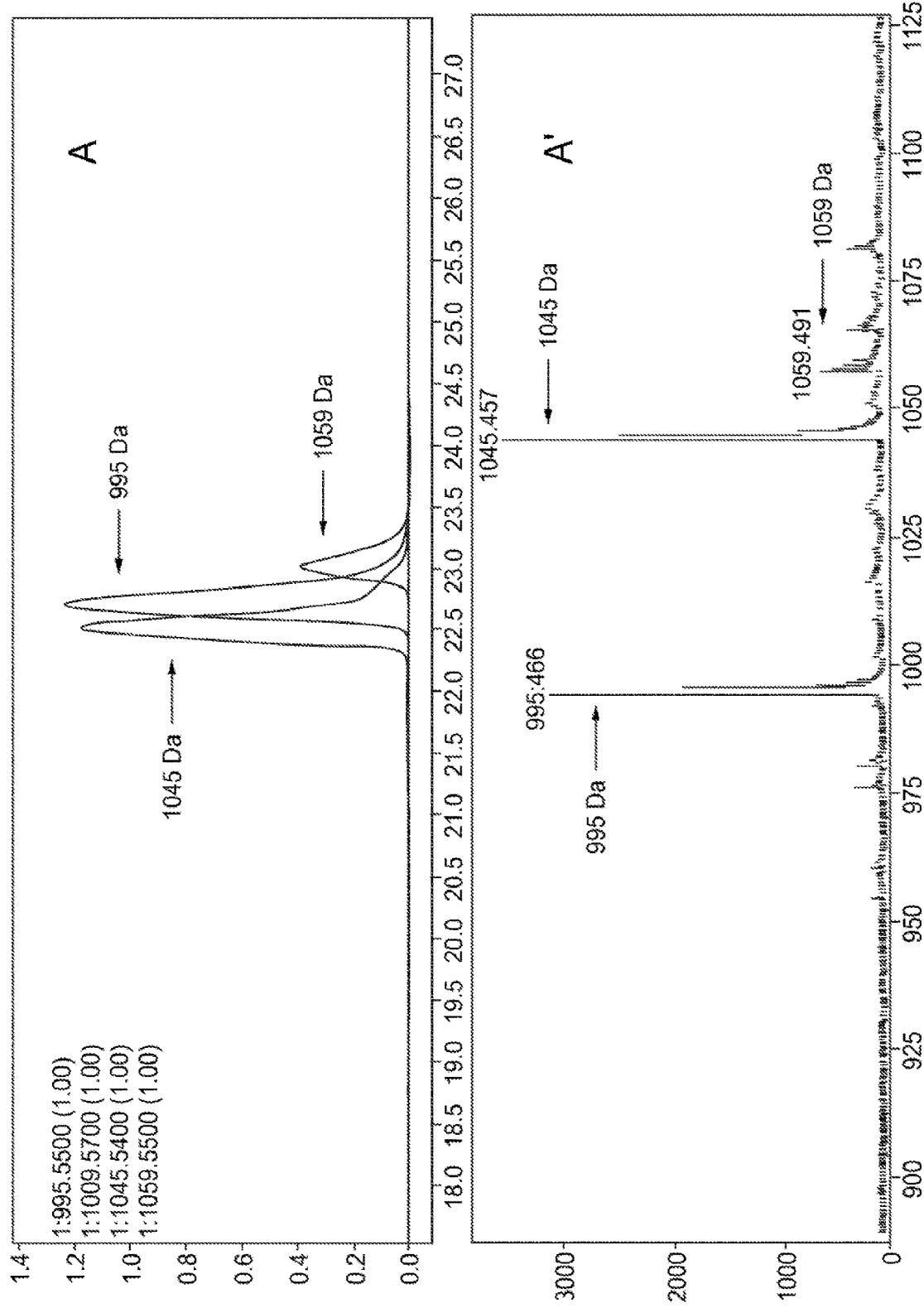
FIG. 3A: Detection of modified microcystins by two different mass spectrometry method after feeding of modified substrates to a *Microcystis aeruginosa* strain CBT 480 in a 6 ml scale (top panel: detection with ESI-IT-ToF-MS; bottom panel: detection with MALDI-ToF-MS); A, A': CBT 480 culture fed with O-methyltyrosine; Molecule masses of naturally produced microcystins: 995 Da=MC-LR, 1045 Da=MC-YR; Molecule masses of modified microcystins generated by feeding with O-methyltyrosine (OMetY) and homoarginine (hR): 1059 Da=MC-OMetYR or MC-YhR; 1009 Da=MC-LhR.
Figure 3B:
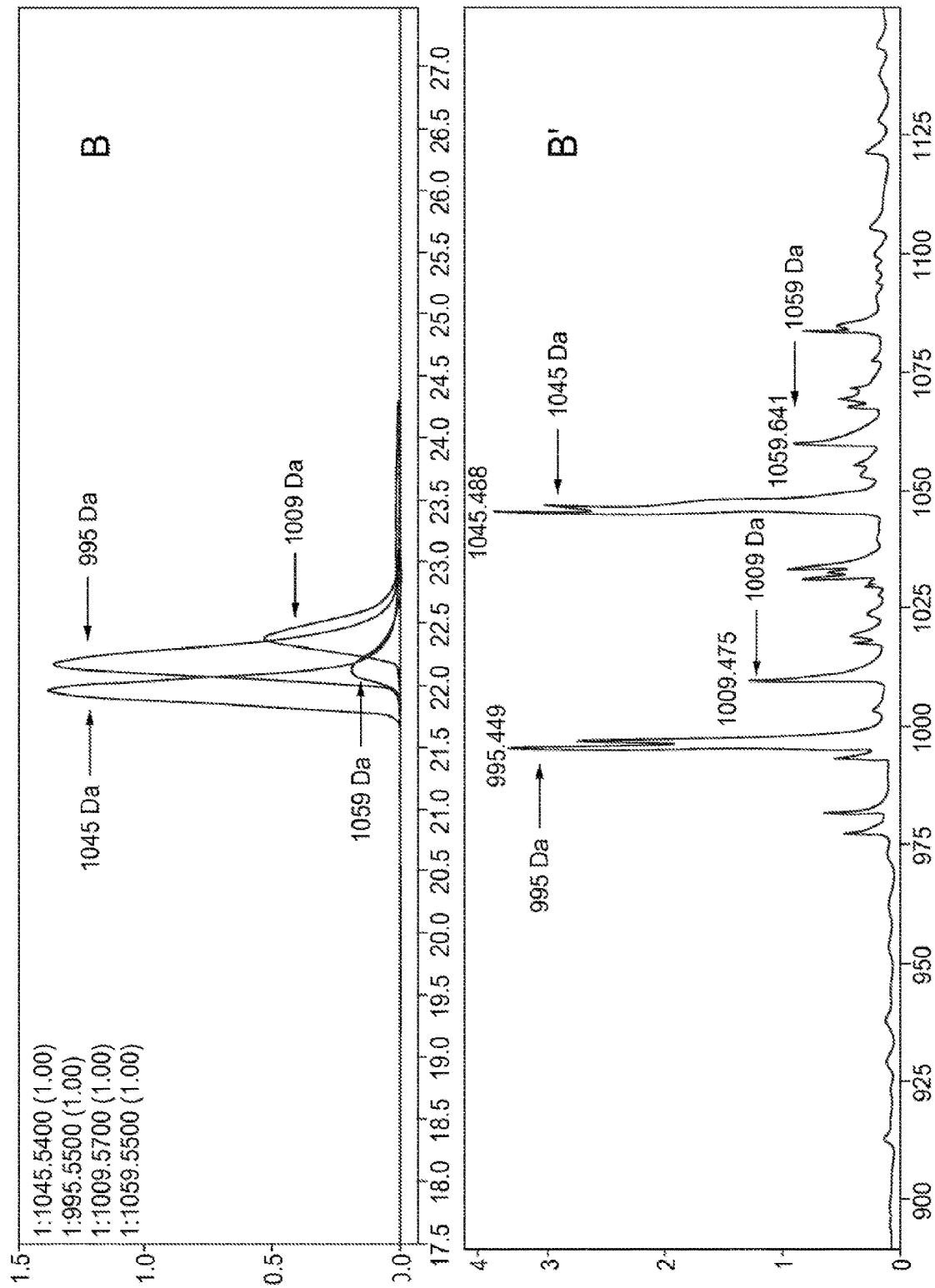
FIG. 3B: Detection of modified microcystins by two different mass spectrometry method after feeding of modified substrates to a Microcystis aeruginosa str cystin are indicated by big and bold white letters. These amino acids form the active pocket of the A domains and the sequence in their one-letter amino acid code represent the so called specificity-conferring code of A domains which shall allow for the prediction of substrate specificity of A domains. The only difference in the amino acid sequence of McyB1 of both strains is in amino acid position 672. Only one of nine pocket-forming amino acids of the A domains of both strains is different between the strains and also the remaining parts of the A domain as well as of the whole biosynthetic gene clusters are almost identical between the strains leading to the conclusion that the incorporation of leucine and tyrosine at position 2 of the microcystin in the strain CBT 480 is a strain-specific feature but cannot be explained by differences in the DNA sequence of the biosynthetic gene clusters and amino acid sequence of the microcystin synthetases, resp. The consensus sequence as between the "Query" and "Sbjct" sequences is indicated by "Consensus" and corresponds to SEQ ID NO: 6. Each letter in the consensus sequence is an identical match. The blank spaces in the consensus sequence are where the match indicated a zero or negative score. The "+" symbol in the consensus sequence represents a conservative substitution. The "Query" sequence shown corresponds to SEQ ID NO: 4 and the "Sbjct" sequence shown corresponds to SEQ ID NO: 5.
Figure 4E:
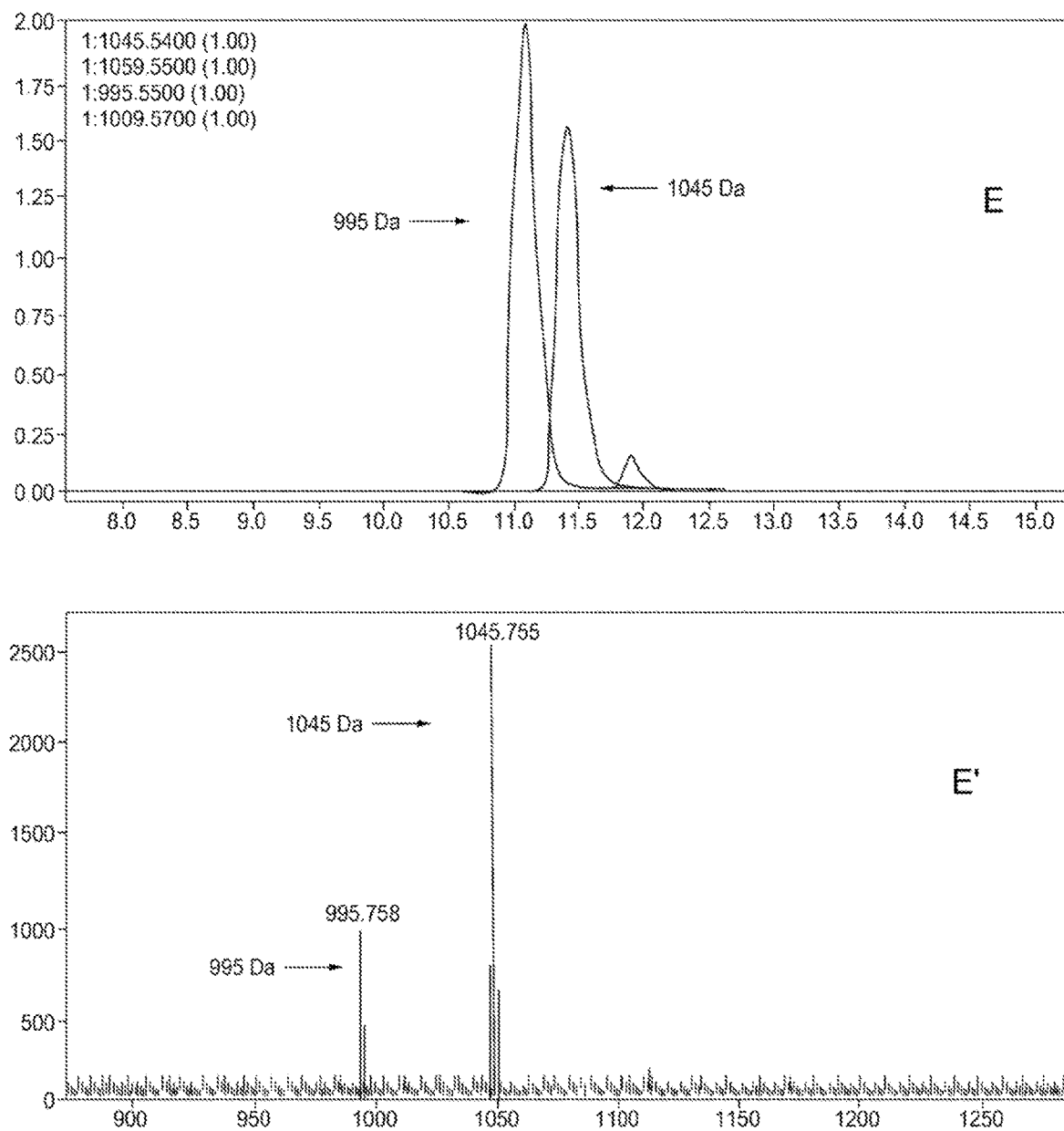
Figure 5C:
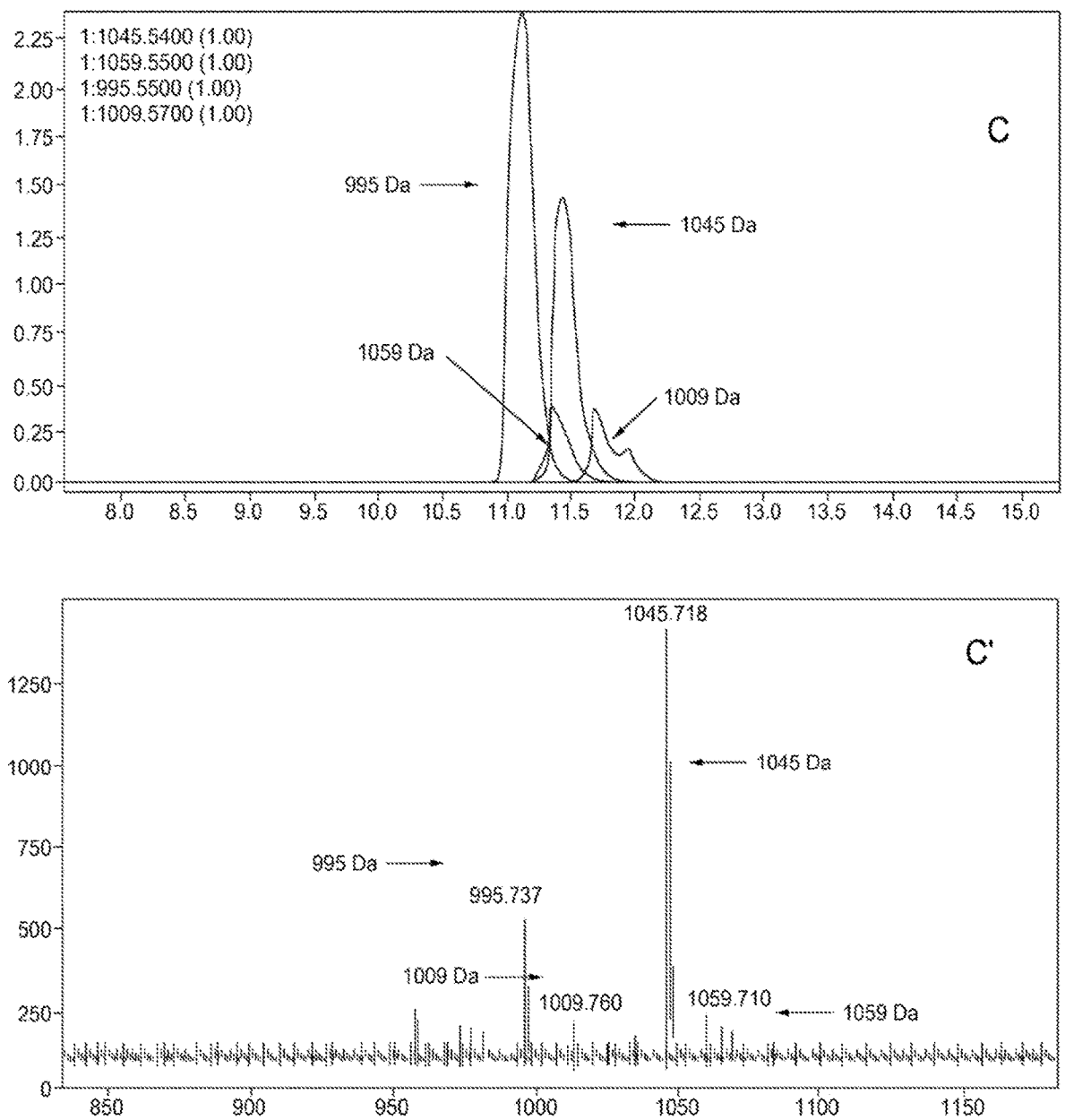

BMPR1B (bone morphogenetic protein receptor-type IB, Genbank accession no. NM-001203);

E16 (LAT1, SLC7A5, Genbank accession no. NM-003486);

STEAP1 (six transmembrane epithelial antigen of prostate, Genbank accession no. NM-012449);

0772P (CA125, MUC16, Genbank accession no. AF361486);

MPF (MPF, MSLN, SMR, megakaryocyte potentiating factor, mesothelin, Genbank accession no. NM-005823);

Napi3b (NAPI-3B, NPTIIb, SLC34A2, solute carrier family 34 (sodium phosphate), member 2, type II sodium-dependent phosphate transporter 3b, Genbank accession no. NM-006424);

Sema 5b (F1110372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878);

PSCA hlg (2700050C12Rik, C530008016Rik, RIKEN cDNA 2700050C12, RIKEN cDNA 2700050C12 gene, Genbank accession no. AY358628);

ETBR (Endothelin type B receptor, Genbank accession no. AY275463);

MSG783 (RNF124, hypothetical protein F1120315, Genbank accession no. NM-017763);

STEAP2 (HGNC-8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138);

TrpM4 (BR22450, F1120041, TRPM4, TRPM4B, transient receptor potential cation channel, subfamily M, member 4, Genbank accession no. NM-017636);

CRIPTO (CR, CR1, CRGF, CRIPTO, TDGF1, teratocarcinoma-derived growth factor, Genbank accession no. NP-003203 or NM-003212);

CD21 (CR2 (Complement receptor 2) or C3DR(C3d/Epstein Barr virus receptor) or Hs.73792 Genbank accession no. M26004);

CD79b (CD79B, CD79β, IGb (immunoglobulin-associated beta), B29, Genbank accession no. NM-000626 or 11038674);

FcRH2 (IFGP4, IRTA4, SPAP1A (SH2 domain containing phosphatase anchor protein 1a), SPAP1B, SPAP1C, Genbank accession no. NM-030764, AY358130);

HER2 (ErbB2, Genbank accession no. M11730); Coussens L., et al Science (1985) 230(4730):1132-1139);

NCA (CEACAM6, Genbank accession no. M18728); Barnett T., et al Genomics 3, 59-66, 1988;

MDP (DPEP1, Genbank accession no. BC017023);

IL20Rα (IL20Ra, ZCYTOR7, Genbank accession no. AF184971);

Brevican (BCAN, BEHAB, Genbank accession no. AF229053);

EphB2R (DRT, ERK, HekS, EPHT3, Tyro5, Genbank accession no. NM-004442);

ASLG659 (B7h, Genbank accession no. AX092328); US20040101899 (Claim 2);

PSCA (Prostate stem cell antigen precursor, Genbank accession no. AJ297436);

GEDA (Genbank accession No. AY260763); AAP14954 lipoma HMGIC fusion-partner-like protein/pid=AAP14954.1 *Homo sapiens* (human);

(26) BAFF-R (B cell-activating factor receptor, BLyS receptor 3, BR3, Genbank accession No. AF116456); BAFF receptor/pid=NP-443177.1-*Homo sapiens*; Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3); Cross-references: MIM:606269; NP-443177.1; NM-052945-1; AF132600

CD22 (B-cell receptor CD22-B isoform, BL-CAM, Lyb-8, Lyb8, SIGLEC-2, FLJ22814, Genbank accession No. AK026467);

CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation);

CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia);

HLA-DOB (Beta subunit of MHC class II molecule (Ia antigen) that binds peptides and presents them to CD4+ T lymphocytes);

P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability);

CD72 (B-cell differentiation antigen CD72, Lyb-2); 359 aa, pI: 8.66, MW: 40225 TM: 1 [P] Gene Chromosome: 9p13.3, Genbank accession No. NP-001773.1); LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis);

FcRH1 (Fc receptor-like protein 1, a putative receptor for the immunoglobulin Fc domain that contains C2 type Ig-like and ITAM domains, may have a role in B-lymphocyte differentiation);

IRTA2 (FcRHS, Immunoglobulin superfamily receptor translocation associated 2, a putative immunoreceptor with possible roles in B cell development and lymphomagenesis;

TENB2 (TMEFF2, tomoregulin, TPEF, HPP1, TR, putative transmembrane proteoglycan, related to the EGF/heregulin family of growth factors and follistatin);

MUC1 (Tumor-associated MUC1 glycopeptide epitopes); Human adenocarcinomas overexpress a hypoglycosylated, tumor-associated form of the mucin-like glycoprotein MUC1 containing abnormal mono- and disaccharide antigens, such as Tn, sialyl-Tn, and TF, as well as stretches of unglycosylated protein backbone in the variable number of tandem repeats (VNTR) region.

The ADC which can be produced based on the present invention may be used to treat various diseases or disorders in a patient, such as cancer and autoimmune conditions including those characterized by the overexpression of a disease-associated antigen, including but not limited to tumor-associated antigen. Exemplary conditions or disorders include infection diseases and others and specifically benign or malignant tumors; leukemia and lymphoid malignancies; other disorders such as neuronal, glial, astrocytal, hypothalamic, glandular, macrophagal, epithelial, stromal, blastocoelic, inflammatory, angiogenic and immunologic disorders. Cancer types susceptible to ADC treatment include those which are characterized by the overexpression of certain tumor associated antigens or cell surface receptors, e.g. HER2.

One method is for the treatment of cancer in a mammal, wherein the cancer is characterized by the overexpression of an ErbB receptor. The mammal optionally does not respond, or responds poorly, to treatment with an unconjugated anti-ErbB antibody. The method comprises administering to the mammal a therapeutically effective amount of an antibody-drug conjugate compound. The growth of tumor cells that overexpress a growth factor receptor such as HER2 receptor or EGF receptor may be inhibited by administering to a patient an ADC according to the invention which binds specifically to said growth factor receptor and a chemotherapeutic agent wherein said antibody-drug conjugate and said chemotherapeutic agent are each administered in amounts effective to inhibit growth of tumor cells in the patient (see FIG. 32).

Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, gastrointestinal stromal tumor (GIST), pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A further embodiment of the invention is a microcystin and/or nodularin compound, comprising one or more modified substrates, wherein the one or more modified substrate is not directly derived from the naturally incorporated substrate, such as preferably an amino acid or a modified amino acid which is, in nature, not incorporated at the specific position in said non-ribosomal peptide and which is also not a substitution of the naturally incorporated substrate with functional groups which are not directly accessible or transformable for use in conjugation chemistry incl. click chemistry, for the attachment of a targeting moiety or a label.

Examples

Successful feedings of modified substrates were performed in different cultivation systems and scales allowing for screening (small scales of up to 10 ml; see FIGS. 2A-5E) and for production (2-20 L scales; see FIGS. 27A-27E and 28) of modified non-ribosomal peptides. The different screening scales comprise: 1.6 ml cultures cultivated in ca. 2.2 ml deep-well microtiter plates (dw-MTP) whereas $CO_2$ supply was assured by intense shaking of 600 rpm and a constant $CO_2$ concentration of 5% in the head space above the dw-MTP. Illumination occurred via LED panel or vial fluorescence bulbs for 24 hours a day. Light intensity was adjusted in dependence of the strain and its growth phase between 35-250 µmol/s*m². The temperature was strain-specific varied between 20° C. and 30° C.

A cultivation according to the method is thus preferred wherein the shaking is between 400-800 rpm and a constant $CO_2$ concentration of 1 to 10% in the head space, preferably 3 to 8% in the head space.

10 ml cultures cultivated in 40 ml polystyrene tubes whereas $CO_2$ supply was assured by intense shaking of 250-350 rpm and a constant $CO_2$ concentration of 5% below the culture vessel. Hereby $CO_2$ got introduced into the culture via a $CO_2$ permeable polypropylene membrane on the bottom of the culture vessels. Illumination occurred via fluorescence bulbs for 24 hours a day and light intensity was again adjusted in dependence of the strain and its growth phase between 35-250 µmol/s*m². The temperature was again strain-specific varied between 20° C. and 30° C.

A cultivation according to the method is thus preferred wherein the illumination occurred via fluorescence bulbs for 24 hours a day and is between 20-450 µmol/s*m².

50 ml cultures cultivated in glass flasks whereas $CO_2$ supply was assured by bubbling with constant $CO_2$ concentration of 5%. The cultures were mixed via stirring with a magnetic stir bar at 100 rpm. Illumination occurred via fluorescence bulbs for 24 hours a day and intensity was adjusted in dependence of strain and growth phase between 35-250 µmol/s*m².

In addition, feeding experiments were also performed in a production scale between 2 L and 20 L whereas $CO_2$ supply and mixing was assured by bubbling with constant $CO_2$ concentration of 0.5-5.0%. Illumination occurred via fluorescence bulbs and intensity was adjusted in dependence of strain and growth phase between 35-250 µmol/s*m².

Optionally, the cultivations were performed under day-night-cycles of 16 hours light/8 hours at the same light intensities during the day period as described above.

Optionally, the cultivations were performed with different light sources (e.g. LED lights or sulfur-plasma lamps) and using strain-specific variations of light intensity, $CO_2$ concentration, shaking/stirring intensity and media composition.

Exemplary feeding scheme for the 10 ml scale:

All strains were cultivated in BG11 medium (see below), according to strain-specific cultivation conditions determined before.

Cells were pre-cultivated in Erlenmeyer flasks under low light conditions (30 µmol/s*m2) for 4 days at 25° C. and on a shaker at 70 rpm.

For the feeding experiment in the 10 ml scale, the cells were inoculated at optical density at 750 nm (OD750 nm) of 0.5 in ca. 40 ml polystyrene tubes. The medium was buffered by addition of TES to a concentration of 10 mM in the medium. Optionally DMSO was added to a concentration of 1% in the medium.

The feeding of cultures started at inoculation by adding the respective modified substrate(s) to a concentration of 10 mM in the medium. Daily additions of modified substrates remained constant over 4 days by feeding of additional 10 µM per day (day 1-4). Alternatively, additions of modified substrate(s) were done on day one and day three after inoculation by feeding of the modified substrate(s) to a concentration of 30 µM in the medium at each of the days. Growth of cultures was monitored daily by measurements of optical density at 750 nm (OD750 nm). Cultivation was finished by adding methanol to the culture to an end concentration of 20%. Subsequently extraction was done via a standard solid phase extraction procedure using C18-modified silica cartridges.

For other scales mentioned above the protocols were similar and only slightly varied. For example, at 2 and 20 L scale the medium was not always buffered and due to the slower growth rate the duration of cultivation was prolonged for another week. Furthermore, in some cases increased amounts of added modified substrates up to 300 µM media concentration were used (if strain tolerated such concentrations) in order to increase the yield of modified non-ribosomal peptides.

TABLE

Recipe for BG11 medium which has been used for feeding experiments

| Component | mg/L | mM |
|---|---|---|
| $NaNO_3$ | 1500 | 17.6 |
| $K_2HPO_4*3H_2O$ | 40 | 0.23 |
| $MgSO_4*7H_2O$ | 75 | 0.3 |
| $CaCl_2*2H_2O$ | 36 | 0.24 |
| $Na_2CO_3$ | 20 | 0.19 |
| Ferric ammon•citrate | 6 | 0.021 |
| Citric acid | 6 | 0.031 |
| $Na_2EDTA*2H_2O$ | 1 | 0.0027 |

| Trace elements | µg/L | µM |
|---|---|---|
| $H_3BO_3$ | 2.86 | 46.3 |
| $MnCl_2•4H_2O$ | 1.8 | 9.15 |
| $ZnSO_4•7H_2O$ | 0.22 | 0.77 |
| $Na_2MoO_4•2H_2O$ | 0.390 | 1.61 |
| $CuSO_4•5H_2O$ | 0.079 | 0.32 |
| $Co(NO_3)_2•6H_2O$ | 0.0494 | 0.17 |

Table: Recipe for BG11 medium which has been used for feeding experiments

For the following strains feeding of at least one modified and clickable substrate were demonstrated.

| Cyano Biotech Strain ID NO. | Genera | Main microcystin variants produced |
|---|---|---|
| 1 | Microcystis | MC-YR |
| 275 | Microcystis | MC-LR |
| | | MC-LW |
| | | MC-LF |
| 329 | Planktothrix | (D-Asp3, Dhb7)MC-RR |
| 480 | Microcystis | MC-LR |
| | | MC-YR |
| 633 | Microcystis | MC-RR |
| 959 | Microcystis | MC-LR |
| | | MC-YR |

MC is microcystin, the two letters behind MC define the amino acids at the variable positions 2 and 4 whereas R is arginine, Y is tyrosine, L is leucine, W is tryptophan, and F is phenylalanine. D-MAsp3 is D-erythro-β-methylaspartic acid at position 3 and Dhb7 is dehydrobutyrate at position 7.

FIGS. 7A-25 illustrate incorporations of modified amino acids into microcystins and nodularins at different positions and produced by different genera and strains, resp. which carry clickable anchor groups or anchor groups that are easily accessible to additional modification towards conjugable anchor groups.

The following tables summarize results of feeding experiments of different cyanobacterial genera and strains, resp. with one or two modified substrates each comprising an anchor group directly accessible or transformable for use in conjugation chemistry (incl. click chemistry), for the attachment of a targeting moiety and/or a label via a linker or w/o a linker between the modified amino acid and the targeting moiety and/or a label.

TABLE 1

Part 1 of summary of results of feeding one modified substrate to different cyanobacterial strains of the genera Microcystis and Planktothrix.
MC-microcystin with letters behind MC indicating the amino acids at the variable position 2 and 4 in the one-letter-code.

| CBT strain no. | Genera/ Species | NRP variants naturally produced by the strain | Naturally produced NRP variate which is effected by fed modified substrate | Sum formula of naturally produced NRP variant | Monoisotopic mass of naturally produced NRP variant | Naturally incorporated amino acid which is replaced by modified substrate | Sum formula (zwitterion) of natural substrate | Monoisotopic mass (Zwitterion) of natural substrate | Position of naturally incorporated amino acid in NRP |
|---|---|---|---|---|---|---|---|---|---|
| 1 | Microcystis sp. | MC-LR MC-YR | MC-YR | C52H72N10O13 | 1044.52803 | Arg | C6H14N4O2 | 174.111679 | 2 |
| 1 | Microcystis sp. | MC-LR MC-YR | MC-YR | C52H72N10O13 | 1044.52803 | Tyr | C9H11NO3 | 181.073898 | 4 |
| 1 | Microcystis sp. | MC-LR MC-YR | MC-YR | C52H72N10O13 | 1044.52803 | Arg | C6H14N4O2 | 174.111679 | 2 |
| 1 | Microcystis sp. | MC-LR MC-YR | MC-YR | C52H72N10O13 | 1044.52803 | Tyr | C9H11NO3 | 181.073898 | 4 |
| 265 | Microcystis aeruginosa | MC-LR, Cyanopeptolin A, B, C, D und 963A; Microcyclamide, Aeruginosin, Aerucyclamide A, B, C, D | MC-LR | C49H74N10O12 | 994.548767 | Arg | C6H14N4O2 | 174.111679 | 4 |
| 265 | Microcystis aeruginosa | MC-LR, Cyanopeptolin A, B, C, D und 963A; Microcyclamide, Aeruginosin, Aerucyclamide A, B, C, D | MC-LR | C49H74N10O12 | 994.548767 | Leu | C6H13NO2 | 131.094635 | 2 |
| 275 | Microcystis aeruginosa | MC-LR MC-LW MC-LF | MC-LR | C49H74N10O12 | 994.548767 | Arg | C6H14N4O2 | 174.111679 | 4 |
| 275 | Microcystis aeruginosa | MC-LR MC-LW MC-LF | MC-LR | C49H74N10O12 | 994.548767 | Arg | C6H14N4O2 | 174.111679 | 4 |
| 275 | Microcystis aeruginosa | MC-LR MC-LW MC-LF | MC-LR | C49H74N10O12 | 994.548767 | Arg | C6H14N4O2 | 174.111679 | 4 |
| 275 | Microcystis aeruginosa | MC-LR MC-LW MC-LF | MC-LF | C52H71N7O12 | 985.516071 | Phe | C9H11NO2 | 165.078979 | 4 |
| 275 | Microcystis aeruginosa | MC-LR MC-LW MC-LF | MC-LF | C52H71N7O12 | 985.516071 | Phe | C9H11NO2 | 165.078979 | 4 |
| 275 | Microcystis aeruginosa | MC-LR MC-LW MC-LF | MC-LR | C49H74N10O12 | 994.548767 | Arg | C6H14N4O2 | 174.111679 | 4 |
| 275 | Microcystis aeruginosa | MC-LR MC-LW MC-LF | MC-LR | C49H74N10O12 | 994.548767 | Arg | C6H14N4O2 | 174.111679 | 4 |
| 275 | Microcystis aeruginosa | MC-LR MC-LW MC-LF | MC-LW | C54H72N8O12 | 1024.52697 | Trp | C11H12N2O2 | 204.089878 | 4 |
| 275 | Microcystis aeruginosa | MC-LR MC-LW MC-LF | MC-LW | C54H72N8O12 | 1024.52697 | Trp | C11H12N2O2 | 204.089878 | 4 |

TABLE 1-continued

Part 1 of summary of results of feeding one modified substrate to different cyanobacterial strains of the genera Microcystis and Planktothrix. MC-microcystin with letters behind MC indicating the amino acids at the variable position 2 and 4 in the one-letter-code.

| CBT strain no. | Genera/ Species | Short name of modified substrate | Sum formula (zwitterion) of modified substrate | Monoisotopic mass (zwitter ion) of modified substrate | Mass difference between natural und modified substrate (Da) | Calculated monoisotopic mass of mutasynthesis product (novel microcystin) | Measured monoisotopic mass of mutasyn + thesis product [M + H]⁺ | MS Peak EIC (Mass spectometry) | UV Peak PDA (HPLC) |
|---|---|---|---|---|---|---|---|---|---|
| 1 | Microcystis sp. | Azido-lys | C6H12N4O2 | 172.0960 | 2.0157 | 1042.5124 | 1043.5197 | yes | yes |
| 1 | Microcystis sp. | Prg-Tyr | C12H13NO3 | 219.0895 | −38.0156 | 1082.5437 | 1083.5510 | yes | yes |
| 1 | Microcystis sp. | Nitro-Arg | C6H13N5O4 | 219.0968 | −44.9851 | 1089.5131 | 1090.5204 | yes | yes |
| 1 | Microcystis sp. | Azido-L-Phe | C9H10N4O2 | 206.0804 | −25.0065 | 1069.5345 | 1070.5418 | yes | yes |
| 265 | Microcystis aeruginosa | Prg-Tyr | C12H13NO3 | 219.0895 | −44.9779 | 1039.5266 | 1040.5339 | yes | no |
| 265 | Microcystis aeruginosa | Prg-Tyr | C12H13NO3 | 219.0895 | −87.9949 | 1082.5437 | 1083.5510 | yes | no |
| 275 | Microcystis aeruginosa | Nitro-Arg | C6H13N5O4 | 219.0968 | −44.9851 | 1039.5338 | 1040.5411 | yes | undetermined |
| 275 | Microcystis aeruginosa | Furyl-Ala | C7H9NO3 | 155.0582 | 19.0534 | 975.4953 | 976.5026 | yes | undetermined |
| 275 | Microcystis aeruginosa | Lys(Poc) | C10H16N2O4 | 228.1110 | −53.9993 | 1048.5481 | 1049.5554 | yes | undetermined |
| 275 | Microcystis aeruginosa | Prg-Tyr | C12H13NO3 | 219.0895 | −54.0106 | 1039.5266 | 1040.5339 | yes | yes |
| 275 | Microcystis aeruginosa | Azido-L-Phe | C9H10N4O2 | 206.0804 | −41.0014 | 1026.5175 | 1027.5247 | yes | yes |
| 275 | Microcystis aeruginosa | Azido-Lys | C6H12N4O2 | 172.0960 | 2.0157 | 992.5331 | 993.5404 | yes | yes |
| 275 | Microcystis aeruginosa | Azido-Norval | C5H10N4O2 | 158.0804 | 16.0313 | 978.5175 | 979.5247 | yes | yes |
| 275 | Microcystis aeruginosa | Prg-Tyr | C12H13NO3 | 219.0895 | −14.9997 | 1039.5266 | 1040.5339 | yes | yes |
| 275 | Microcystis aeruginosa | Azido-L-Phe | C9H10N4O2 | 206.0804 | −1.9905 | 1026.5175 | 1027.5247 | yes | yes |

TABLE 2

Part 2 of summary of results of feeding one modified substrate to different cyanobacterial strains of the genera Microcystis and Planktothrix. MC-microcystin with letters behind MC indicating the amino acids at the variable position 2 and 4 in the one-letter-code.

| CBT strain no. | Genera/ Species | NRP variants naturally produced by the strain | Naturally produced NRP variate which is effected by fed modified substrate | Sum formula of naturally produced NRP variant | Monoisotopic mass of naturally produced NRP variant | Naturally incorporated amino acid which is replaced by modified substrate | Sum formula (zwitterion) of natural substrate | Monoisotopic mass (Zwitterion) of natural substrate | Position of naturally incorporated amino acid in NRP |
|---|---|---|---|---|---|---|---|---|---|
| 329 | Planktothrix agardhii | (D-Asp3, E-Dhb7) MC-RR | (D-Asp3, E-Dhb7) MC-RR | C48H73N13O12 | 1023.5502 | Arg | C6H14N4O2 | 174.11168 | 4 |
| 332 | Planktothrix rubescens | Anabaenopeptin A, B, E/Fund NZ857, (D-Asp3, E-Dhb7) MC-RR | (D-Asp3, E-Dhb7) MC-RR | C48H73N13O12 | 1023.5502 | Arg | C6H14N4O2 | 174.11168 | 2 |
| 480 | Microcystis aeruginosa | MC-LR (D-Asp3) MC-YR | MC-LR | C49H74N10O12 | 994.548767 | Leu | C6H13NO2 | 131.09464 | 2 |
| 480 | Microcystis aeruginosa | MC-LR (D-Asp3) MC-YR | MC-LR | C49H74N10O12 | 994.548767 | Arg | C6H14N4O2 | 174.11168 | 4 |

TABLE 2-continued

Part 2 of summary of results of feeding one modified substrate to different cyanobacterial strains of the genera Microcystis and Planktothrix. MC-microcystin with letters behind MC indicating the amino acids at the variable position 2 and 4 in the one-letter-code.

| 480 | Microcystis aeruginosa | MC-LR (D-Asp3) MC-YR | MC-LR | C49H74N10O12 | 994.548767 | Arg | C6H14N4O2 | 174.11168 | 4 |
| 480 | Microcystis aeruginosa | MC-LR (D-Asp3) MC-YR | MC-YR | C52H72N10O13 | 1044.52803 | Arg | C6H14N4O2 | 174.11168 | 4 |
| 480 | Microcystis aeruginosa | MC-LR (D-Asp3) MC-YR | MC-YR | C52H72N10O13 | 1044.52803 | Tyr | C9H11NO3 | 181.0739 | 2 |
| 480 | Microcystis aeruginosa | MC-LR (D-Asp3) MC-YR | MC-YR | C52H72N10O13 | 1044.52803 | Arg | C6H14N4O2 | 174.11168 | 4 |
| 480 | Microcystis aeruginosa | MC-LR (D-Asp3) MC-YR | MC-YR | C52H72N10O13 | 1044.52803 | Tyr | C9H11NO3 | 181.0739 | 2 |
| 480 | Microcystis aeruginosa | MC-LR (D-Asp3) MC-YR | MC-YR | C52H72N10O13 | 1044.52803 | Tyr | C9H11NO3 | 181.0739 | 2 |
| 480 | Microcystis aeruginosa | MC-LR (D-Asp3) MC-YR | MC-LR | C49H74N10O12 | 994.548767 | Leu | C6H13NO2 | 131.09464 | 2 |
| 480 | Microcystis aeruginosa | MC-LR (D-Asp3) MC-YR | MC-YR | C52H72N10O13 | 1044.52803 | Tyr | C9H11NO3 | 181.0739 | 2 |

| CBT strain no. | Genera/ Species | Short name of modified substrate | Sum formula (zwitterion) of modified substrate | Monoisotopic mass (zwitterion) of modified substrate | Mass difference between natural und modified substrate (Da) | Calculated monoisotopic mass of mutasynthesis product (novel microcystin) | Measured monoisotopic mass of mutasynthesis product $[M + H]^+$ | MS Peak EIC (Mass spectometry) | UV Peak PDA (HPLC) |
|---|---|---|---|---|---|---|---|---|---|
| 329 | Planktothrix agardhii | Nitro-Arg | C6H13N5O4 | 219.0968 | 44.9851 | 1068.5353 | 1069.5426 | yes | yes |
| 332 | Planktothrix rubescens | Prg-Tyr | C12H13NO3 | 219.0895 | −44.9779 | 1068.5281 | 1069.5353 | yes | yes |
| 480 | Microcystis aeruginosa | Azido-Norval | C5H10N4O2 | 158.0804 | −26.9857 | 1021.5345 | 1022.5418 | yes | undetermined |
| 480 | Microcystis aeruginosa | Nitro-Arg | C6H13N5O4 | 219.0968 | −44.9851 | 1039.5338 | 1040.5411 | yes | yes |
| 480 | Microcystis aeruginosa | Azido-Lys | C6H12N4O2 | 172.0960 | 2.0157 | 992.5331 | 993.5404 | yes | yes |
| 480 | Microcystis aeruginosa | Azido-Lys | C6H12N4O2 | 172.0960 | 2.0157 | 1042.5124 | 1043.5197 | yes | yes |
| 480 | Microcystis aeruginosa | Prg-Tyr | C12H13NO3 | 219.0895 | −38.0156 | 1082.5437 | 1083.5510 | yes | yes |
| 480 | Microcystis aeruginosa | Nitro-Arg | C6H13N5O4 | 219.0968 | −44.9851 | 1089.5131 | 1090.5204 | yes | yes |
| 480 | Microcystis aeruginosa | Azido-L-Phe | C9H10N4O2 | 206.0804 | −25.0065 | 1069.5345 | 1070.5418 | yes | yes |
| 480 | Microcystis aeruginosa | Prg-Tyr | C12H13NO3 | 219.0895 | −38.0156 | 1082.5437 | 1083.5510 | yes | yes |
| 480 | Microcystis aeruginosa | Azido-Lys | C6H12N4O2 | 172.0960 | −41.0014 | 1035.5502 | 1036.5574 | yes | yes |
| 480 | Microcystis aeruginosa | Azido-Lys | C6H12N4O2 | 172.0960 | 8.9779 | 1035.5502 | 1036.5574 | yes | yes |

TABLE 3

Part 3 of summary of results of feeding one modified substrate to different cyanobacterial strains of the genera Microcystis and Planktothrix. MC-microcystin with letters behind MC indicating the amino acids at the variable position 2 and 4 in the one-letter-code.

| CBT strain no. | Genera/ Species | NRP variants naturally produced by the strain | Naturally produced NRP variate which is effected by fed modified substrate | Sum formula of naturally produced NRP variant | Monoisotopic mass of naturally produced NRP variant | Naturally incorporated amino acid which is replaced by modified substrate | Sum formula (zwitterion) of natural substrate | Monoisomass (Zwitterion) of natural substrate | Position of naturally porated amino acid in NRP |
|---|---|---|---|---|---|---|---|---|---|
| 633 | Microcystis sp. | MC-RR | MC-RR | C49H75N13O12 | 1037.5658 | Arg | C6H14N4O2 | 174.11168 | 2 |
| 633 | Microcystis sp. | MC- TABLE 3-continued Part 3 of summary of results of feeding one modified substrate to different cyanobacterial strains of the genera Microcystis and Planktothrix. MC-microcystin with letters behind MC indicating the amino acids at the variable position 2 and 4 in the one-letter-code.

| 959 | Microcystis sp. | Azido-L-AJa | C3H6N4O2 | 130.0491 | 44.0626 | 950.4862 | 951.4934 | yes | yes |
|---|---|---|---|---|---|---|---|---|---|
| 959 | Microcystis sp. | Azido-L-AJa | C3H6N4O2 | 130.0491 | 44.0626 | 1000.4654 | 1001.4727 | yes | yes |
| 959 | Microcystis sp. | Azido-Norval | C5H10N4O2 | 158.0804 | 16.0313 | 978.5175 | 979.5247 | yes | yes |
| 959 | Microcystis sp. | Azido-Norval | C5H10N4O2 | 158.0804 | 16.0313 | 1028.4967 | 1029.5040 | yes | yes |
| 959 | Microcystis sp. | Prg-Tyr | C12H13NO3 | 219.0895 | −38.0156 | 1082.5437 | 1083.5510 | yes | yes |
| 959 | Microcystis sp. | Azido-L-Phe | C9H10N4O2 | 206.0804 | −25.0065 | 1069.5345 | 1070.5418 | yes | yes |
| 1161 | Planktothrix rubescens | Prg-Tyr | C12H13NO3 | 219.0895 | −44.9779 | 1068.5281 | 1069.5353 | yes | yes |
| 861 R | Microcystis aeruginosa | Azido-Lys | C6H12N4O2 | 172.0960 | −41.0014 | 1042.5124 | 1043.5197 | yes | yes |
| 861 R | Microcystis aeruginosa | Azido-Lys | C6H12N4O2 | 172.0960 | 2.0157 | 1042.5124 | 1043.5197 | yes | yes |
| 861 R | Microcystis aeruginosa | Azido-Lys | C6H12N4O2 | 172.0960 | 8.9779 | 1035.5502 | 1036.5574 | yes | yes |

FIGURE CAPTIONS

FIG. 1A:

General structure of Microcystins. X2 and Z4 indicate variable L-amino acids. D-Ala=D-Alanine, D-Me-Asp=D-methyl aspartic acid, Arg=Arginine, Adda=3-amino-9-methoxy-2,6,8-trimethyl-10-phenyldeca-4,6-dienoic acid, D-Glu=D-glutamic acid, Mdha=N-methyldehydroalanine.

Figure 1A:
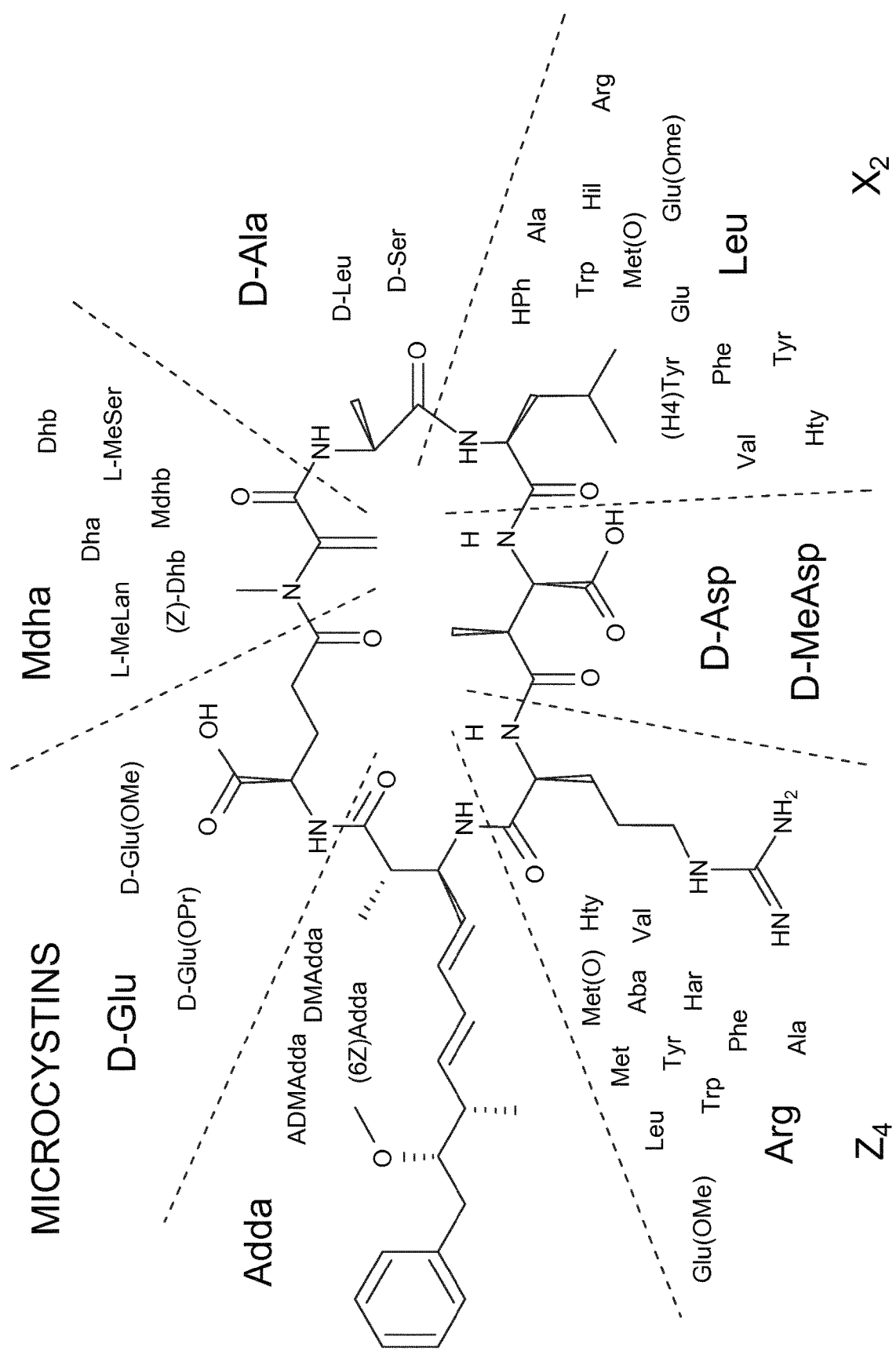
FIG. 1A: General structure of Microcystins. $X_2$ and $Z_4$ indicate variable L-amino acids. D-Ala=D-Alanine, D-Me-Asp=D-methyl aspartic acid, Arg=Arginine, Adda=3-amino-9-methoxy-2,6,8-trimethyl-10-phenyldeca-4,6-dienoic acid, D-Glu=D-glutamic acid, Mdha=N-methyldehydroalanine.
Figure 1B:
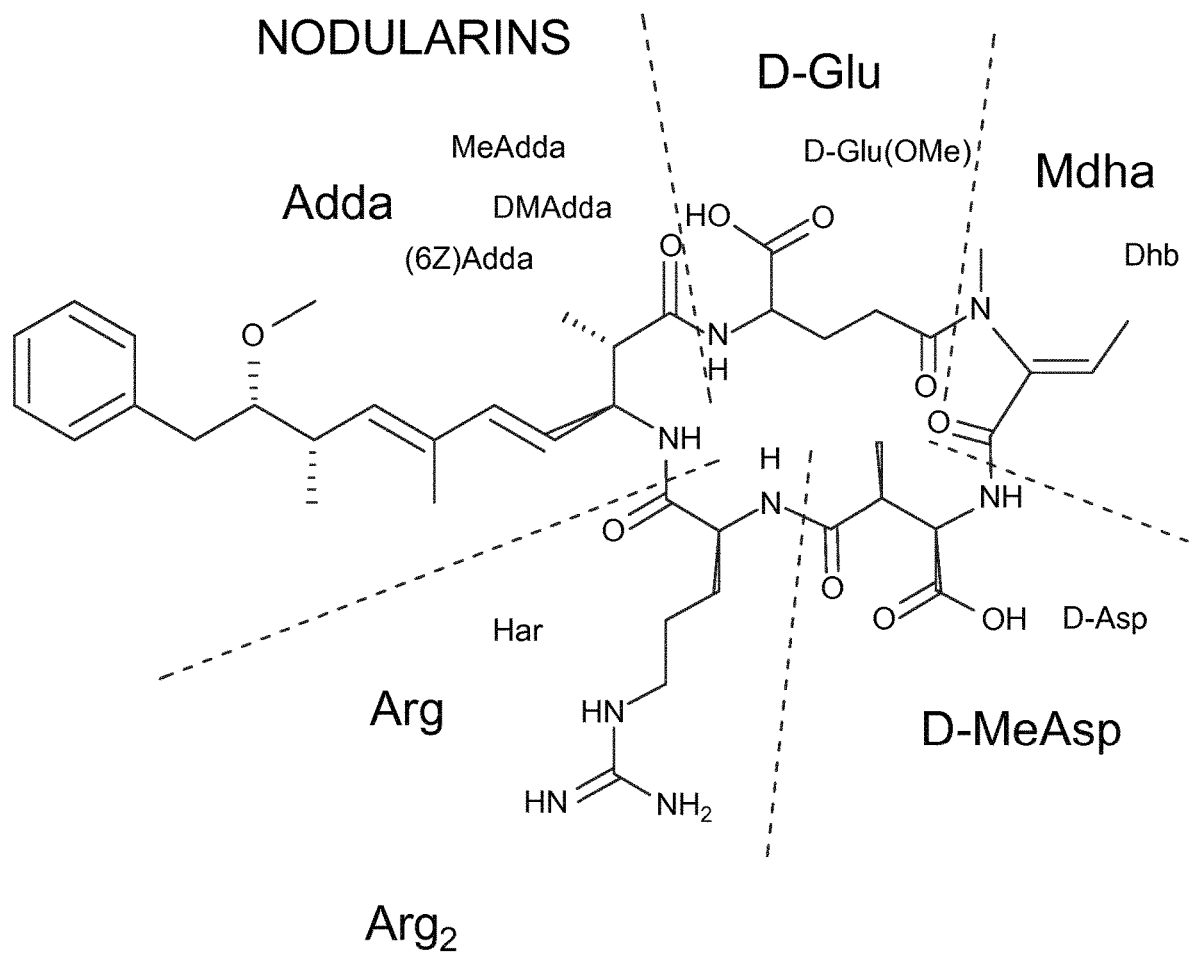
FIG. 1B: General structure of Nodularins. Arg2 indicates the variable L-amino acid corresponding to Z4 in the microcystin molecule. D-Me-Asp=D-methyl aspartic acid, Arg=Arginine, Adda=3-amino-9-methoxy-2,6,8-trimethyl-10-phenyldeca-4,6-dienoic acid, D-Glu=D-glutamic acid, Mdhb=N-methyldehydrobutyrate
Figure 1C:
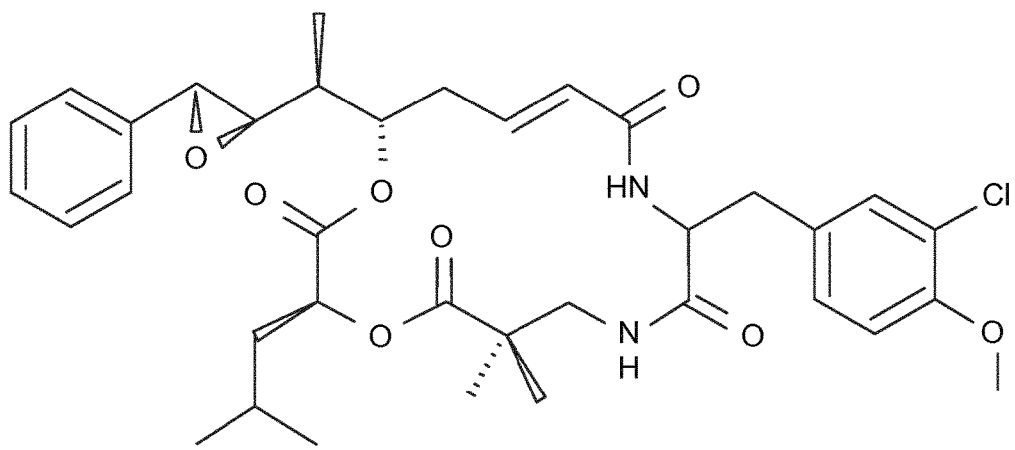
FIG. 1C: General structure ofAnabaenopeptins/Oscillamides.
Figure 2A:
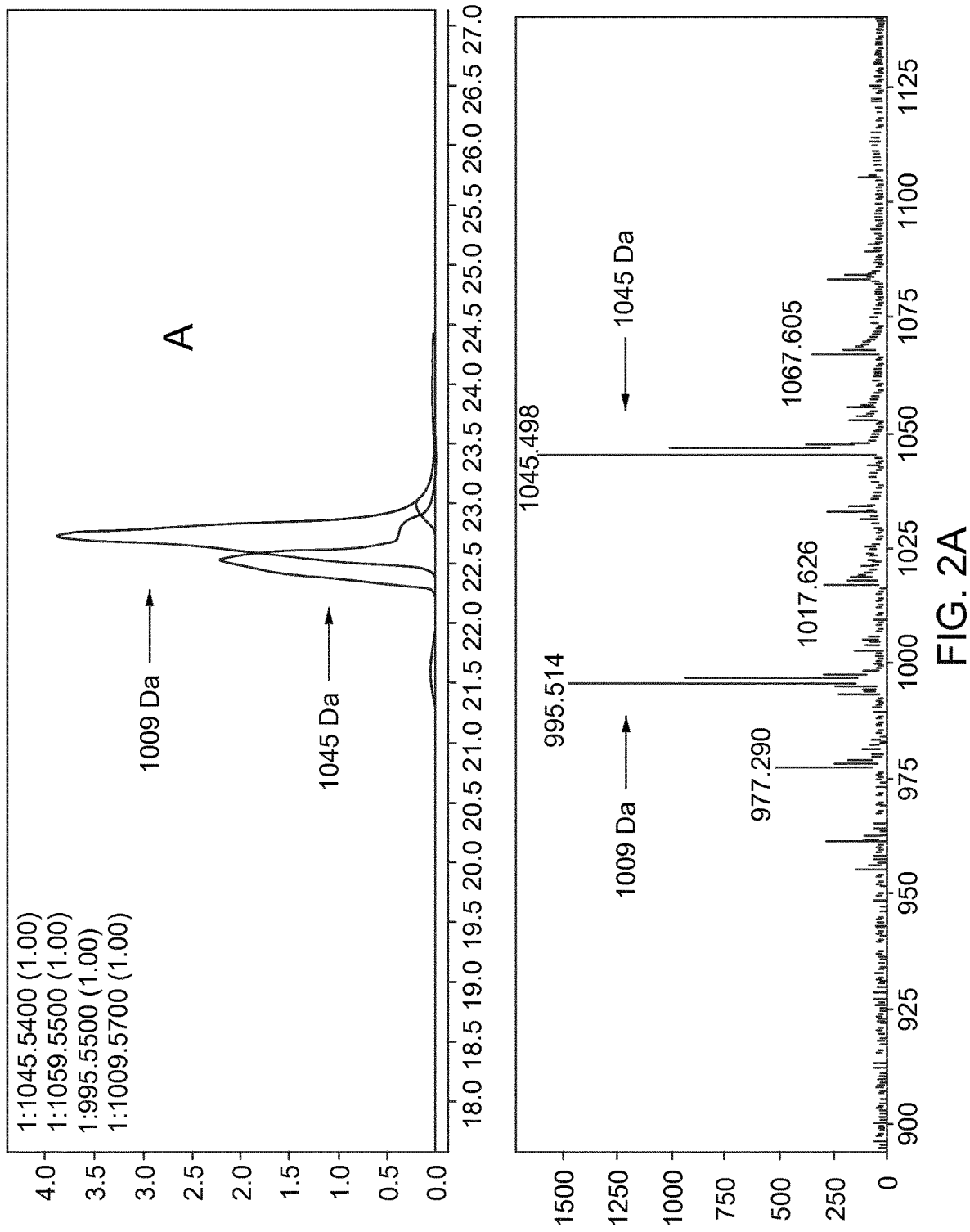
FIG. 2A: Detection of modified microcystins by two different mass spectrometry method after feeding of modified substrates to a *Microcystis aeruginosa* strain CBT 480 in a 50 ml scale (top panel: detection with ESI-IT-ToF-MS; bottom panel: detection with MALDI-ToF-MS); A: Control (no feeding with O-methyltyrosine); Molecule masses of naturally produced microcystins: 995 Da=MC-LR, 1045 Da=MC-YR; Molecule masses of modified microcystins generated by feeding with O-methyltyrosine (OMetY) and homoarginine (hR); 1059 Da=MC-OMetYR or MC-YhR; 1009 Da=MC-LhR.
Figure 2B:
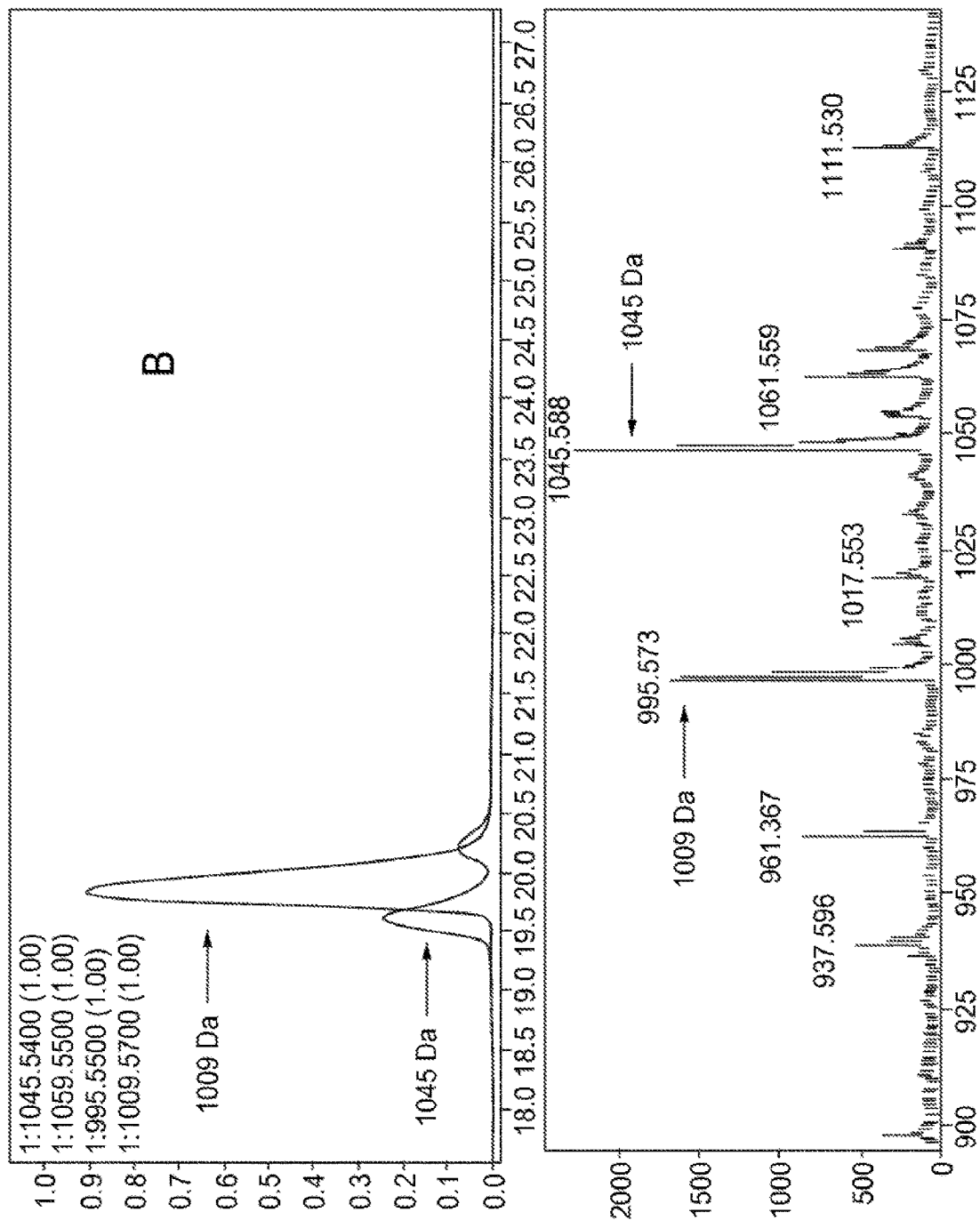
FIG. 2B: Detection of modified microcystins by two different mass spectrometry method after feeding of modified substrates to a Microcystis aeruginosa strain CBT 480 in a 50 ml scale (top panel: detection with ESI-IT-ToF-MS; bottom panel: detection with MALDI-ToF-MS); B: Control (no feeding with homoarginine); Molecule masses of naturally produced microcystins: 995Da=MC-LR, 1045 Da=MC-YR; Molecule masses of modified microcystins generated by feeding with O-methyltyrosine (OMetY) and homoarginine(hR); 1059 Da=MC-OMetYR or MC-YhR; 1009 Da=MC-LhR.
Figure 2C:
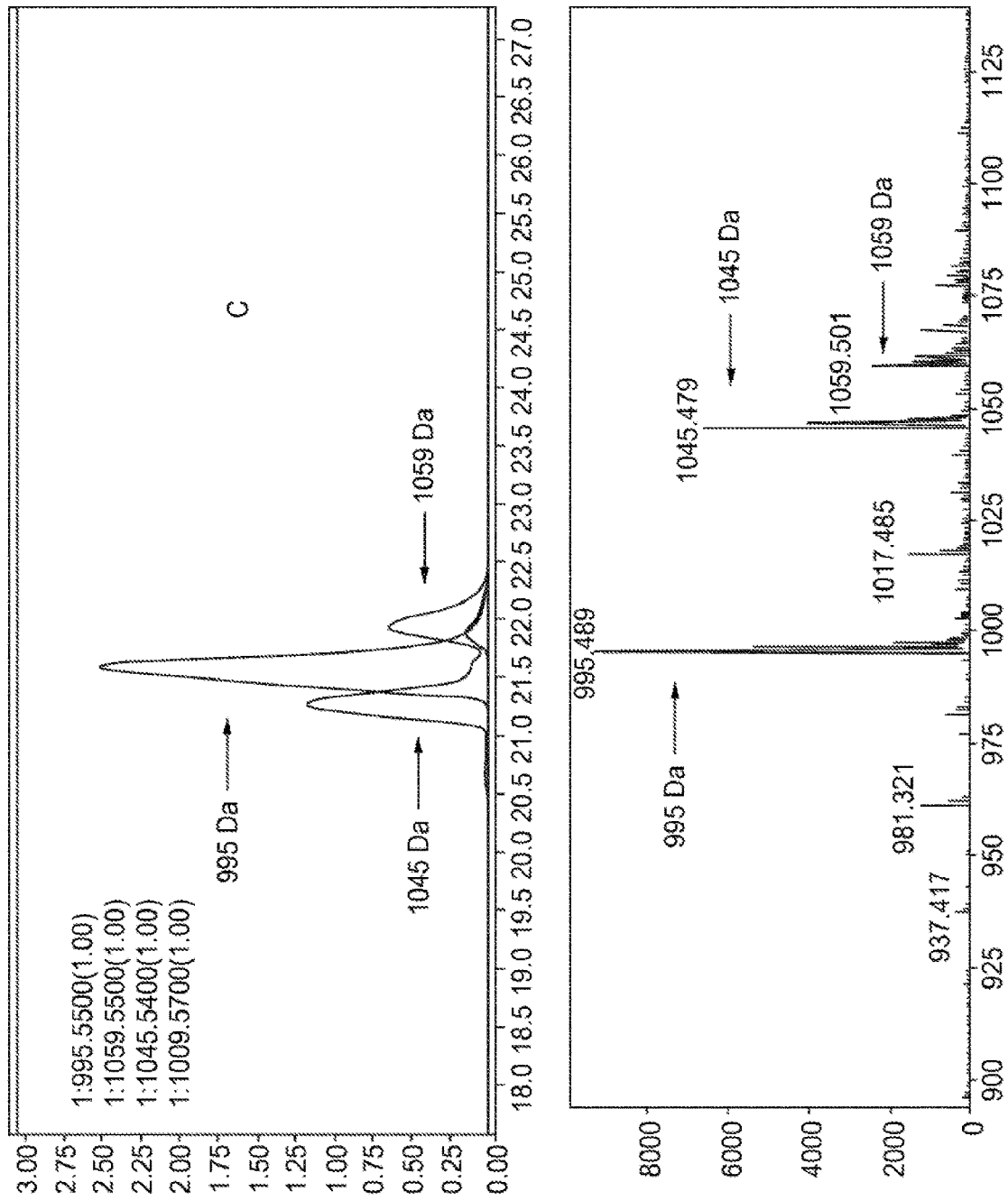
FIG. 2C: Detection of modified microcystins by two different mass spectrometry method after feeding of modified substrates to a Microcystis aeruginosa strain CBT 480 in a 50 ml scale (top panel: detection with ESI-IT-ToF-MS; bottom panel: detection with MALDI-ToF-MS); C: Feeding with O-methyltyrosine; Molecule masses of naturally produced microcystins: 995Da=MC-LR, 1045 Da=MC-YR; Molecule masses of modified microcystins generated by feeding with O-methyltyrosine (OMetY) and homoarginine (hR); 1059 Da=MC-OMetYR or MC-YhR; 1009 Da=MC-LhR.
Figure 2D:
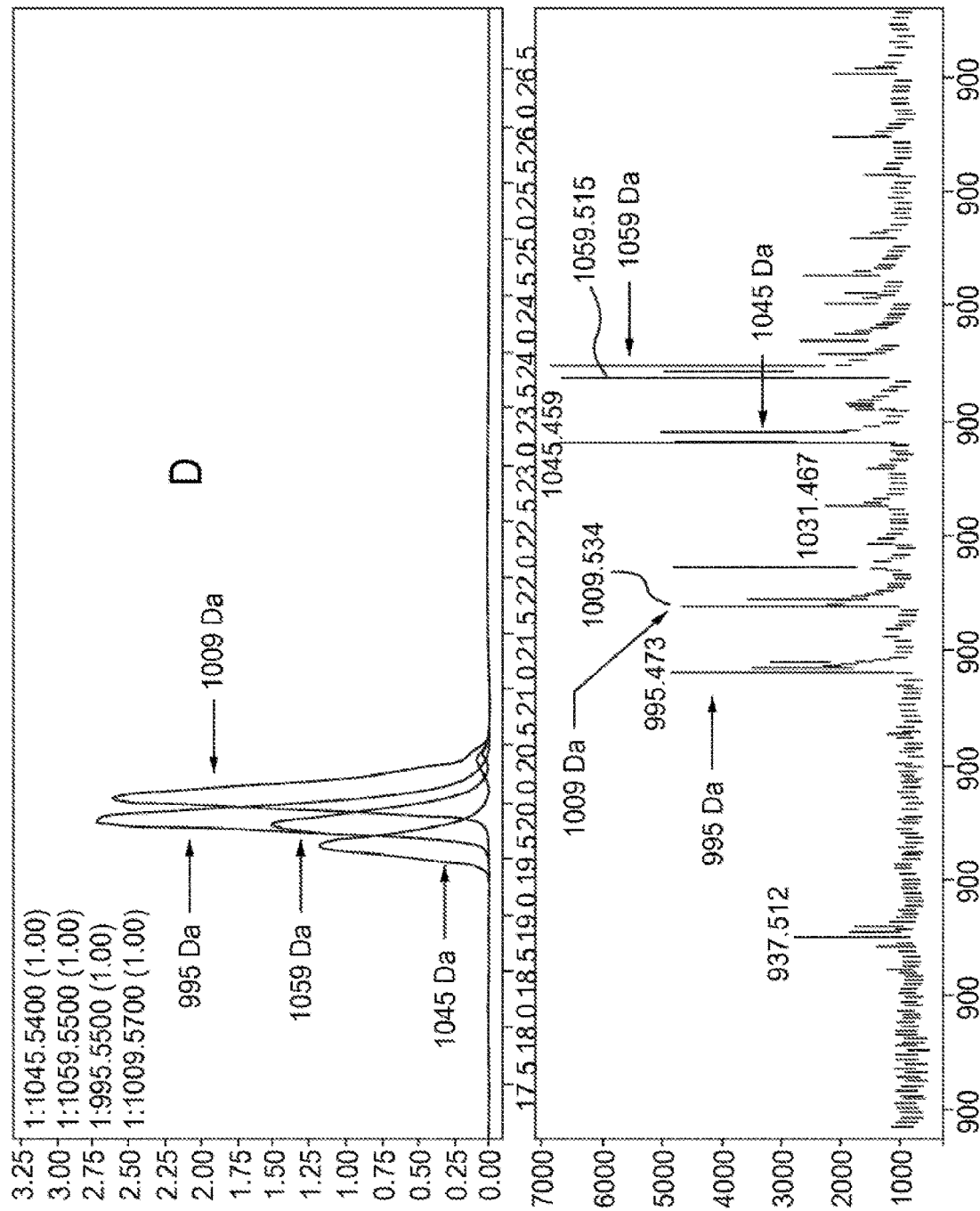
FIG. 2D: Detection of modified microcystins by two different mass spectrometry method after feeding of modified substrates to a Microcystis aeruginosa strain CBT 480 in a 50 ml scale (top panel: detection with ESI-IT-ToF-MS; bottom panel: detection with MALDI-ToF-MS); D: Feeding with homoarginine; Molecule masses of naturally produced microcystins: 995Da=MC-LR, 1045 Da=MC-YR; Molecule masses of modified microcystins generated by feeding with O-methyltyrosine (OMetY) and homoarginine (hR); 1059 Da=MC-OMetYR or MC-YhR; 1009 Da=MC-LhR.

FIG. 1B: General structure of Nodularins. Arg2 indicates the variable L-amino acid corresponding to Z4 in the microcystin molecule. D-Me-Asp=D-methyl aspartic acid, Arg=Arginine, Adda=3-amino-9-methoxy-2,6,8-trimethyl-10-phenyldeca-4,6-dienoic acid, D-Glu=D-glutamic acid, Mdhb=N-methyldehydrobutyrate

FIGS. 2A-5E:

Comparison between different cultivation systems and scales and different mass spectrometry detections in the context of suitable screening approaches towards strains that are suited for feeding of modified substrates for modifying non-ribosomal peptides including CA like microcystins and nodularins (FIGS. 2A-5E).

FIGS. 2A-2D:

Detection of modified microcystins by two different mass spectrometry method after feeding of modified substrates to a *Microcystis aeruginosa* strain CBT 480 in a 50 ml scale (above of each of the four figures A, B, C, D detection with ESI-IT-ToF-MS; below of each of the four figures A, B, C, D detection with MALDI-ToF-MS).

A: Control (no feeding with O-methyltyrosine) B: Control (no feeding with homoarginine)

C: Feeding with O-methyltyrosine D: Feeding with homoarginine

Molecule masses of naturally produced microcystins:
995 Da=MC-LR, 1045 Da=MC-YR

Molecule masses of modified microcystins generated by feeding with O-methyltyrosine (OMetY) and homoarginine (hR)

1059 Da=MC-OMetYR or MC-YhR; 1009 Da=MC-LhR

FIGS. 3A-3B:

Detection of modified microcystins by two different mass spectrometry method after feeding of modified substrates to a *Microcystis aeruginosa* strain CBT 480 in a 6 ml scale (above of each of the two figures A/A' and B/B' detection with ESI-IT-ToF-MS; below of each of the two figures A/A' and B/B' detection with MALDI-ToF-MS).

A, A': CBT 480 culture fed with O-methyltyrosine B, B': CBT 480 culture fed with homoarginine Molecule masses of naturally produced microcystins: 995 Da=MC-LR, 1045 Da=MC-YR Molecule masses of modified microcystins generated by feeding with O-methyltyrosine (OMetY) and homoarginine (hR)

1059 Da=MC-OMetYR or MC-YhR; 1009 Da=MC-LhR;

FIGS. 4A-4E:

Detection of modified microcystins by two different mass spectrometry method after feeding of modified substrates to a *Microcystis aeruginosa* strain CBT 480 with O-methyltyrosine in a 1.6 ml (dw-MTP) scale (ESI-IT-ToF-MS on the left; MALDI-ToF-MS on the right)

A, A': feeding of 300 μM O-methyltyrosine (OMetY), w/o DMSO

B, B': feeding of 30 μM O-methyltyrosine (OMetY), w/o DMSO

C, C': feeding of 300 μM O-methyltyrosine (OMetY), w/1% DMSO

D, D': feeding of 30 μM O-methyltyrosine (OMetY), w/1% DMSO

E, E': control (no feeding)

Molecule masses of naturally produced microcystins:
995 Da=MC-LR, 1045 Da=MC-YR

Molecule masses of modified microcystin generated by feeding with O-methyltyrosine 1059 Da=MC-OMetYR

FIGS. 5A-5E:

Detection of modified microcystins by two different mass spectrometry method after feeding of modified substrates to a *Microcystis aeruginosa* strain CBT 480 with homoarginine in a 1.6 ml (dw-MTP) sclale (ESI-IT-ToF-MS detection on the left; MALDI-ToF-MS detection on the right)

A, A': feeding of 300 μM homoarginine (hR), w/o DMSO

B, B': feeding of 30 μM homoarginine (hR), w/o DMSO

C, C': feeding of 300 μM homoarginine (hR), w/1% DMSO

D, D': feeding of 30 μM homoarginine (hR), w/1% DMSO

E, E': control (no feeding)

Molecule masses of naturally produced microcystins:
995 Da=MC-LR, 1045 Da=MC-YR

Molecule masses of modified microcystins generated by feeding with homoarginine
1059 Da=MC-YhR; 1009 Da=MC-LhR All modified microcystins could be detected with both MS methods. However, most samples resulting from feeding without the addition of DMSO of 1% in the culture medium could not be detected with MALDI-ToF-MS but with ESI-IT-ToF-MS. Therefore, it is recommended to use DMSO for feeding experiments in screenings of small scale cultures (between 1 and 10 ml culture volumes) especially if the MS detection of modified non-ribosomal peptides is based on MALDI-ToF-MS.

On the other side MALDI-ToF-MS detection of modified non-ribosomal peptides after feeding of modified substrates to small scale cultures of 1.6 ml cultivated in deep-well-microtiter plates (dw-MTW) allows for high throughput screening (HTS). Both cultivation (with and without feeding of modified substrates) and sample preparation for MALDI-ToF-MS can be done using a pipetting robot allowing for the parallel test of diverse strains and substrates as described in Tillich et al. BMC Microbiology 2014, 14:239.

FIG. 6:

McyBI represent the first of two enzyme modules of McyB and is responsible for the incorporation of the amino acid at the position 2 of the microcystin molecule. This is the amino acid leucine in case of the Microcystin *aeruginosa* strain PCC7806 whereas it is leucine OR tyrosine in the *Microcystis aeruginosa* strain CBT 480. The so called core motifs A2-A6 of the adenylation (A) domain of McyBI are highlighted in black (A2-A6) and the amino acids responsible for substrate (amino acid) recognition and activation during the biosynthesis of the respective microcystin are indicated by big and bold white letters. These amino acids form the active pocket of the A domains and the sequence in their one-letter amino acid code represent the so called specificity-conferring code of A domains which shall allow for the prediction of substrate specificity of A domains. The only difference in the amino acid sequence of McyBI of both strains is in amino acid position 672. Only one of nine pocket-forming amino acids of the A domains of both strains is different between the strains and also the remaining parts of the A domain as well as of the whole biosynthetic gene clusters are almost identical between the strains leading to the conclusion that the incorporation of leucine and tyrosine at position 2 of the microcystin in the strain CBT 480 is a strain-specific feature but cannot be explained by differences in the DNA sequence of the biosynthetic gene clusters and amino acid sequence of the microcystin synthetases, resp. The consensus sequence as between the "Query" and "Sbjct" sequences is indicated by "Consensus" and corresponds to SEQ ID NO: 6. Each letter in the consensus sequence is an identical match. The blank spaces in the consensus sequence are where the match indicated a zero or negative score. The "+" symbol in the consensus sequence represents a conservative substitution. The "Query" sequence shown corresponds to SEQ ID NO: 4 and the "Sbjct" sequence shown corresponds to SEQ ID NO: 5.

Figure 7A:
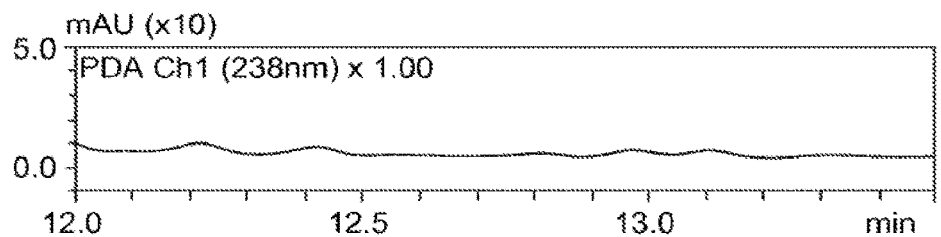
FIG. 7A: Exemplary embodiment No. 1: Incorporation of the modified substrate Azido-L-Phe (Phe=phenylalanine) into Microcystin YR in position 2 produced by strain CBT 959. HPLC-PDA Chromatogram at 238 nm for sample of control cultivation. Detector signal intensities (y-Axis) are measured in milli-absorption units (mAU) and counts (dimensionless quantity) for PDA and mass spectrometry data, respectively. The growth of strain CBT 959 could not be followed by measurement of optical density at 750 nm (OD750 nm) as the cell form aggregates making it impossible to measure reliable OD750 nm values.
Figure 7B:
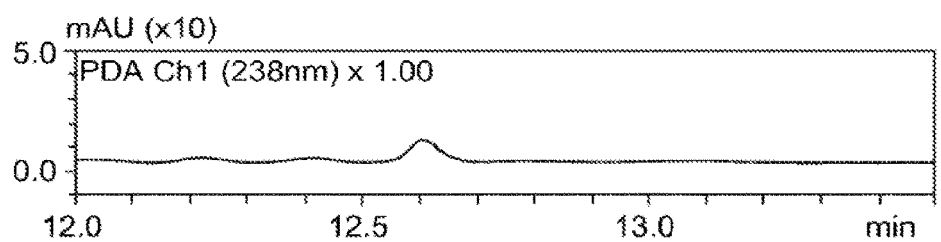
FIG. 7B: Exemplary embodiment No. 1: Incorporation of the modified substrate Azido-L-Phe (Phe=phenylalanine) into Microcystin YR in position 2 produced by strain CBT 959. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data, respectively. The growth of strain CBT 959 could not be followed by measurement of optical density at 750 nm (OD750 nm) as the cell form aggregates making it impossible to measure reliable OD750 nm values.
Figure 7C:
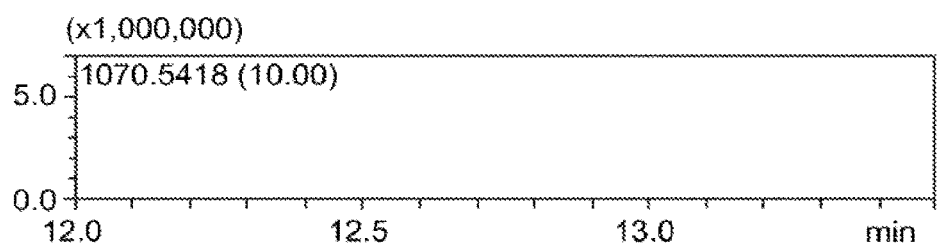
FIG. 7C: Exemplary embodiment No. 1: Incorporation of the modified substrate Azido-L-Phe (Phe=phenylalanine) into Microcystin YR in position 2 produced by strain CBT 959. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data, respectively. The growth of strain CBT 959 could not be followed by measurement of optical density at 750 nm (OD750 nm) as the cell form aggregates making it impossible to measure reliable OD750 nm values.
Figure 7D:
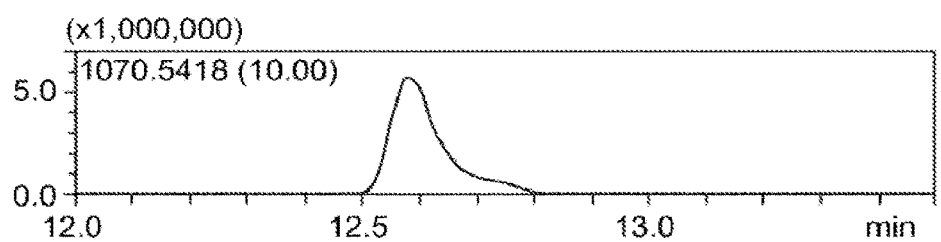
FIG. 7D: Exemplary embodiment No. 1: Incorporation of the modified substrate Azido-L-Phe (Phe=phenylalanine) into Microcystin YR in position 2 produced by strain CBT 959. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data, respectively. The growth of strain CBT 959 could not be followed by measurement of optical density at 750 nm (OD750 nm) as the cell form aggregates making it impossible to measure reliable OD750 nm values.
Figure 7E:
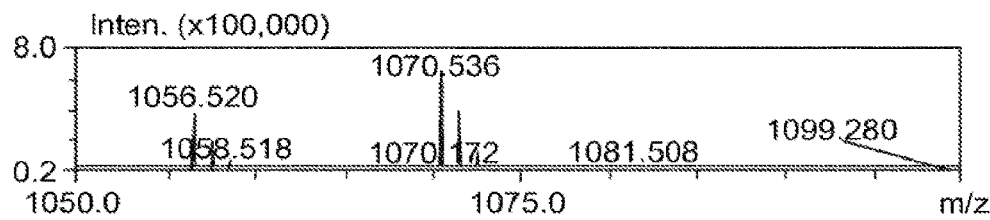
FIG. 7E: Exemplary embodiment No. 1: Incorporation of the modified substrate Azido-L-Phe (Phe=phenylalanine) into Microcystin YR in position 2 produced by strain CBT 959.

FIGS. 7A-7E:

Exemplary embodiment No. 1: Incorporation of the modified substrate Azido-L-Phe (Phe=phenylalanine) into Microcystin YR in position 2 produced by strain CBT 959. HPLC-PDA Chromatogram at 238 nm for sample of control cultivation (FIG. 7A) for sample of cultivation with added modified substrate (FIG. 7B). Extracted ion chromatogram from HPLC-MS data of mass value of protonated molecular ion of novel Microcystin variant for sample of control cultivation (FIG. 7C) and for sample of cultivation with added modified substrate (FIG. 7D) in the positive ionization mode. Finally, (FIG. 7E) shows the averaged mass spectrum of the peak visible in chromatogram FIG. 7D). Detector signal intensities (y-Axis) are measured in milli-absorption units (mAU) und counts (dimensionless quantity) for PDA and mass spectrometry data, respectively.

The growth of strain CBT 959 could not be followed by measurement of optical density at 750 nm (OD750 nm) as the cell form aggregates making it impossible to measure reliable OD750 nm values.

Figure 8A:
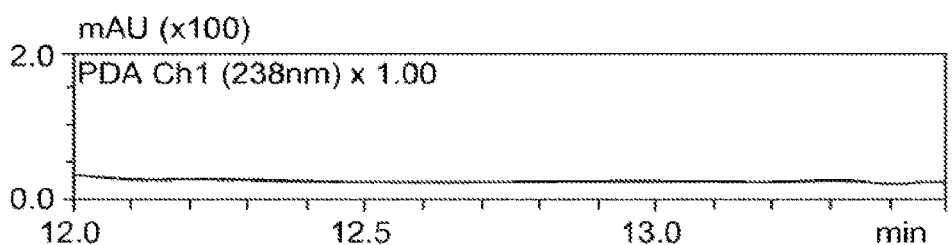
FIG. 8A: Exemplary embodiment No. 2: Incorporation of the modified substrate Prg-Tyr (Tyr=Tyrosine) into Microcystin YR in position 2 produced by strain CBT 480. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 8B:
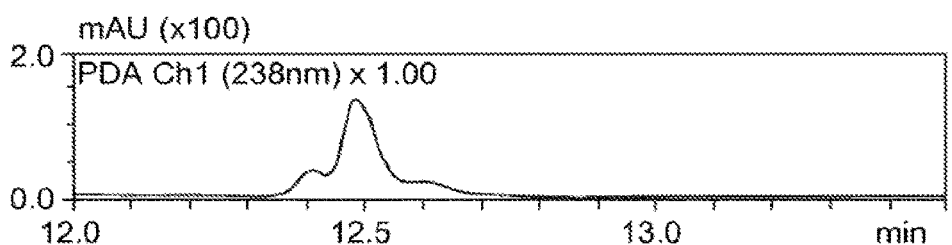
FIG. 8B: Exemplary embodiment No. 2: Incorporation of the modified substrate Prg-Tyr (Tyr=Tyrosine) into Microcystin YR in position 2 produced by strain CBT 480. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 8C:
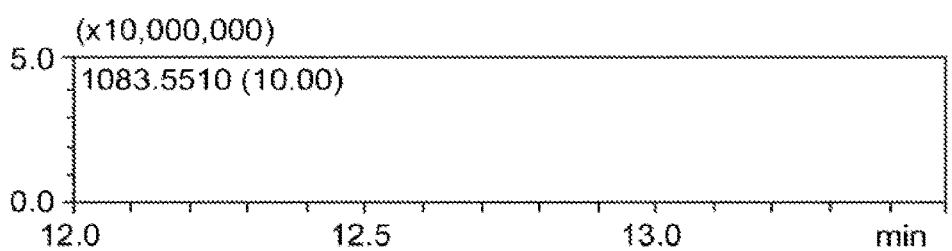
FIG. 8C: Exemplary embodiment No. 2: Incorporation of the modified substrate Prg-Tyr (Tyr=Tyrosine) into Microcystin YR in position 2 produced by strain CBT 480. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 8D:
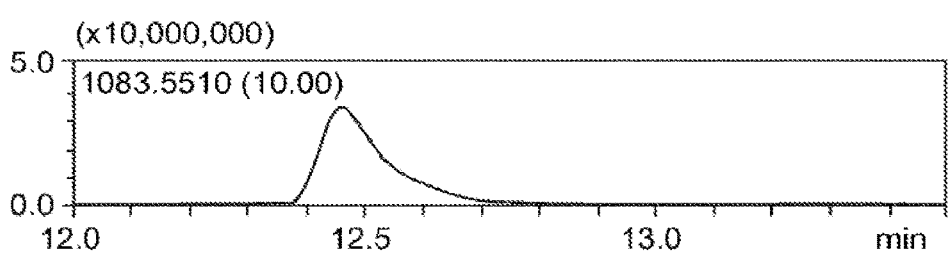
FIG. 8D: Exemplary embodiment No. 2: Incorporation of the modified substrate Prg-Tyr (Tyr=Tyrosine) into Microcystin YR in position 2 produced by strain CBT 480. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 8E:
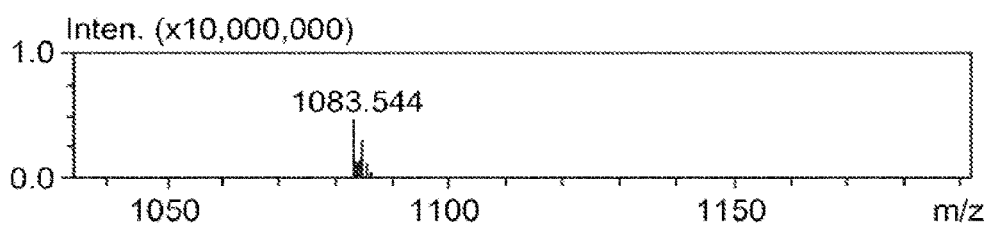
FIG. 8E: Exemplary embodiment No. 2: Incorporation of the modified substrate Prg-Tyr (Tyr=Tyrosine) into Microcystin YR in position 2 produced by strain CBT 480.
Figure 9:
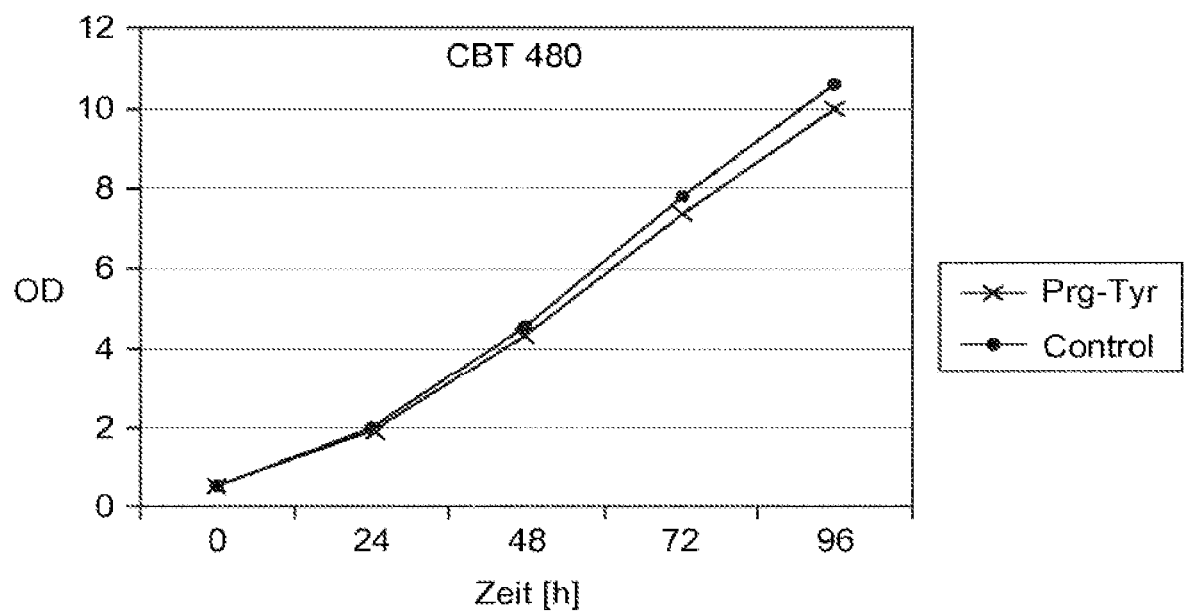
FIG. 9: Exemplary embodiment No. 2: Growths curve of CBT 480 cultures with and without Prg-Tyr (Tyr=Tyrosine) added.

FIGS. 8A-8E:

Exemplary embodiment No. 2: Incorporation of the modified substrate Prg-Tyr (Tyr=Tyrosine) into Microcystin YR in position 2 produced by strain CBT 480. HPLC-PDA Chromatogram at 238 nm for sample of control cultivation (FIG. 8A) for sample of cultivation with added modified substrate (FIG. 8B). Extracted ion chromatogram from HPLC-MS data of mass value of protonated molecular ion of novel Microcystin variant for sample of control cultivation (FIG. 8C) and sample of cultivation with added modified substrate (FIG. 8D) in the positive ionization mode. Finally, FIG. 8E) shows the averaged mass spectrum of the peak visible in chromatogram FIG. 8F). Detector signal intensities (y-Axis) are measured in milli-absorption units (mAU) und counts (dimensionless quantity) for PDA and mass spectrometry data respectively.

FIG. 9:

Exemplary embodiment No. 2: Growths curve of CBT 480 cultures with and without Prg-Tyr (Tyr=Tyrosine) added.

Figure 10A:
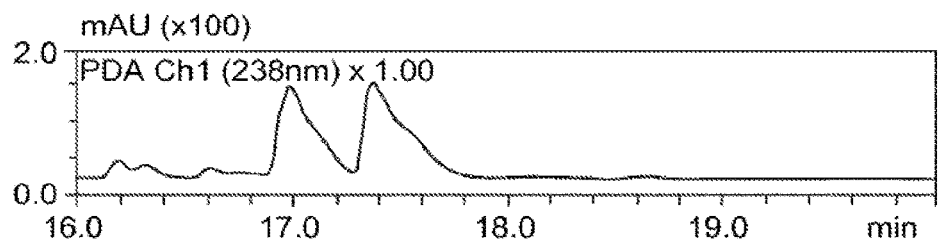
FIG. 10A: Exemplary embodiment No. 3: Incorporation of the modified substrate Azido-Lys (Lys=Lysine) into Microcystin LR in position 4 produced by strain CBT 275. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 10B:
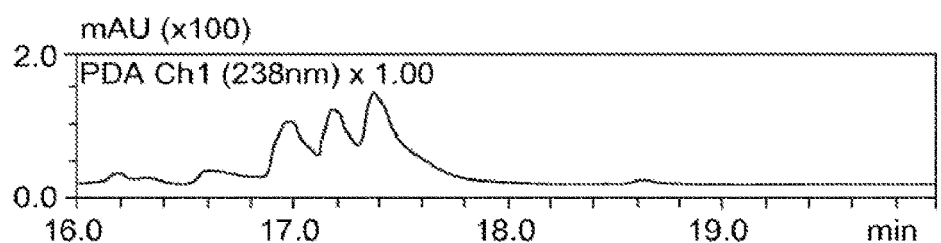
FIG. 10B: Exemplary embodiment No. 3: Incorporation of the modified substrate Azido-Lys (Lys=Lysine) into Microcystin LR in position 4 produced by strain CBT 275. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 10C:
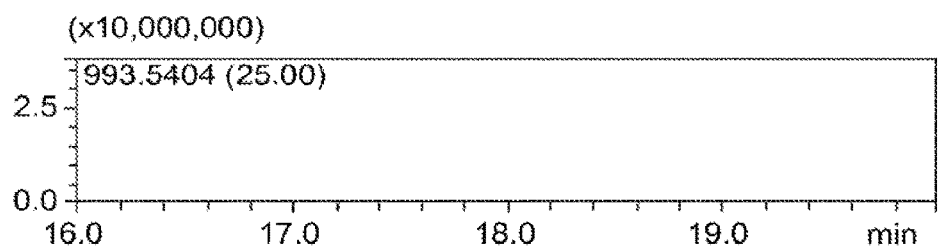
FIG. 10C: Exemplary embodiment No. 3: Incorporation of the modified substrate Azido-Lys (Lys=Lysine) into Microcystin LR in position 4 produced by strain CBT 275. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 10D:
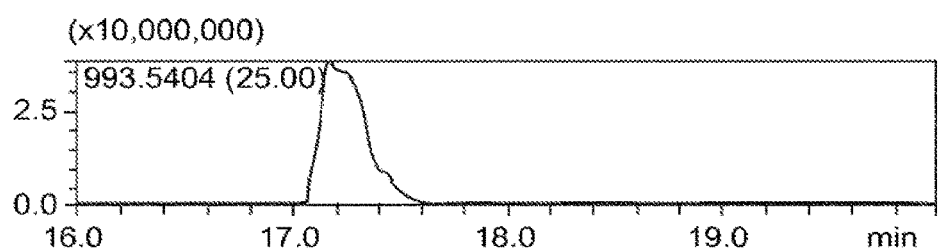
FIG. 10D: Exemplary embodiment No. 3: Incorporation of the modified substrate Azido-Lys (Lys=Lysine) into Microcystin LR in position 4 produced by strain CBT 275. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 10E:
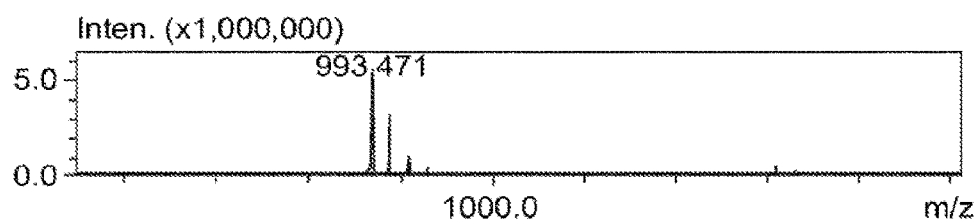
FIG. 10E: Exemplary embodiment No. 3: Incorporation of the modified substrate Azido-Lys (Lys=Lysine) into Microcystin LR in position 4 produced by strain CBT 275.
Figure 11:
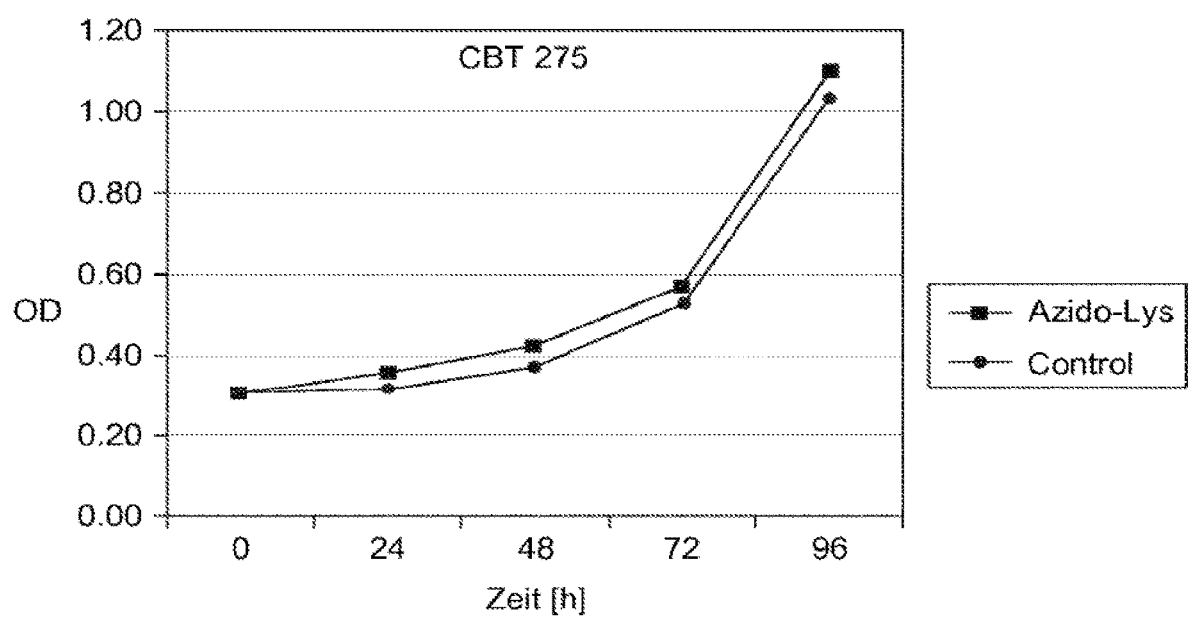
FIG. 11: Exemplary embodiment No. 3: Growths curve of CBT 275 cultures with and without Azido-Lys (Lys=Lysine) added.

FIGS. 10A-10E:

Exemplary embodiment No. 3: Incorporation of the modified substrate Azido-Lys (Lys=Lysine) into Microcystin LR in position 4 produced by strain CBT 275. HPLC-PDA Chromatogram at 238 nm for sample of control cultivation (FIG. 10A) for sample of cultivation with added modified substrate (FIG. 10B). Extracted ion chromatogram from HPLC-MS data of mass value of protonated molecular ion of novel Microcystin variant for sample of control cultivation (FIG. 10C) and sample of cultivation with added modified substrate (FIG. 10D) in the positive ionization mode. Finally, FIG. 10E) shows the averaged mass spectrum of the peak visible in chromatogram FIG. 10F). Detector signal intensities (y-Axis) are measured in milli-absorption units (mAU) und counts (dimensionless quantity) for PDA and mass spectrometry data respectively.

FIG. 11:

Exemplary embodiment No. 3: Growths curve of CBT 275 cultures with and without Azido-Lys (Lys=Lysine) added.

Figure 12A:
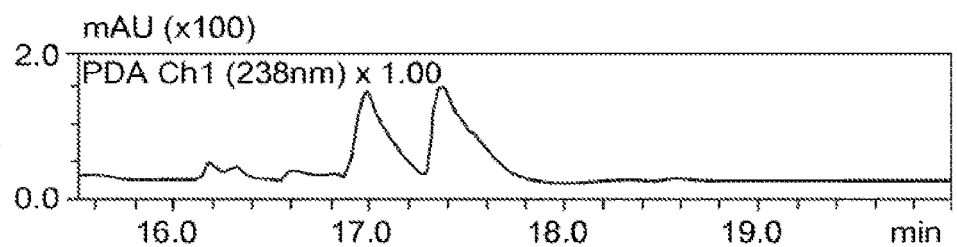
FIG. 12A: Exemplary embodiment No. 4: Incorporation of the modified substrate Prg-Tyr (Tyr=Tyrosine) into Microcystin LW in position 4 produced by strain CBT 275. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 12B:
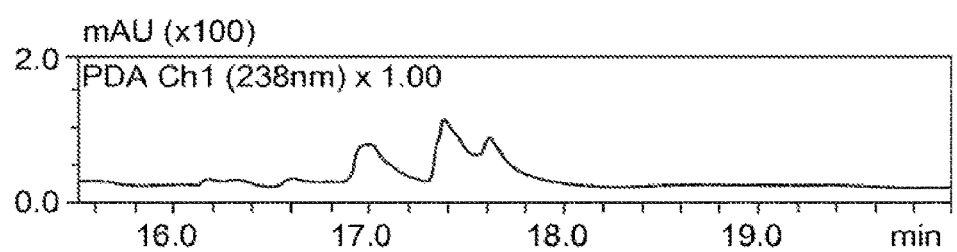
FIG. 12B: Exemplary embodiment No. 4: Incorporation of the modified substrate Prg-Tyr (Tyr=Tyrosine) into Microcystin LW in position 4 produced by strain CBT 275. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 12C:
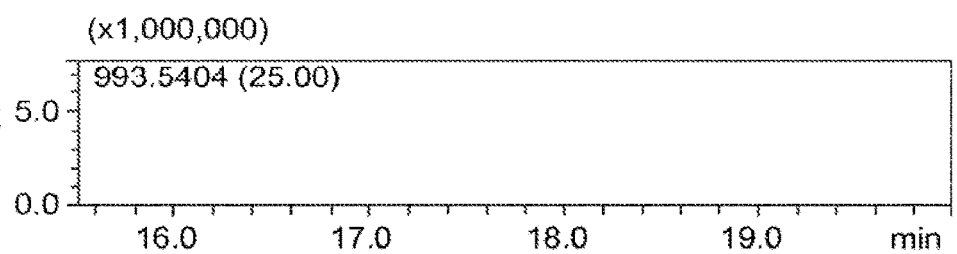
FIG. 12C: Exemplary embodiment No. 4: Incorporation of the modified substrate Prg-Tyr (Tyr=Tyrosine) into Microcystin LW in position 4 produced by strain CBT 275. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 12D:
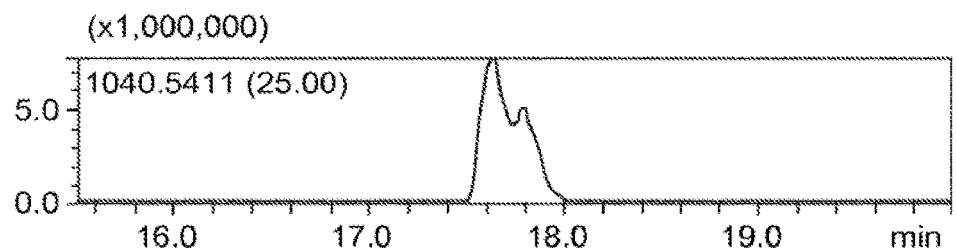
FIG. 12D: Exemplary embodiment No. 4: Incorporation of the modified substrate Prg-Tyr (Tyr=Tyrosine) into Microcystin LW in position 4 produced by strain CBT 275. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 12E:
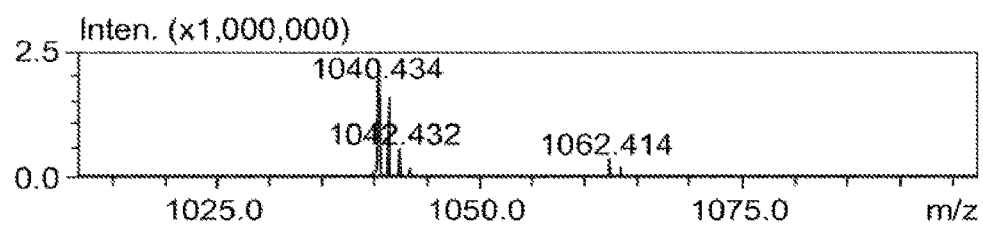
FIG. 12E: Exemplary embodiment No. 4: Incorporation of the modified substrate Prg-Tyr (Tyr=Tyrosine) into Microcystin LW in position 4 produced by strain CBT 275.
Figure 13:
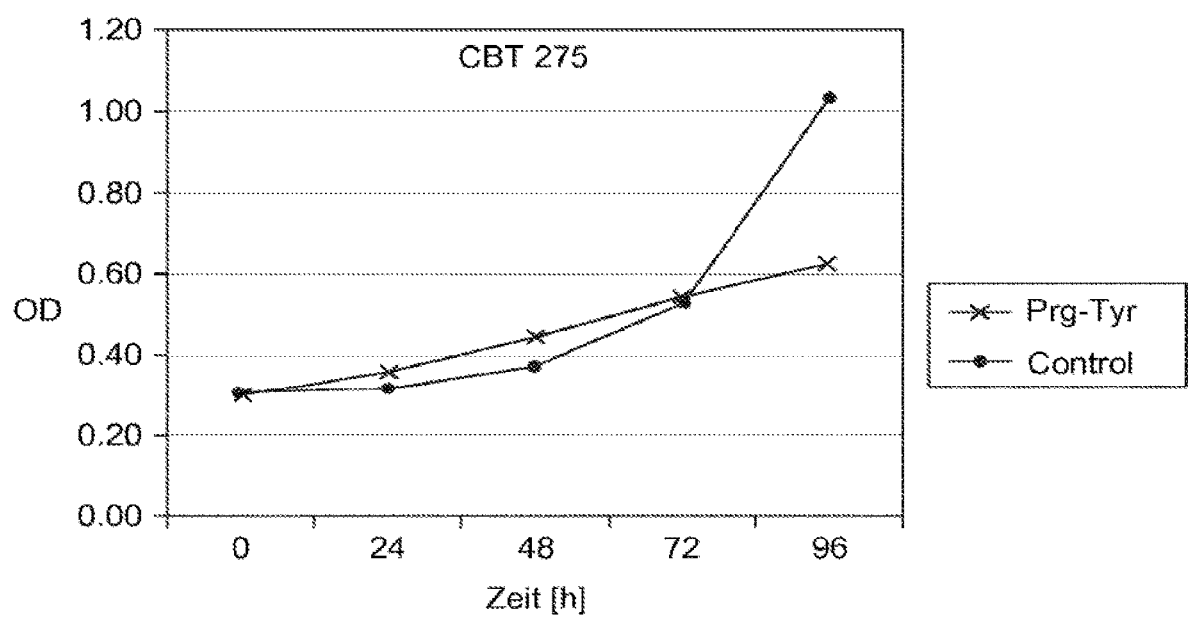
FIG. 13: Exemplary embodiment No. 4: Growths curve of CBT 275 cultures with and without Prg-Tyr (Tyr=Tyrosine) added.

FIGS. 12A-12E:

Exemplary embodiment No. 4: Incorporation of the modified substrate Prg-Tyr (Tyr=Tyrosine) into Microcystin LW in position 4 produced by strain CBT 275. HPLC-PDA Chromatogram at 238 nm for sample of control cultivation (FIG. 12A) for sample of cultivation with added modified substrate (FIG. 12B). Extracted ion chromatogram from HPLC-MS data of mass value of protonated molecular ion of novel Microcystin variant for sample of control cultivation (FIG. 12C) and sample of cultivation with added modified substrate (FIG. 12D) in the positive ionization mode. Finally, (FIG. 12E) shows the averaged mass spectrum of the peak visible in chromatogram (FIG. 12D). Detector signal intensities (y-Axis) are measured in milli-absorption units (mAU) und counts (dimensionless quantity) for PDA and mass spectrometry data respectively.

FIG. 13

Exemplary embodiment No. 4: Growths curve of CBT 275 cultures with and without Prg-Tyr (Tyr=Tyrosine) added.

FIGS. 14A-14E:

Exemplary embodiment No. 5: Incorporation of the modified substrate Nitro-Arg (Arg=Arginine) into Microcystin YR in position 4 produced by strain CBT 1.

Figure 14A:
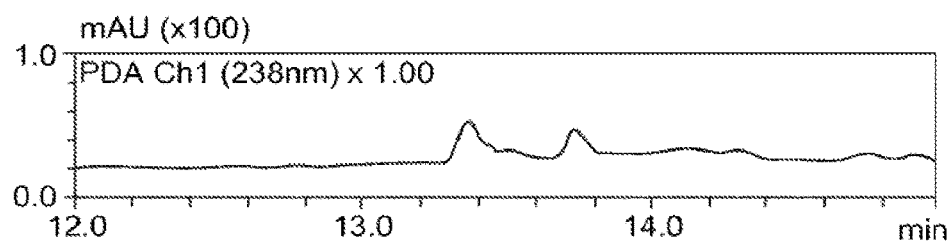
FIG. 14A: Exemplary embodiment No. 5: Incorporation of the modified substrate Nitro-Arg (Arg=Arginine) into Microcystin YR in position 4 produced by strain CBT 1. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 14B:
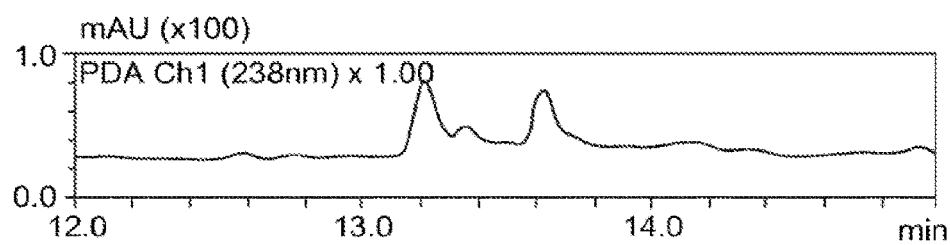
FIG. 14B: Exemplary embodiment No. 5: Incorporation of the modified substrate Nitro-Arg (Arg=Arginine) into Microcystin YR in position 4 produced by strain CBT 1. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 14C:
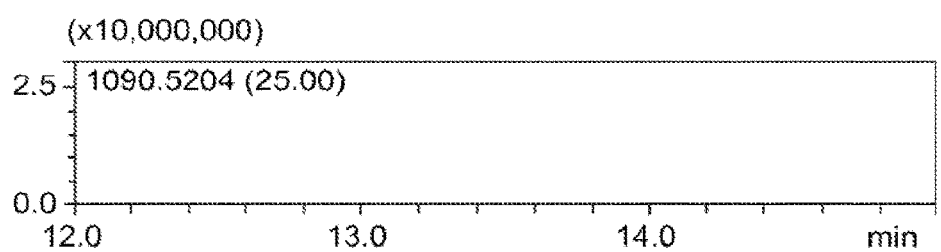
FIG. 14C: Exemplary embodiment No. 5: Incorporation of the modified substrate Nitro-Arg (Arg=Arginine) into Microcystin YR in position 4 produced by strain CBT 1. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 14D:
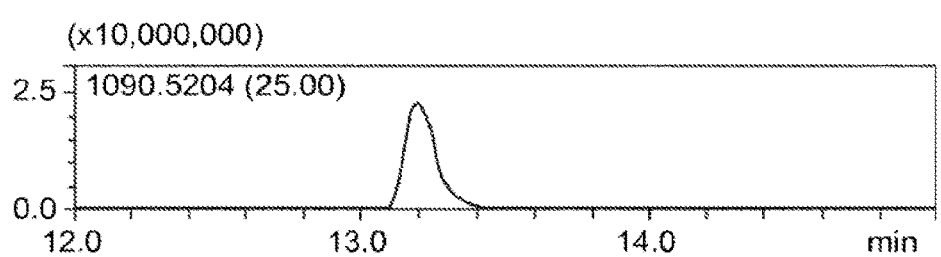
FIG. 14D: Exemplary embodiment No. 5: Incorporation of the modified substrate Nitro-Arg (Arg=Arginine) into Microcystin YR in position 4 produced by strain CBT 1. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 14E:
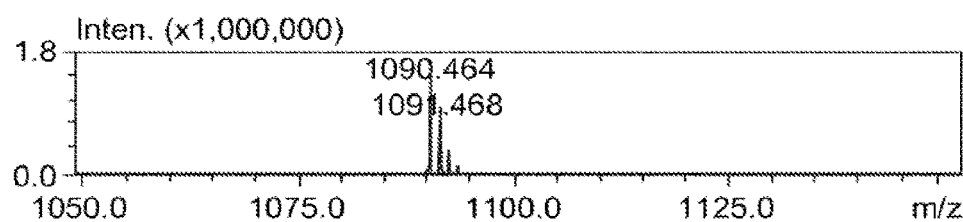
FIG. 14E: Exemplary embodiment No. 5: Incorporation of the modified substrate Nitro-Arg (Arg=Arginine) into Microcystin YR in position 4 produced by strain CBT 1.
Figure 15:
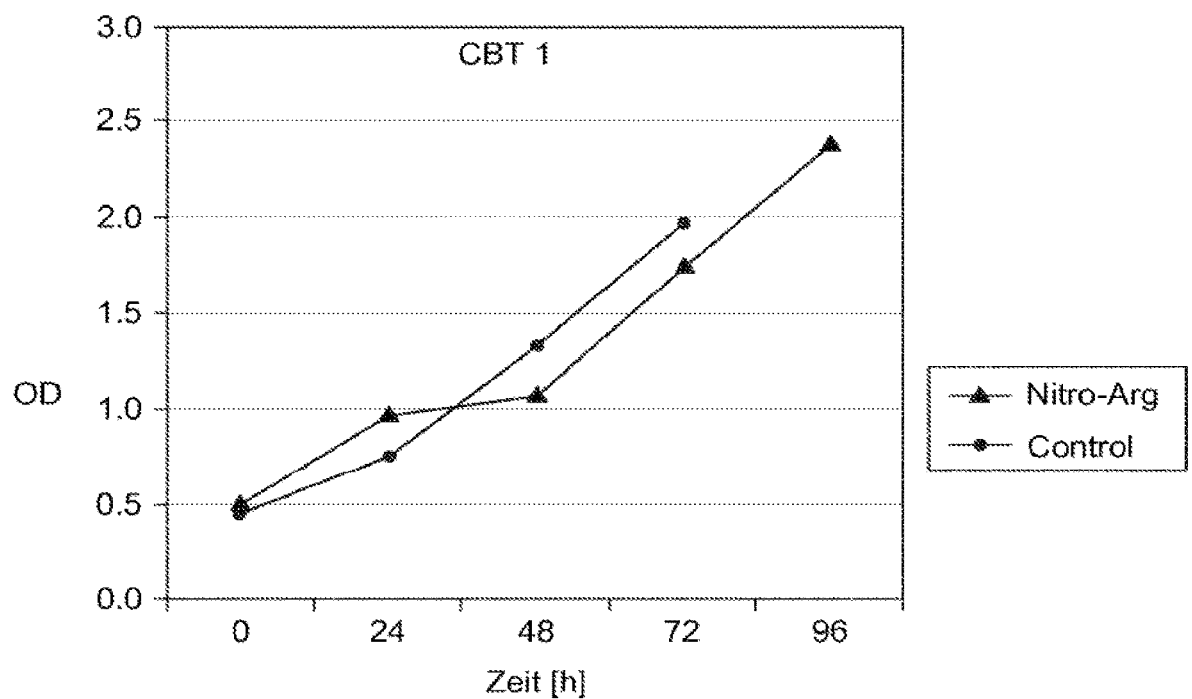
FIG. 15: Growths curve of CBT 1 cultures with and without Nitro-Arg (Arg=Arginine) added.

HPLC-PDA Chromatogram at 238 nm for sample of control cultivation (FIG. 14A) for sample of cultivation with added modified substrate (FIG. 14B). Extracted ion chromatogram from HPLC-MS data of mass value of protonated molecular ion of novel Microcystin variant for sample of control cultivation (FIG. 14C) and sample of cultivation with added modified substrate (FIG. 14D) in the positive ionization mode. Finally, (FIG. 14E) shows the averaged mass spectrum of the peak visible in chromatogram (FIG. 14E). Detector signal intensities (y-Axis) are measured in milli-absorption units (mAU) und counts (dimensionless quantity) for PDA and mass spectrometry data respectively.

FIG. 15:

Growths curve of CBT 1 cultures with and without Nitro-Arg (Arg=Arginine) added.

FIGS. 16A-16E:

Exemplary embodiment No. 6: Incorporation of the modified substrate Furyl-L-Ala (Ala=Alanine) into Microcystin LR in position 4 produced by strain CBT 275.

Figure 16A:
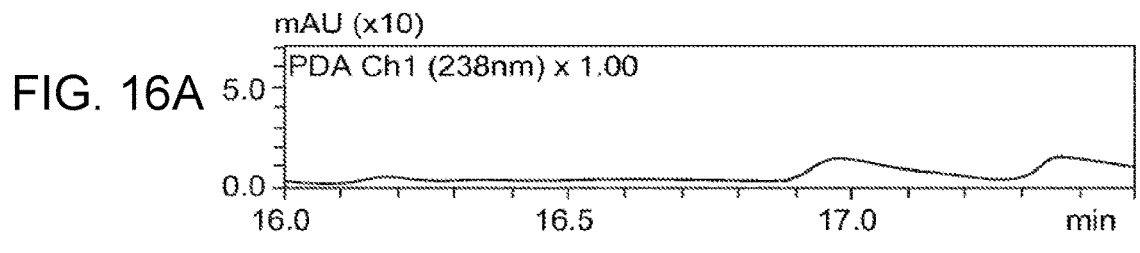
FIG. 16A: Exemplary embodiment No. 6: Incorporation of the modified substrate Furyl-L-Ala (Ala=Alanine) into Microcystin LR in position 4 produced by strain CBT 275. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively. The PDA-Signal of the novel Furyl-Ala variant of Microcystin LR is not visible due to the low concentration.
Figure 16B:
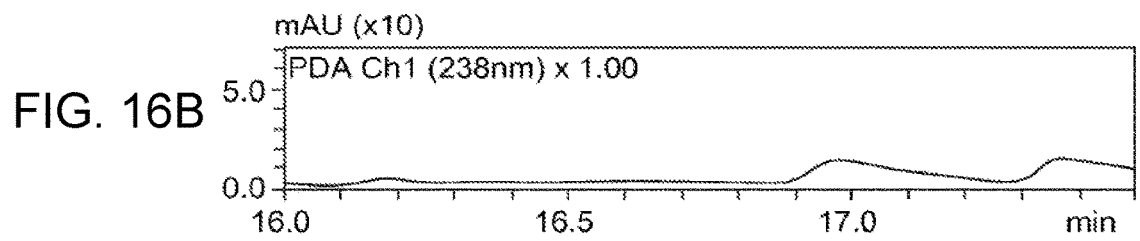
FIG. 16B: Exemplary embodiment No. 6: Incorporation of the modified substrate Furyl-L-Ala (Ala=Alanine) into Microcystin LR in position 4 produced by strain CBT 275. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively. The PDA-Signal of the novel Furyl-Ala variant of Microcystin LR is not visible due to the low concentration.
Figure 16C:
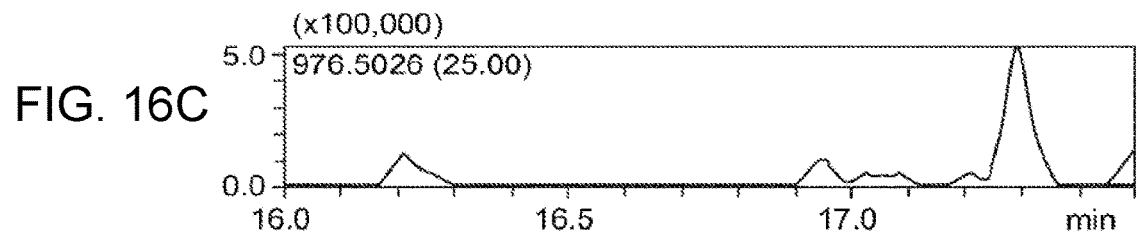
FIG. 16C: Exemplary embodiment No. 6: Incorporation of the modified substrate Furyl-L-Ala (Ala=Alanine) into Microcystin LR in position 4 produced by strain CBT 275. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively. The PDA-Signal of the novel Furyl-Ala variant of Microcystin LR is not visible due to the low concentration.
Figure 16D:
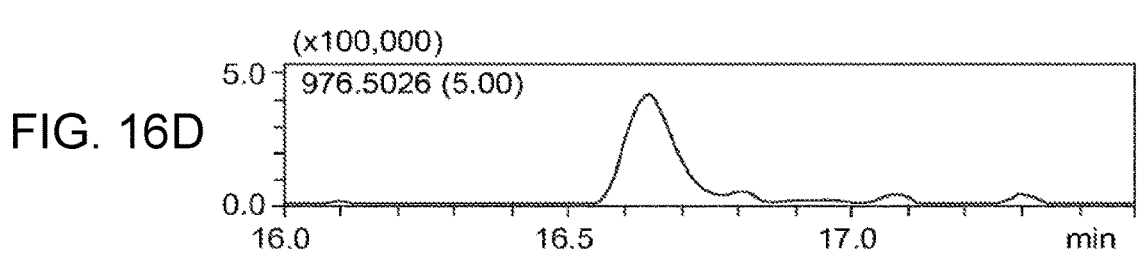
FIG. 16D: Exemplary embodiment No. 6: Incorporation of the modified substrate Furyl-L-Ala (Ala=Alanine) into Microcystin LR in position 4 produced by strain CBT 275. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively. The PDA-Signal of the novel Furyl-Ala variant of Microcystin LR is not visible due to the low concentration.
Figure 16E:
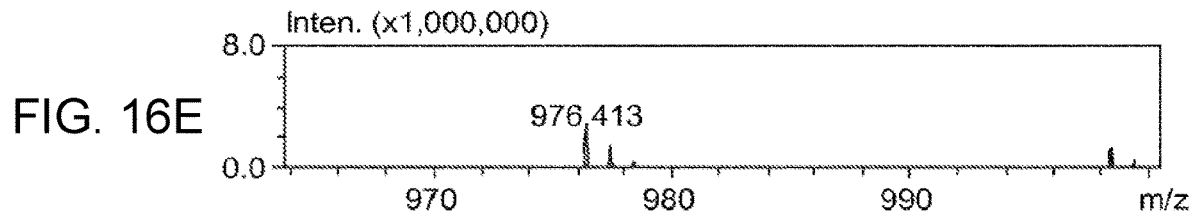
FIG. 16E: Exemplary embodiment No. 6: Incorporation of the modified substrate Furyl-L-Ala (Ala=Alanine) into Microcystin LR in position 4 produced by strain CBT 275.
Figure 17:
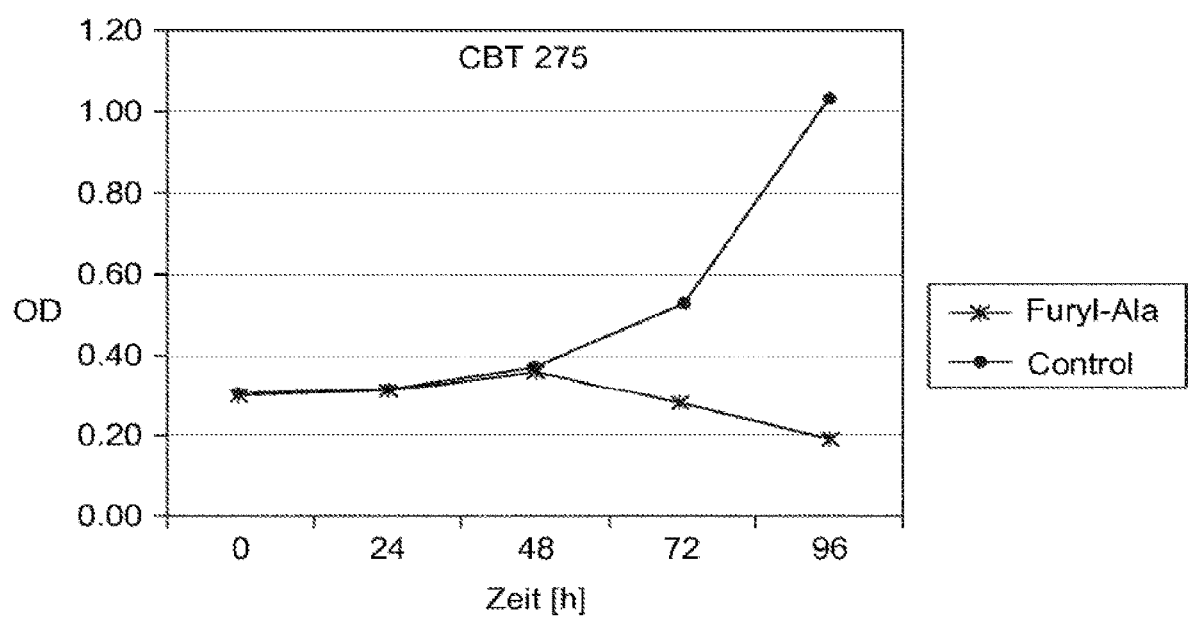
FIG. 17: Exemplary embodiment No. 6: Growths curve of CBT 275 cultures with and without Furyl-Ala (Ala=Alanine) added.

HPLC-PDA Chromatogram at 238 nm for sample of control cultivation (FIG. 16A) for sample of cultivation with added modified substrate (FIG. 16B). Extracted ion chromatogram from HPLC-MS data of mass value of protonated molecular ion of novel Microcystin variant for sample of control cultivation (FIG. 16C) and sample of cultivation with added modified substrate (FIG. 16D) in the positive ionization mode. Finally, (FIG. 16E) shows the averaged mass spectrum of the peak visible in chromatogram (FIG. 16D). Detector signal intensities (y-Axis) are measured in milli-absorption units (mAU) und counts (dimensionless quantity) for PDA and mass spectrometry data respectively. The PDA-Signal of the novel Furyl-Ala variant of Microcystin LR is not visible due to the low concentration.

FIG. 17:

Exemplary embodiment No. 6: Growths curve of CBT 275 cultures with and without Furyl-Ala (Ala=Alanine) added.

FIGS. 18A-18E:

Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480.

Figure 18A:
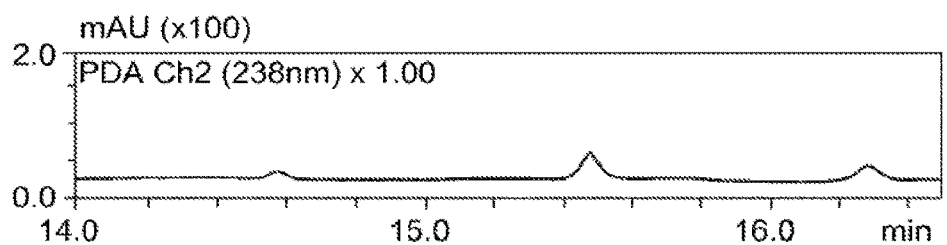
FIG. 18A: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480. HPLC-PDA Chromatogram at 238 nm for sample of control cultivation (a). Detector signal intensities (y-Axis) are measured in milli-absorption units (mAU) and counts (dimensionless quantity) for PDA and mass spectrometry data respectively.
Figure 18B:
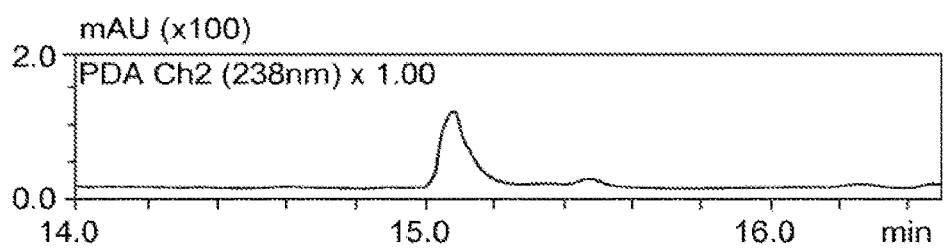
FIG. 18B: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 18C:
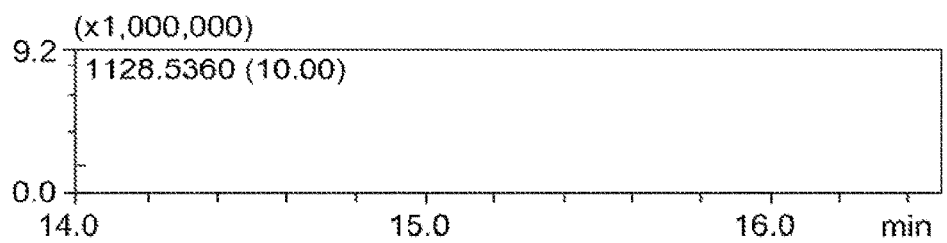
FIG. 18C: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 18D:
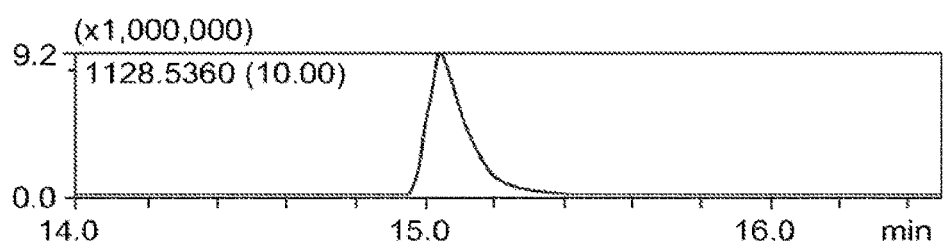
FIG. 18D: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 18E:
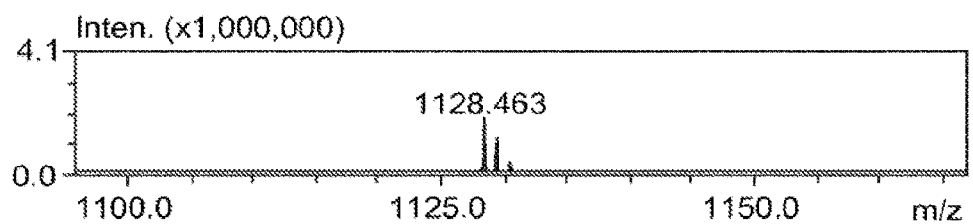
FIG. 18E: Exemplary embodiment No. 7: Incorporation of the modified substrate Nitro-Arg (Arg=Arginine) and Prg-Tyr (Tyr=Tyrosine) into Microcystin YR in position 2 and 4 respectively produced by strain CBT 480.
Figure 19:
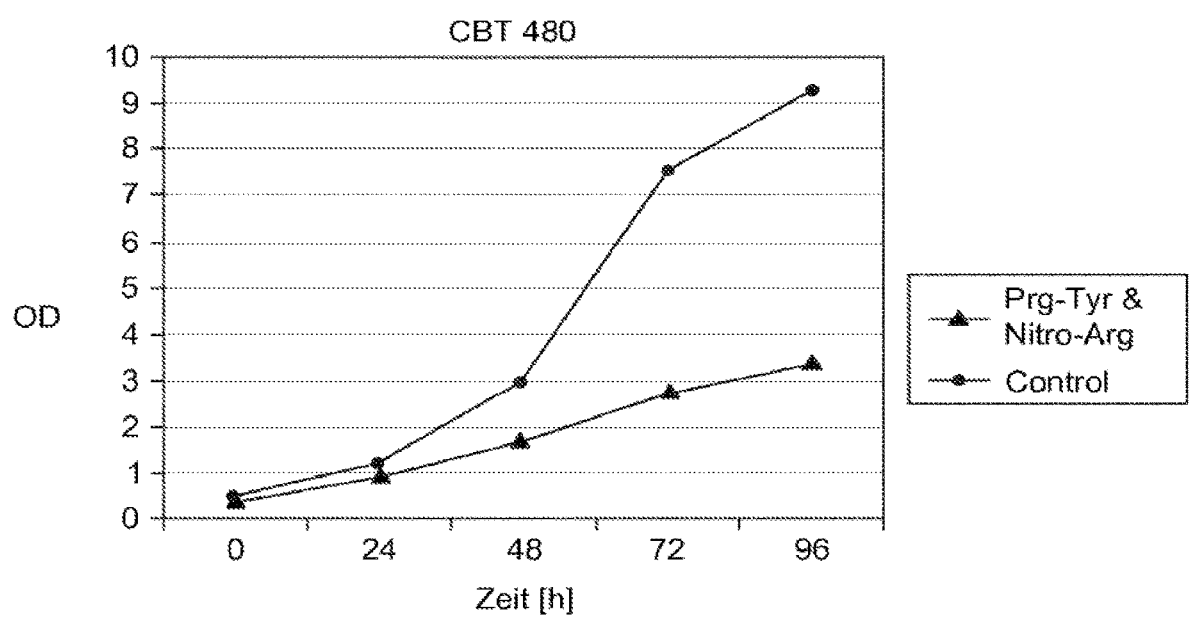
FIG. 19: Exemplary embodiment No. 7: Growths curve of CBT 480 cultures with and without Nitro-Arg (Arg=Arginine) and Prg-Tyr (Tyr=Tyrosine) added.

HPLC-PDA Chromatogram at 238 nm for sample of control cultivation (FIG. 18A) for sample of cultivation with added modified substrate (FIG. 18B). Extracted ion chromatogram from HPLC-MS data of mass value of protonated molecular ion of novel Microcystin variant for sample of control cultivation (FIG. 18C) and sample of cultivation with added modified substrate (FIG. 18D) in the positive ionization mode. Finally, (FIG. 18E) shows the averaged mass spectrum of the peak visible in chromatogram (FIG. 18D). Detector signal intensities (y-Axis) are measured in milli-absorption units (mAU) und counts (dimensionless quantity) for PDA and mass spectrometry data respectively.

FIG. 19:

Exemplary embodiment No. 7: Growths curve of CBT 480 cultures with and without Nitro-Arg (Arg=Arginine) and Prg-Tyr (Tyr=Tyrosine) added.

FIGS. 20A-20E:

Exemplary embodiment No. 8: Incorporation of the modified substrate Nitro-Arg (Arg=Arginine) into Microcystin (D-Asp3, E-Dhb7)-RR in position 2/4 produced by strain CBT 329.

Figure 20A:
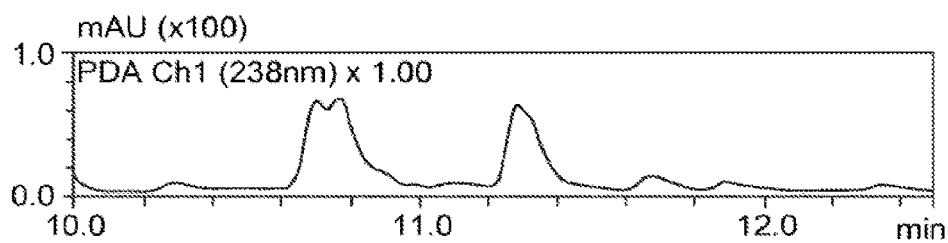
FIG. 20A: Exemplary embodiment No. 8: Incorporation of the modified substrate Nitro-Arg (Arg=Arginine) into Microcystin (D-Asp3, E-Dhb7)-RR in position 2/4 produced by strain CBT 329. HPLC-PDA Chromatogram at 238 nm for sample of control cultivation.
Figure 20B:
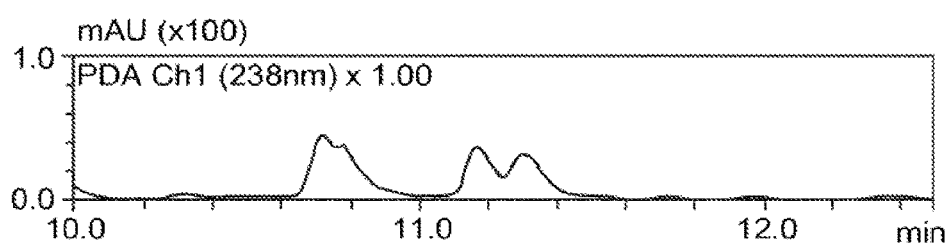
FIG. 20B: Exemplary embodiment No. 8: Incorporation of the modified substrate Nitro-Arg (Arg=Arginine) into Microcystin (D-Asp3, E-Dhb7)-RR in position 2/4 produced by strain CBT 329. HPLC-PDA Chromatogram at 238 nm for sample of cultivation with added modified substrate.
Figure 20C:
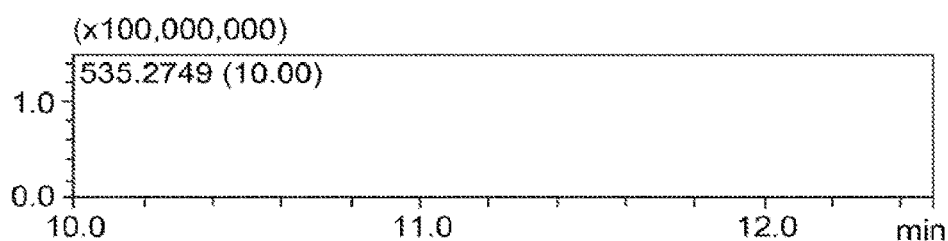
FIG. 20C: Exemplary embodiment No. 8: Incorporation of the modified substrate Nitro-Arg (Arg=Arginine) into Microcystin (D-Asp3, E-Dhb7)-RR in position 2/4 produced by strain CBT 329. Extracted ion chromatogram from HPLC-MS data of mass value of double protonated molecular ion of novel Microcystin variant for sample of control cultivation in the positive ionization mode.
Figure 20D:
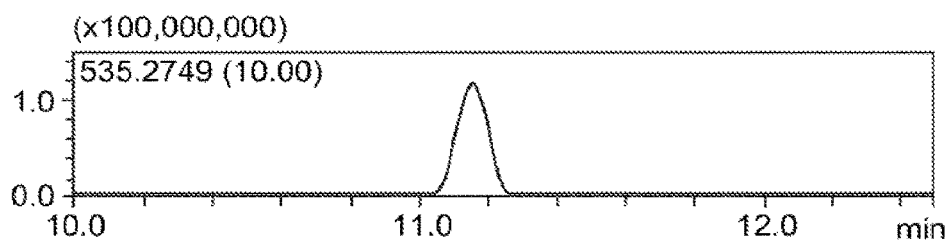
FIG. 20D: Exemplary embodiment No. 8: Incorporation of the modified substrate Nitro-Arg (Arg=Arginine) into Microcystin (D-Asp3, E-Dhb7)-RR in position 2/4 produced by strain CBT 329. Extracted ion chromatogram from HPLC-MS data of mass value of double protonated molecular ion of novel Microcystin variant for sample of cultivation with added modified substrate in the positive ionization mode.
Figure 20E:
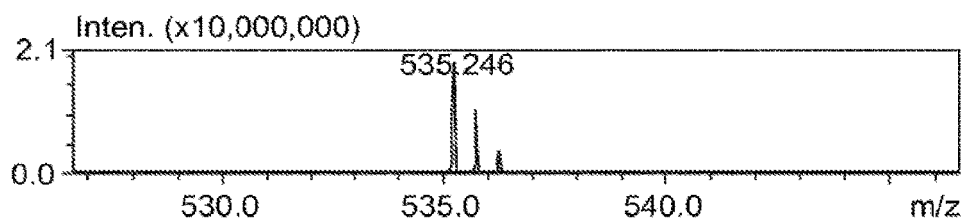
FIG. 20E: Exemplary embodiment No. 8: Incorporation of the modified substrate Nitro-Arg (Arg=Arginine) into Microcystin (D-Asp3, E-Dhb7)-RR in position 2/4 produced by strain CBT 329.
Figure 21:
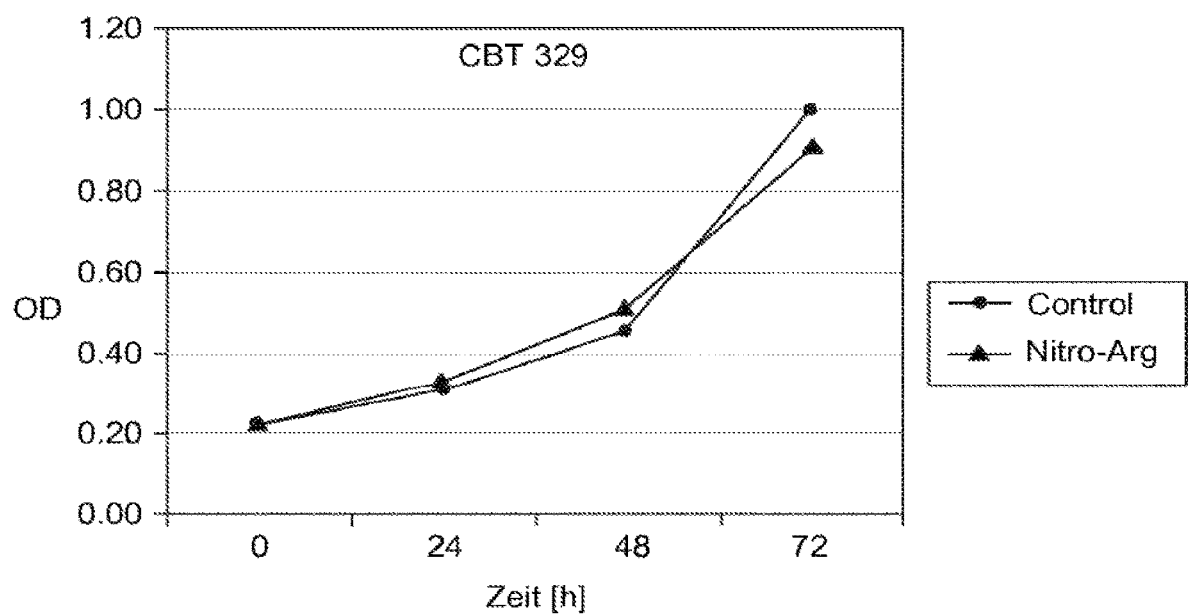
FIG. 21: Exemplary embodiment No. 8: Growths curve of CBT 329 cultures with and without Nitro-Arg (Arg=Arginine) added.

HPLC-PDA Chromatogram at 238 nm for sample of control cultivation (FIG. 20A) for sample of cultivation with added modified substrate (FIG. 20B). Extracted ion chromatogram from HPLC-MS data of mass value of double protonated molecular ion of novel Microcystin variant for sample of control cultivation (FIG. 20C) and sample of cultivation with added modified substrate (FIG. 20D) in the positive ionization mode. Finally, (FIG. 20E) shows the averaged mass spectrum of the peak visible in chromatogram (FIG. 20D). Detector signal intensities (y-Axis) are measured in milli-absorption units (mAU) und counts (dimensionless quantity) for PDA and mass spectrometry data respectively.

FIG. 21:

Exemplary embodiment No. 8: Growths curve of CBT 329 cultures with and without Nitro-Arg (Arg=Arginine) added.

FIGS. 22A-22E:

Exemplary embodiment No. 9: Incorporation of the modified substrate Azido-Lys (Lys=Lysine) into Microcystin YR in position 4 produced by strain CBT 1.

Figure 22A:
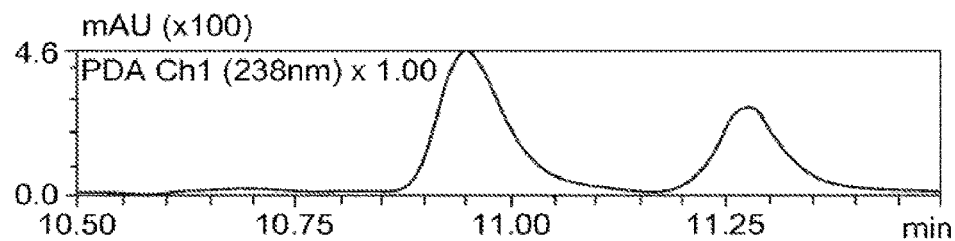
FIG. 22A: Exemplary embodiment No. 9: Incorporation of the modified substrate Azido-Lys (Lys=Lysine) into Microcystin YR in position 4 produced by strain CBT 1. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively. The PDA-Signal of the novel Azido-Lys (Lys=Lysine) variant of Microcystin YR is not visible due to overlapping peaks in the sample.
Figure 22B:
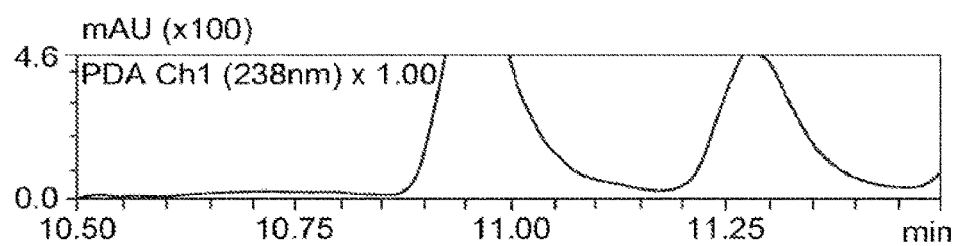
FIG. 22B: Exemplary embodiment No. 9: Incorporation of the modified substrate Azido-Lys (Lys=Lysine) into Microcystin YR in position 4 produced by strain CBT 1. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively. The PDA-Signal of the novel Azido-Lys (Lys=Lysine) variant of Microcystin YR is not visible due to overlapping peaks in the sample.
Figure 22C:
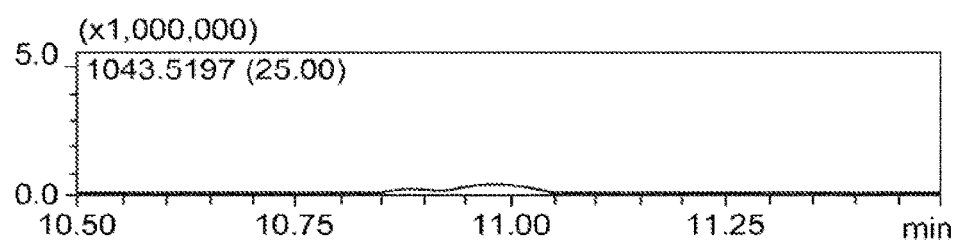
FIG. 22C: Exemplary embodiment No. 9: Incorporation of the modified substrate Azido-Lys (Lys=Lysine) into Microcystin YR in position 4 produced by strain CBT 1. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively. The PDA-Signal of the novel Azido-Lys (Lys=Lysine) variant of Microcystin YR is not visible due to overlapping peaks in the sample.
Figure 22D:
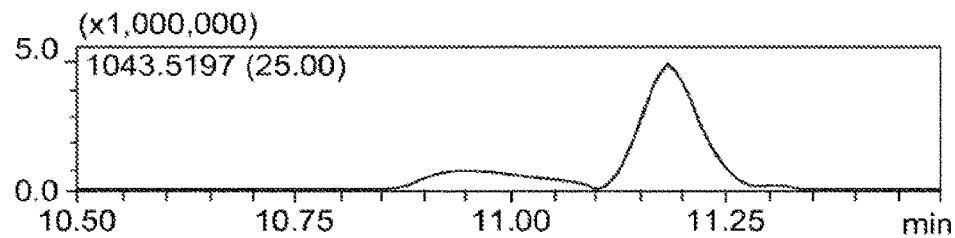
FIG. 22D: Exemplary embodiment No. 9: Incorporation of the modified substrate Azido-Lys (Lys=Lysine) into Microcystin YR in position 4 produced by strain CBT 1. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively. The PDA-Signal of the novel Azido-Lys (Lys=Lysine) variant of Microcystin YR is not visible due to overlapping peaks in the sample.
Figure 22E:
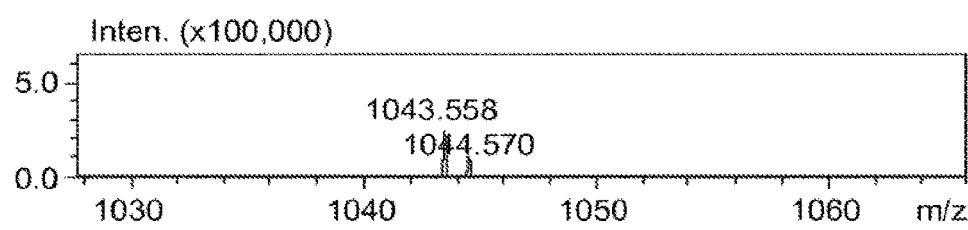
Figure 23:
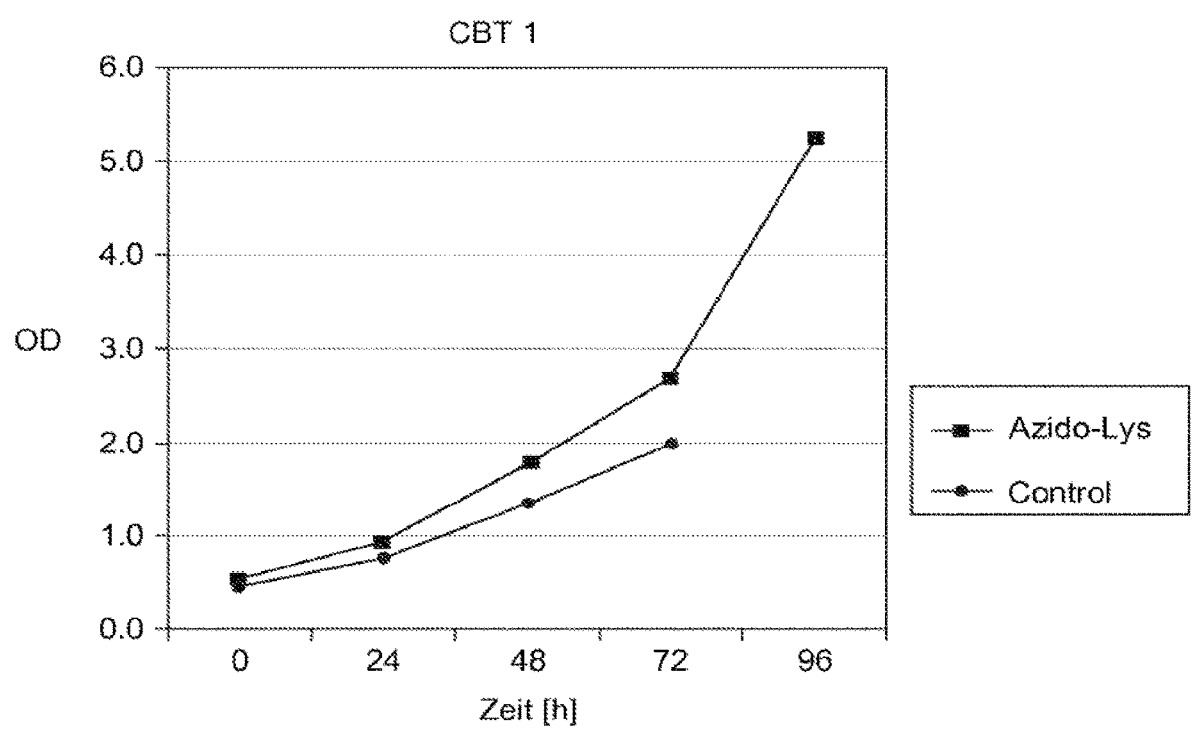
FIG. 23: Exemplary embodiment No. 9: Growths curve of CBT 1 cultures with and without Azido-Lys (Lys=Lysine) added.

HPLC-PDA Chromatogram at 238 nm for sample of control cultivation (FIG. 22A) for sample of cultivation with added modified substrate (FIG. 22B). Extracted ion chromatogram from HPLC-MS data of mass value of protonated molecular ion of novel Microcystin variant for sample of control cultivation (FIG. 22C) and sample of cultivation with added modified substrate (FIG. 22D) in the positive ionization mode. Finally, (FIG. 22E) shows the averaged mass spectrum of the peak visible in chromatogram (FIG. 22D). Detector signal intensities (y-Axis) are measured in milli-absorption units (mAU) und counts (dimensionless quantity) for PDA and mass spectrometry data respectively. The PDA-Signal of the novel Azido-Lys (Lys=Lysine) variant of Microcystin YR is not visible due to overlapping peaks in the sample.

FIG. 23:

Exemplary embodiment No. 9: Growths curve of CBT 1 cultures with and without Azido-Lys (Lys=Lysine) added.

FIGS. 24A-24E:

Exemplary embodiment No. 10: Incorporation of the modified substrate Azido-Norval (Norval=Norvaline) into Microcystin RR in position 2 produced by strain CBT 633.

Figure 24A:
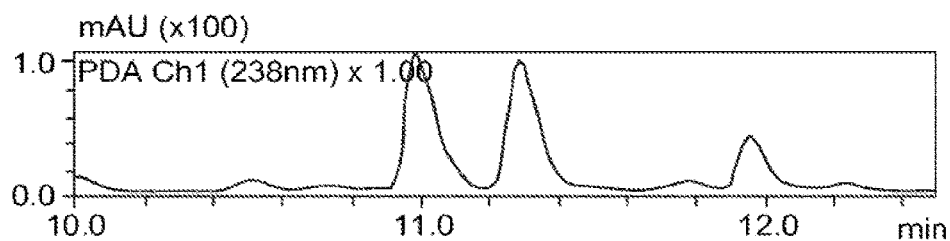
FIG. 24A: Exemplary embodiment No. 10: Incorporation of the modified substrate Azido-Norval (Norval=Norvaline) into Microcystin RR in position 2 produced by strain CBT 633. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
Figure 24B:
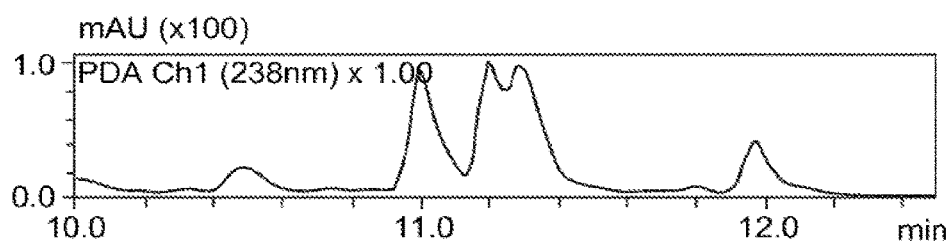
FIG. 24B: Exemplary embodiment No. 10: Incorporation of the modified substrate Azido-Norval (Norval=Norvaline) into Microcystin RR in position 2 produced by strain CBT 633. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
Figure 24C:
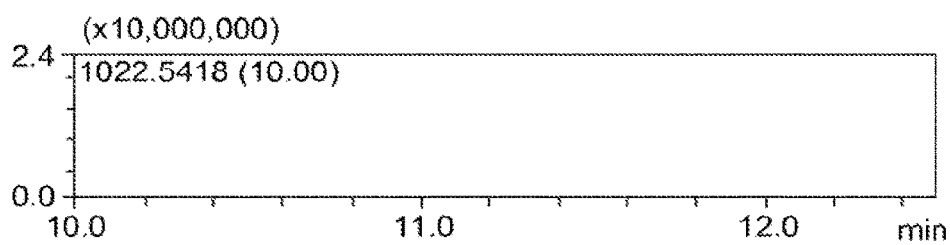
FIG. 24C: Exemplary embodiment No. 10: Incorporation of the modified substrate Azido-Norval (Norval=Norvaline) into Microcystin RR in position 2 produced by strain CBT 633. Extracted ion chromatogram from HPLC-MS data of mass value of protonated molecular ion of novel Microcystin variant for sample of control cultivation in the positive ionization mode. Detector signal intensities (y-Axis) are measured in milli-absorption units (mAU) and counts (dimensionless quantity) for PDA and mass spectrometry data respectively.
Figure 24D:
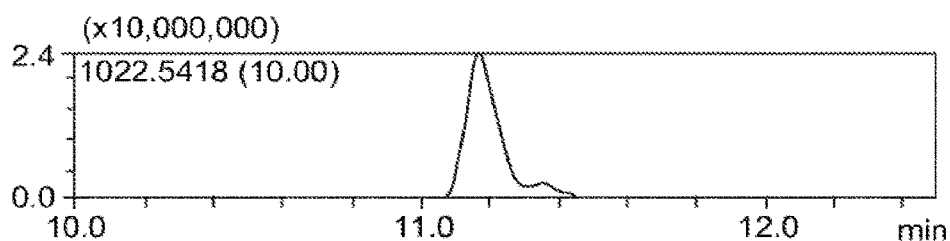
FIG. 24D: Exemplary embodiment No. 10: Incorporation of the modified substrate Azido-Norval (Norval=Norvaline) into Microcystin RR in position 2 produced by strain CBT 633. Extracted ion chromatogram from HPLC-MS data of mass value of protonated molecular ion of novel Microcystin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
Figure 24E:
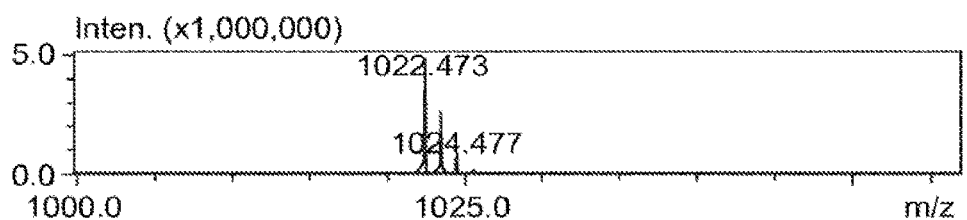
FIG. 24E: Exemplary embodiment No. 10: Incorporation of the modified substrate Azido-Norval (Norval=Norvaline) into Microcystin RR in position 2 produced by strain CBT 633.
Figure 25:
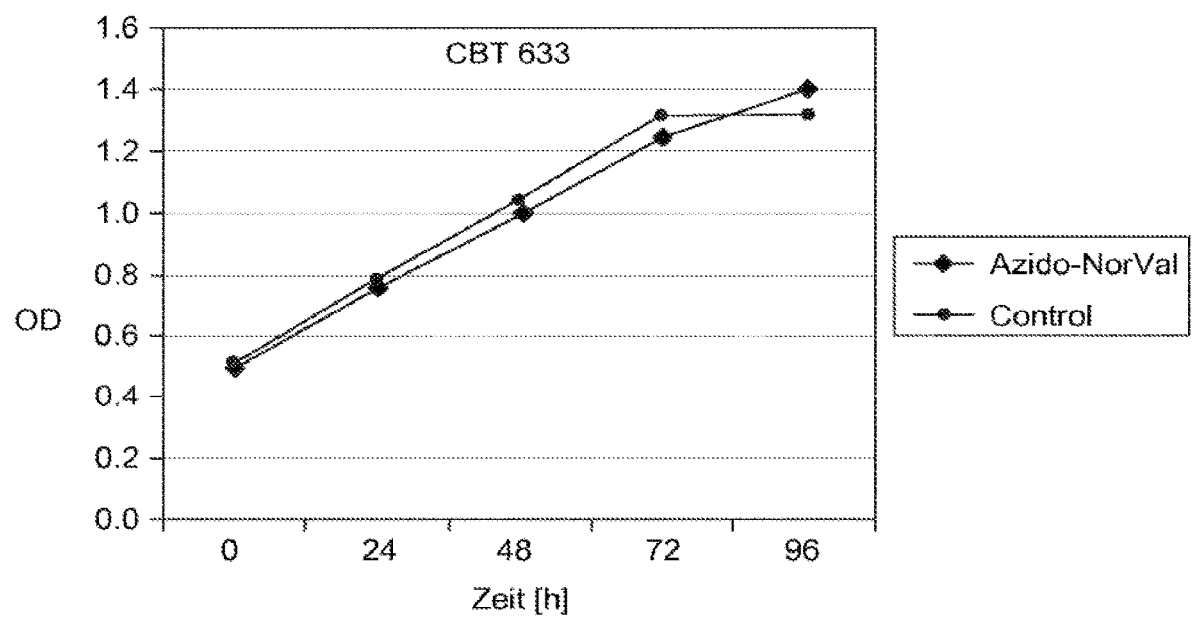
FIG. 25: Growths curve of CBT 633 cultures with and without Azido-Norval (Norval=Norvaline) added.

HPLC-PDA Chromatogram at 238 nm for sample of control cultivation (FIG. 24A) for sample of cultivation with added modified substrate (FIG. 24B). Extracted ion chromatogram from HPLC-MS data of mass value of protonated molecular ion of novel Microcystin variant for sample of control cultivation (FIG. 24C) and sample of cultivation with added modified substrate (FIG. 24D) in the positive ionization mode. Finally, (FIG. 24E) shows the averaged mass spectrum of the peak visible in chromatogram (FIG. 24D). Detector signal intensities (y-Axis) are measured in milli-absorption units (mAU) und counts (dimensionless quantity) for PDA and mass spectrometry data respectively.

FIG. 25:

Growths curve of CBT 633 cultures with and without Azido-Norval (Norval=Norvaline) added.

FIGS. 26A-26E:

Exemplary embodiment No. 11: Incorporation of the modified substrate H-homoarg-OH (homoarg=homoarginine) into Nodularin in position 2 produced by strain CBT 786.

Figure 26A:
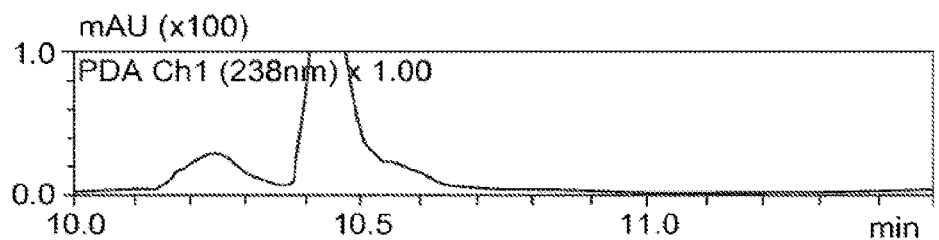
FIG. 26: Exemplary embodiment No. 11: Incorporation of the modified substrate H-homoarg-OH (homoarg=homoarginine) into Nodularin in position 2 produced by strain CBT 786. HPLC-PDA Chromatogram at 238 nm for sample of control cultivation. Detector signal intensities (y-Axis) are measured in milli-absorption units (mAU) and counts (dimensionless quantity) for PDA and mass spectrometry data respectively.
FIG. 26B: Exemplary embodiment No. 11: Incorporation of the modified substrate H-homoarg-OH (homoarg=homoarginine) into Nodularin in position 2 produced by strain CBT 786. HPLC-PDA Chromatogram at 238 nm for sample of cultivation with added modified substrate. Detector signal intensities (y-Axis) are measured in milli-absorption units (mAU) and counts (dimensionless quantity) for PDA and mass spectrometry data respectively.
FIG. 26C: Exemplary embodiment No. 11: Incorporation of the modified substrate H-homoarg-OH (homoarg=homoarginine) into Nodularin in position 2 produced by strain CBT 786. Extracted ion chromatogram from HPLC-MS data of mass value of protonated molecular ion of novel Nodularin variant for sample of control cultivation in the positive ionization mode. Detector signal intensities (y-Axis) are measured in milli-absorption units (mAU) and counts (dimensionless quantity) for PDA and mass spectrometry data respectively.
FIG. 26D: Exemplary embodiment No. 11: Incorporation of the modified substrate H-homoarg-OH (homoarg=homoarginine) into Nodularin in position 2 produced by strain CBT 786. Extracted ion chromatogram from HPLC-MS data of mass value of protonated molecular ion of novel Nodularin variant for sample of cultivation with added modified substrate in the positive ionization mode. Detector signal intensities (y-Axis) are measured in milli-absorption units (mAU) and counts (dimensionless quantity) for PDA and mass spectrometry data respectively.
FIG. 26E: Exemplary embodiment No. 11: Incorporation of the modified substrate H-homoarg-OH (homoarg=homoarginine) into Nodularin in position 2 produced by strain CBT 786.
Figure 26B:
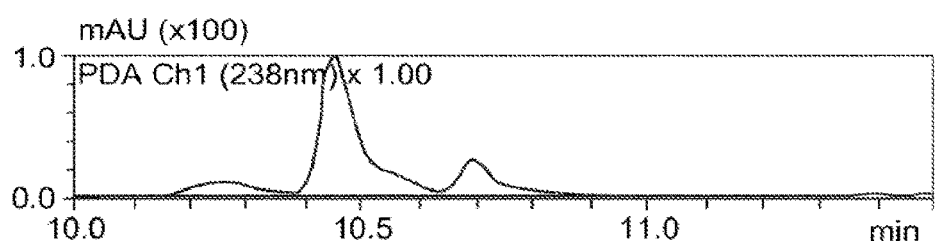
Figure 26C:
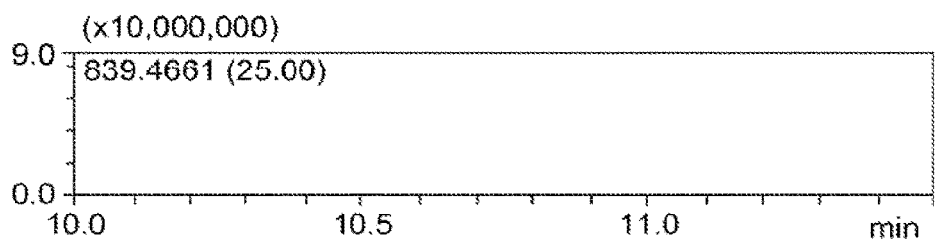
Figure 26D:
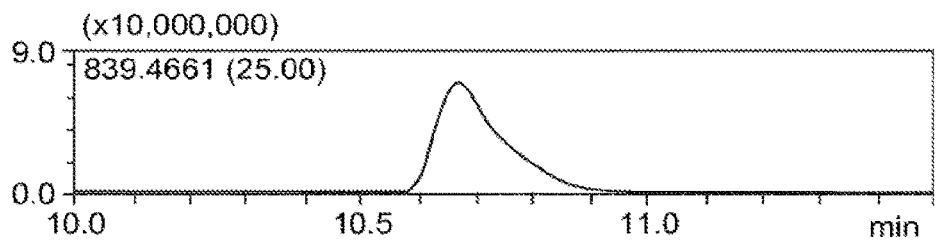
Figure 26E:
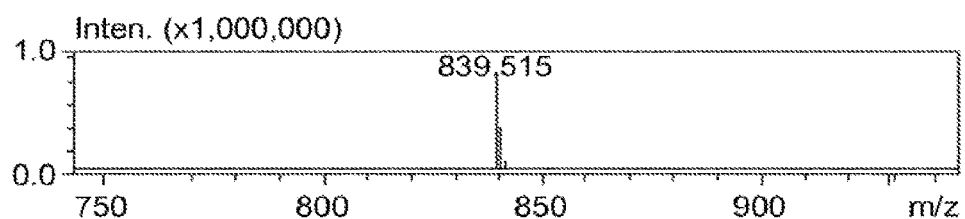

HPLC-PDA Chromatogram at 238 nm for sample of control cultivation (FIG. 26A) for sample of cultivation with added modified substrate (FIG. 26B). Extracted ion chromatogram from HPLC-MS data of mass value of protonated molecular ion of novel Nodularin variant for sample of control cultivation (FIG. 26C) and sample of cultivation with added modified substrate (FIG. 26D) in the positive ionization mode. Finally, (FIG. 26E) shows the averaged mass spectrum of the peak visible in chromatogram (FIG. 26D). Detector signal intensities (y-Axis) are measured in milli-absorption units (mAU) und counts (dimensionless quantity) for PDA and mass spectrometry data respectively.

FIGS. 27A-27E:

Exemplary embodiment No. 12: Incorporation of the modified substrate Azido-L-Phe (Phe=phenylalanine) into Microcystin YR in position 2 produced by strain CBT 480 in a large scale (2 l) cultivation system.

HPLC-PDA Chromatogram at 238 nm for sample of control cultivation (FIG. 27A) for sample of cultivation with added modified substrate (FIG. 27B). Extracted ion chromatogram from HPLC-MS data of mass value of protonated molecular ion of novel Microcystin variant for sample of control cultivation (FIG. 27C) and sample of cultivation with added modified substrate (FIG. 27D) in the positive ionization mode. Finally, (FIG. 27E) shows the averaged mass spectrum of the peak visible in chromatogram (FIG. 27D). Detector signal intensities (y-Axis) are measured in milli-absorption units (mAU) und counts (dimensionless quantity) for PDA and mass spectrometry data respectively.

FIG. 28:

Exemplary embodiment No. 13: Feeding of *Microcystis aeruginosa* strain CBT 480 with different amounts of modified substrate 4-azido-L-phenylalanine (0 µM, 10 µM, 30 µM) results an increasing amount of produced modified microcystin with increasing amount of fed modified substrate 4-azido-L-phenylalanine. This result allows for optimization of feeding protocols for respective productions of modified non-ribosomal peptides (here modified microcystins).

The upper part of the figure shows overlaid HPLC-PDA Chromatograms at 238 nm for sample of control cultivation, sample of cultivation with added substrate 4-azido-L-phenylalanine of 10 µM in culture medium and sample of cultivation with added substrate 4-azido-L-phenylalanine of 30 µM in culture medium. The lower part of the figure shows the averaged mass spectrum of the newly formed peak visible at about 10 min in the HPLC chromatogram. Detector signal intensities (y-Axis) are measured in milli-absorption units (mAU) and counts (dimensionless quantity) for PDA and mass spectrometry data, respectively.

FIGS. 29A-29E:

Exemplary embodiment No. 14: Incorporation of the modified substrate Prg-Tyr (Tyr=Tyrosine) into (D-Asp3, E-Dhb7) Microcystin-RR in position 2 produced by strain CBT 280.

HPLC-PDA Chromatogram at 238 nm for sample of control cultivation (FIG. 29A) for sample of cultivation with added modified substrate (FIG. 29B). Extracted ion chromatogram from HPLC-MS data of mass value of protonated molecular ion of novel Microcystin variant for sample of control cultivation (FIG. 29C) and sample of cultivation with added modified substrate (FIG. 29D) in the positive ionization mode. Finally, (FIG. 29E) shows the averaged mass spectrum of the peak visible in chromatogram (FIG. 29D). Detector signal intensities (y-Axis) are measured in milli-absorption units (mAU) und counts (dimensionless quantity) for PDA and mass spectrometry data respectively.

FIG. 30:

Exemplary embodiment No. 20: Produced ADCs and results of analytical SEC-HPLC. In analytical SEC-HPLC the conjugates Microcystin-ADC1 and Microcystin-ADC2 showed a high level of purity with 98.9% and 99.0% monomers. In both cases, aggregates and small fragments were detected with rates of 0.8% and 0.2%.

FIG. 31:

Exemplary embodiment No. 21: Coomassie stained Gelelectrophoresis gels demonstrating the binding of Microcystin variants 1 and 2 as payloads on monoclonal antibodies. In Coomassie staining under reducing conditions all samples showed a signal for the heavy chain at app. 50 kDa and the light chain at app. 25 kDa. All conjugates showed an up-shift of the protein signal of the heavy and the light chain compared to the naked MAB indicating toxin conjugation to both antibody chains. For all ADCs a double-signal was detected for the light chain indicating both, conjugated and unconjugated species. In Coomassie staining under non-reducing conditions the naked antibody showed a double signal at app. 150 kDa for the intact antibody. The ADCs showed a variety of signals between 25 kDa and 150 kDa, since in both cases the toxin was conjugated to reduced interchain disulfides leading to instability of the antibody during incubation at 37° C.

FIG. 32:

Exemplary embodiment No. 22: Successful in vitro proof of concept of Microcystin-based ADCs. The cell viability is monitored in an in-vitro-assay with a cancer cell line for the different concentrations of the Microcystin ADC for two Microcystin variants as payloads. The ADC carries a non-cleavable linker. For Microcystin-ADC-2 an $EC_{50}$ values of 220 µM was determined. Differences between structural payload variants underline huge potential of further structural optimizations.

The invention claimed is:

1. An antibody-drug conjugate, comprising:
an antibody or a fragment thereof containing an antigen binding site that immuno-specifically binds to a tumor associated antigen,
a modified microcystin comprising an amino acid with an anchor group attached to said antibody or said fragment thereof, wherein the modified microcystin has the following general structure cyclo(-D-Ala$_1$-$X_2$-D-$MeAsp_3$-$Z_4$-$Adda_5$-D-$Glu_6$-$Mdha_7$), wherein, independently from each other, D-$Ala_1$ and D-$MeAsp_3$ each represent a variable D-amino acid position, $Adda_5$ is selected from the group consisting of Adda, DM-Adda, (6Z) Adda, and ADM-Adda, D-$Glu_6$ is selected from the group consisting of D-Glu and D-Glu($OCH_3$), $Mdha_7$ is selected from the group consisting of Mdha, Dha, L-Ser, L-MeSer, Dhb, and MeLan, and $X_2$ and $Z_4$ are, independently from each other, an L-amino acid, wherein said amino acid with said anchor group is incorporated in at least one position other than $Adda_5$ and $DGlu_6$ and wherein said anchor group is derived from chemically conjugating a group selected from the group consisting of an azido group, an alkyne group, a tetrazine, a primary amine, a thiol, an aldehyde, a carboxyl, and an oxime of said amino acid to said antibody or said fragment thereof, thereby attaching said modified microcystin to said antibody or said fragment thereof via conjugation chemistry, and wherein said antibody-drug conjugate is cytotoxic.

2. The antibody-drug conjugate according to claim 1, wherein said amino acid with said anchor group is incorporated in position $X_2$ and/or $Z_4$.

3. The antibody-drug conjugate according to claim 1, wherein said at least one position is $X_2$.

4. The antibody-drug conjugate according to claim 1, wherein said at least one position is $Z_4$.

5. The antibody-drug conjugate according to claim 1, wherein said amino acid with said anchor group is derived from the group consisting of (2S)-2-amino-3-azidopropanoic acid, (2S)-2-amino-6-azidohexanoic acid, (S)-2-amino-5-azidopentanoic acid, (2S)-2-amino-3-(4-prop-2-ynyloxyphenyl)propanoic acid, (2S)-2-amino-5-(N'- nitrocarbamimidamido)pentanoic acid, (2S)-2-amino-3-(furan-2-yl)propanoic acid, (S)-amino-6-((prop-2-ynyloxy)carbonylamino)hexanoic acid, and (2S)-2-amino-3-(4-azidophenyl)propanoic acid.

6. The antibody-drug conjugate according to claim 1, wherein,
   D-Ala$_1$ is selected from the group consisting of D-Ala, D-Ser and D-Leu,
   D-MeAsp$_3$ is selected from the group consisting of D-MeAsp and D-Asp, and/or
   X$_2$ and/or Z$_4$ comprises said amino acid with said anchor group.

7. The antibody-drug conjugate according to claim 1, wherein the conjugation chemistry is at least one selected from the group consisting of copper(I)-catalyzed azide-alkyne cycloaddition, strain promoted azide-alkyne cycloaddition, alkyne-azide cycloaddition, alkene-tetrazine inverse-demand Diels-Alder reaction, and a reaction exploiting the specific reactivity of the primary amine, the thiol, the aldehyde, the carboxyl, and the oxime.

8. The antibody-drug conjugate according to claim 1, wherein said amino acid with said anchor group comprises:
   a modified amino acid which is, in nature, not incorporated at the specific position in said modified microcystin and which is also not a substitution of the naturally incorporated amino acid with functional groups which are not directly accessible or transformable for use in conjugation chemistry, for the attachment of the antibody or the fragment thereof or a label.

9. The antibody-drug conjugate according to claim 1, wherein the modified microcystin comprises:
   a chemical structure, wherein a natural receptor or transporter in a target cell which, in-vivo, is capable of intracellular uptake of members of the same microcystin group into the target cell, is capable of uptake of the modified microcystin comprising the chemical structure only at a very low rate which is at least 50 times lower than the rate for microcystin-LR transported by organic anion transporting polypeptide 1B1 (OATP1B1) to restrict uptake of the compound into human cells that express OATP1B1.

10. The antibody-drug conjugate according to claim 1, wherein the modified microcystin comprises:
    a chemical structure having drug-like properties that are changed to its advantage for their application as payload for an antibody-drug conjugate, in comparison to microcystin-LR, by at least 10%.

11. The antibody-drug conjugate according to claim 10, wherein the drug-like properties comprise solubility in water, stability under low pH, pharmacokinetics, and pharmacodynamics.

12. The antibody-drug conjugate according to claim 1, wherein D-MeAsp$_3$ is selected from the group consisting of D-MeAsp and D-Asp, and
    wherein said amino acid with said anchor group is incorporated in at least one position selected from the group consisting of D-Ala$_1$, X$_2$, Z$_4$ and Mdha$_7$.

13. The antibody-drug conjugate according to claim 1, wherein D-MeAsp$_3$ is selected from the group consisting of D-MeAsp and D-Asp, and D-Ala$_1$ is selected from the group consisting of D-Ala, D-Ser and D-Leu, and
    wherein said amino acid with said anchor group is incorporated in at least one position selected from the group consisting of X$_2$ and Z$_4$.

14. The antibody-drug conjugate according to claim 12, wherein said anchor group is attached to said antibody or said fragment thereof via a linker.

15. The antibody-drug conjugate according to claim 14, wherein said anchor group is included in a click chemistry attachment that conjugates said modified microcystin via said linker with said antibody.

* * * * *

SEQUENCE LISTING

<160> NUMBER OF SEQ ID NOS: 3

<210> SEQ ID NO 1
<211> LENGTH: 7
<212> TYPE: PRT
<213> ORGANISM: Microcystis aeruginosa
<220> FEATURE:
<221> NAME/KEY: MOD_RES
<222> LOCATION: (1)..(1)
<223> OTHER INFORMATION: D-Ala, D-Ser, D-Leu, Azido-L-Ala, Azido-Lys,

```
                    Azido-Norval, Prg-Tyr, Nitro-Arg, Furyl-Ala, Lys(Poc), Azido-L-Phe
                    or H-homo-Arg-OH
<220> FEATURE:
<221> NAME/KEY: MOD_RES
<222> LOCATION: (2)..(2)
<223> OTHER INFORMATION: L-Leu, L-Ala, L-Tyr, L-Glu, L-Val, L-Glu(OMe),
                    L-Arg, L-Phe, L-Met(O), L-H-Phe, L-H-Tyr, L-Trp, L-H-Arg, L-H-Ile,
                    L-H4Tyr, Azido-L-Ala, Azido-Lys, Azido-Norval, Prg-Tyr, Nitro-Arg,
                    Furyl-Ala, Lys(Poc), Azido-L-Phe or H-homo-Arg-OH
<220> FEATURE:
<221> NAME/KEY: MOD_RES
<222> LOCATION: (3)..(3)
<223> OTHER INFORMATION: D-Asp, D-MeAsp, Azido-L-Ala, Azido-Lys, Azido-
                    Norval, Prg-Tyr, Nitro-Arg, Furyl-Ala, Lys(Poc), Azido-L-Phe or
                    H-homo-Arg-OH
<220> FEATURE:
<221> NAME/KEY: MOD_RES
<222> LOCATION: (4)..(4)
<223> OTHER INFORMATION: L-Ala, Aba, L-Leu, L-Arg, L-Glu, L-Glu(OMe),
                    L-Phe, L-Tyr, L-LHar, L-Trp, L-Met(O), L-H-Arg, Azido-L-Ala,
                    Azido-Lys, Azido-Norval, Prg-Tyr, Nitro-Arg, Furyl-Ala, Lys(Poc),
                    Azido-L-Phe or H-homo-Arg-OH
<220> FEATURE:
<221> NAME/KEY: VARIANT
<222> LOCATION: (5)..(5)
<223> OTHER INFORMATION: Adda, DM-Adda, (6Z)Adda or ADM-Adda
<220> FEATURE:
<221> NAME/KEY: VARIANT
<222> LOCATION: (6)..(6)
<223> OTHER INFORMATION: D-Glu or D-Glu(OCH3)
<220> FEATURE:
<221> NAME/KEY: MOD_RES
<222> LOCATION: (7)..(7)
<223> OTHER INFORMATION: Mdha, Dha, L-Ser, L-MeSer, Dhb, MeLan, Azido-L-
                    Ala, Azido-Lys, Azido-Norval, Prg-Tyr, Nitro-Arg, Furyl-Ala,
                    Lys(Poc), Azido-L-Phe or H-homo-Arg-OH

<400> SEQUENCE: 1

Xaa Xaa Xaa Xaa Xaa Glu Xaa
1               5

<210> SEQ ID NO 2
<211> LENGTH: 5
<212> TYPE: PRT
<213> ORGANISM: Nodularia sp.
<220> FEATURE:
<221> NAME/KEY: MOD_RES
<222> LOCATION: (1)..(1)
<223> OTHER INFORMATION: MeAsp, D-MeAsp, D-Asp, Azido-L-Ala, Azido-Lys,
                    Azido-Norval, Prg-Tyr, Nitro-Arg, Furyl-Ala, Lys(Poc), Azido-L-Phe
                    or H-homo-Arg-OH
<220> FEATURE:
<221> NAME/KEY: MOD_RES
<222> LOCATION: (2)..(2)
<223> OTHER INFORMATION: Arg, Homo-Arg, Azido-L-Ala, Azido-Lys, Azido-
                    Norval, Prg-Tyr, Nitro-Arg, Furyl-Ala, Lys(Poc), Azido-L-Phe or
                    H-homo-Arg-OH
<220> FEATURE:
<221> NAME/KEY: VARIANT
<222> LOCATION: (3)..(3)
<223> OTHER INFORMATION: Adda, DM-Adda, (6Z)Adda or MeAdda
<220> FEATURE:
<221> NAME/KEY: VARIANT
<222> LOCATION: (4)..(4)
<223> OTHER INFORMATION: D-Glu or D-Glu(OCH3)
<220> FEATURE:
<221> NAME/KEY: MOD_RES
<222> LOCATION: (5)..(5)
<223> OTHER INFORMATION: Mdhb, Dhb, Azido-L-Ala, Azido-Lys, Azido-
                    Norval, Prg-Tyr, Nitro-Arg, Furyl-Ala, Lys(Poc), Azido-L-Phe or
                    H-homo-Arg-OH

<400> SEQUENCE: 2

Xaa Xaa Xaa Glu Xaa
1               5
```

```
<210> SEQ ID NO 3
<211> LENGTH: 7
<212> TYPE: PRT
<213> ORGANISM: Planktothrix rubescence
<220> FEATURE:
<221> NAME/KEY: MOD_RES
<222> LOCATION: (1)..(1)
<223> OTHER INFORMATION: D-Ala, D-Ser, D-Leu, Azido-L-Ala, Azido-Lys,
      Azido-Norval, Prg-Tyr, Nitro-Arg, Furyl-Ala, Lys(Poc), Azido-L-Phe
      or H-homo-Arg-OH
<220> FEATURE:
<221> NAME/KEY: MOD_RES
<222> LOCATION: (2)..(2)
<223> OTHER INFORMATION: L-Leu, L-Ala, L-Tyr, L-Glu, L-Val, L-Glu(OMe),
      L-Arg, L-Phe, L-Met(O), L-H-Phe, L-H-Tyr, L-Trp, L-H-Arg, L-H-Ile,
      L-H4Tyr, Azido-L-Ala, Azido-Lys, Azido-Norval, Prg-Tyr, Nitro-Arg,
      Furyl-Ala, Lys(Poc), Azido-L-Phe or H-homo-Arg-OH
<220> FEATURE:
<221> NAME/KEY: MOD_RES
<222> LOCATION: (3)..(3)
<223> OTHER INFORMATION: D-Asp, D-MeAsp, Azido-L-Ala, Azido-Lys, Azido-
      Norval, Prg-Tyr, Nitro-Arg, Furyl-Ala, Lys(Poc), Azido-L-Phe or
      H-homo-Arg-OH
<220> FEATURE:
<221> NAME/KEY: MOD_RES
<222> LOCATION: (4)..(4)
<223> OTHER INFORMATION: L-Ala, Aba, L-Leu, L-Arg, L-Glu, L-Glu(OMe),
      L-Phe, L-Tyr, L-LHar, L-Trp, L-Met(O), L-H-Arg, Azido-L-Ala,
      Azido-Lys, Azido-Norval, Prg-Tyr, Nitro-Arg, Furyl-Ala, Lys(Poc),
      Azido-L-Phe or H-homo-Arg-OH
<220> FEATURE:
<221> NAME/KEY: VARIANT
<222> LOCATION: (5)..(5)
<223> OTHER INFORMATION: Adda, DM-Adda, (6Z)Adda or ADM-Adda
<220> FEATURE:
<221> NAME/KEY: VARIANT
<222> LOCATION: (6)..(6)
<223> OTHER INFORMATION: D-Glu or D-Glu(OCH3)
<220> FEATURE:
<221> NAME/KEY: MOD_RES
<222> LOCATION: (7)..(7)
<223> OTHER INFORMATION: Mdha, Dha, L-Ser, L-MeSer, Dhb, MeLan, Azido-L-
      Ala, Azido-Lys, Azido-Norval, Prg-Tyr, Nitro-Arg, Furyl-Ala,
      Lys(Poc), Azido-L-Phe or H-homo-Arg-OH

<400> SEQUENCE: 3

Xaa Xaa Xaa Xaa Xaa Glu Xaa
1               5
```